(12) United States Patent
Holsinger

(10) Patent No.: US 8,211,897 B2
(45) Date of Patent: Jul. 3, 2012

(54) INHIBITORS OF CATHEPSIN B

(75) Inventor: Leslie Holsinger, Los Altos, CA (US)

(73) Assignee: ViroBay, Inc., Menlo Park, CA (US)

( * ) Notice: Subject to any disclaimer, the term of this patent is extended or adjusted under 35 U.S.C. 154(b) by 428 days.

(21) Appl. No.: 12/366,504

(22) Filed: Feb. 5, 2009

(65) Prior Publication Data

US 2009/0203629 A1 Aug. 13, 2009

Related U.S. Application Data

(60) Provisional application No. 61/027,007, filed on Feb. 7, 2008.

(51) Int. Cl.
*C07D 401/02* (2006.01)
*A61K 31/47* (2006.01)

(52) U.S. Cl. ............... 514/260.1; 514/309; 514/312; 514/422; 514/423; 544/253; 546/141; 546/143; 546/153; 546/159; 548/517; 548/536

(58) Field of Classification Search .................. None
See application file for complete search history.

(56) References Cited

U.S. PATENT DOCUMENTS

| 6,268,207 B1 | 7/2001 | Bailey |
| 6,404,397 B1 | 6/2002 | Grinberg et al. |
| 6,492,383 B1 | 12/2002 | Munchhof et al. |
| 6,608,027 B1 | 8/2003 | Tsantrizos et al. |
| 2003/0153508 A1 | 8/2003 | Ohmoto et al. |
| 2003/0191067 A1 | 10/2003 | Llinas-Brunet et al. |
| 2006/0276407 A1 | 12/2006 | Albrecht et al. |
| 2007/0054864 A1 | 3/2007 | Graupe et al. |

FOREIGN PATENT DOCUMENTS

| WO | WO 99/24440 A1 | 5/1999 |
| WO | WO 2005/028501 A1 | 3/2005 |
| WO | WO 2006/113942 A2 | 10/2006 |
| WO | WO 2006/130552 A2 | 12/2006 |
| WO | WO 2006/130554 A2 | 12/2006 |
| WO | WO 2006/130688 A2 | 12/2006 |

OTHER PUBLICATIONS

Baskin-Bey et al. "Cathepsin B inactivation attenuates hepatocyte apoptosis and liver damage in steatotic livers after cold ischemia-warm reperfusion injury," Am J Physiol Gastrointest Liver Physiol, 2005, vol. 288, pp. G396-G402. First Published Oct 7, 2004; doi:10.1152/ajpgi.00316.2004.
Bell-McGuinn et al. "Inhibition of Cysteine Cathepsin Protease Activity Enhances Chemotherapy Regimens by Decreasing Tumor Growth and Invasiveness in a Mouse Model of Multistage Cancer," Cancer Res, 2007, vol. 67, No. 15, pp. 7378-7385.
Büth et al. "Cathepsin B is essential for regeneration of scratch-wounded normal human epidermal keratinocytes," Eur. J. Cell. Biol., 2007, doi. 10.1016/j.ejcb. 2007.03.009.
Canbay et al. "Cathepsin B inactivation attenuates hepatic injury and fibrosis during cholestasis," The Journal of Clinical Investigation, 2003, vol. 112, No. 2, pp. 152-159.
Feldstein et al. "Free Fatty Acids Promote Hepatic Lipotoxicity by Stimulating TNF-α Expression via a Lysosomal Pathway," Hepatology, 2004, pp. 185-194.
Gocheva et al. "Cysteine Cathepsins and the Cutting Edge of Cancer Invasion," Cell Cycle, 2007, vol. 6, No. 1, pp. 60-64.
Guicciardi et al, "Cathepsin B Knockout Mice Are Resistant to Tumor Necrosis Factor-α-Mediated Hepatocyte Apoptosis and Liver Injury," American Journal of Pathology, 2001, vol. 159, No. 6, pp. 2045-2054.
Guicciardi et al. "Cathepsin B contributes to TNF-α-mediated hepatocyte apoptosis by promoting mitochondrial release of cytochrome c" Journal of Clinical Investigation, 2000, vol. 106, No. 9, pp. 1127-1137.
Ha et al. "Cathepsin B is Involved in the Trafficking of TNF-α-Containing Vesicles to the Plasma Membrane in Macrophages," The Journal of Immunology, 2008, vol. 181, pp. 690-697.
Halangk et al. "Role of cathepsin B in intracellular trypsinogen activation and the onset of acute pancreatitis," The Journal of Clinical Investigation, 2000, vol. 106, No. 6, pp. 773-781.
Hook et al. "Cysteine protease inhibitors effectively reduce in vivo levels of brain β-amyloid related to Alzheimer's disease," Biol. Chem., 2007, vol. 388, pp. 247-252.
Hook et al. "Cysteine protease inhibitors reduce brain β-amyloid and β-secretase activity in vivo and are potential Alzheimer's disease therapeutics," Biol. Chem., 2007, vol. 388, pp. 979-983.
Hook et al. "Genetic cathepsin b deficiency reduces β-amyloid in transgenic mice expressing human wild-type amyloid prescursor protein," *Biochemical and Biophysical Research Communications* (2009), doi: 10.1016/j.bbrc.2009.05.131.
Joyce et al. "Cathepsin cystein proteases are effectors of invasive growth and angiogenesis during multistage tumorigenesis," Cancer Cell, 2004, vol. 5, pp. 443-453. Kukor et al. "Presence of Cathepsin B in the Human Pancreatic Secretory Pathway and Its Role in Trypsinogen Activation during Hereditary Pancreatits," The Journal of Biological Chemistry, 2002, vol. 277, No. 24, pp. 21389-21393.
Lerch et al. "Human pancreatitis and the role of cathepsin B," Gut, 2006, vol. 55, Issue No. 9, pp. 1228-1230.

(Continued)

*Primary Examiner* — Zinna Northington Davis
(74) *Attorney, Agent, or Firm* — Kilpatrick, Townsend & Stockton LLP

(57) ABSTRACT

The present invention is directed to a method of using compounds of Formula (I) to inhibit Cathepsin B. Specifically the compounds of the present invention are useful as therapeutic agents for the treatment of tumor invasion, metastasis, Alzheimer's Disease, arthritis, inflammatory diseases such as chronic and acute pancreatitis, inflammatory airway disease, and bone and joint disorders, including osteoporosis, osteoarthritis, rheumatoid arthritis, psoriasis, and other autoimmune disorders, liver fibrosis, including liver fibrosis associated with HCV, all types of steatosis (including non-alcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis and fibrosis/gliosis in the eye, schleroderma, and systemic sclerosis. The compounds of Formula (I) are also useful for treating subjects with both HCV and fibrosis in a mammal, particularly liver fibrosis, and subjects affirmatively diagnosed or at risk for both HCV and liver fibrosis.

25 Claims, 3 Drawing Sheets

OTHER PUBLICATIONS

Mahurkar et al. "Association of cathepsin B gene polymorphisms with tropical calcific pancreatitis," Gut, 2006, vol. 55, Issue No. 9, pp. 1270-1275.

Palermo et al. "Cysteine cathepsin proteases as pharmacological targets in cancer," Trends Pharmacol. Sci. 2007, doi:10.1016/j.tips.2007.10.011.

Saluja et al. "Cerulein-Induced in Vitro Activiation of Trypsinogen in Rat Pancreatic Acini is Mediated by Cathepsin B," Gastroenterology, 1997, vol. 113, pp. 304-310.

Van Acker et al. "Cathepsin B inhibition prevents trypsinogen activation and reduces pancreatitis severity," Am J. Physiol Gastroitest Liver Physiol, 2002, vol. 283: G794-G800.

Van Acker et al. "Cause-Effect Relationships Between Zymogen Activation and Other Early Events in Secretagogue-Induced Acute Pancreatitis," Am J Physiol Gastrointest Liver Physiol, 2007, doi:10.1152/ajpgi.00543.2006, pp. 1-38.

Vasiljeva et al "Tumor Cell-Derived and Macrophage-Derived Cathepsin B Promotes Progression and Lung Metastasis of mammary Cancer," Cancer Res, 2006, vol. 66, No. 10, pp. 5242-5250.

Vasiljeva et al. "Reduced tumour cell proliferation and delayed development of high-grade mammary carcinomas in cathepsin B-deficient mice," Oncogene, 2008, pp. 1-9.

Weiss et al. "Germline Mutations and Gene Polymorphism Associated with Human Pancreatitis," Endocrinol Metabl Clin N Am, 2006, vol. 35, pp. 289-302.

Wernerburg et al, "Tumor necrosis factor-α-associated lysosomal permeabilization is cathepsin B dependent," Am J Physiol Gastrointest Liver Physiol, 2002, vol. 283, pp. G947-G956.

Gocheva et al. "Distinct roles for cysteine cathepsin genes in multi-stage tumorigenesis," Genes & Development, Feb. 15, 2006, vol. 20, pp. 543-556.

Potency of Compound 1 and Compound 2 in Cellular Activity-based Probe Assay

Figure 2A and 2B: Compound 1 Reduced Plasma ALT and AST in a Model of Liver Fibrosis Figure 3: Compound 1 Reduced Liver Hydroxyproline Levels in a Model of Liver Fibrosis

INHIBITORS OF CATHEPSIN B

CROSS-REFERENCES TO RELATED APPLICATIONS

This application claims the benefit of U.S. Provisional Application No. 61/027,007, filed Feb. 7, 2008, which is hereby incorporated by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is directed to a method of inhibiting Cathepsin B, a lysosome cysteine protease.

Cysteine proteases such as Cathepsins B, H, K, L, O and S, represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, has pathological consequences. In this regard, certain cysteine proteases are associated with a number of disease states, including arthritis, muscular dystrophy, inflammation, tumor invasion, glomerulonephritis, periodontal disease, and metachromatic leukodystrophy. For example, increased Cathepsin B levels and redistribution of the enzyme are found in tumors, thus demonstrating a role for the enzyme in tumor invasion and metastasis. In addition, aberrant Cathepsin B activity is implicated in such disease states as Alzheimer's Disease, arthritis, inflammatory diseases such as chronic and acute pancreatitis, inflammatory airway disease, and bone and joint disorders, including osteoporosis, osteoarthritis, rheumatoid arthritis, psoriasis, and other autoimmune disorders.

Cathepsin B is also associated with fibrotic disease, including HCV-associated liver fibrosis, all types of steatosis (including non-alcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis and fibrosis/gliosis in the eye, scleroderma, and systemic sclerosis.

In view of the number of diseases or conditions related to the normal activity or the increased expression of Cathepsin B, compounds that are capable of inhibiting enzymatic protease activity or expression would accordingly be useful.

Compounds that were disclosed in U.S. Patent Application Publication No. 2007/0054864, filed Jun. 28, 2006, and U.S. Patent Application Ser. No. 60/878,544, the complete disclosures of which are hereby incorporated by reference, were shown to have the ability to inhibit HCV replication, and are therefore useful in treating hepatitis C.

Surprisingly, we have discovered that these compounds, and analogs of these compounds, are also useful as inhibitors of the cysteine protease Cathepsin B. Accordingly, such compounds are useful as therapeutic agents for the treatment of tumor invasion, metastasis, Alzheimer's Disease, arthritis, inflammatory diseases such as chronic and acute pancreatitis, inflammatory airway disease, and bone and joint disorders, including osteoporosis, osteoarthritis, rheumatoid arthritis, psoriasis, and other autoimmune disorders, liver fibrosis, including liver fibrosis associated with HCV, all types of steatosis (including non-alcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis and fibrosis/gliosis in the eye, scleroderma, and systemic sclerosis.

It is clear that the ability of a single compound to both inhibit HCV replication and Cathepsin B in a mammal is an advantageous property, in that viruses, including chronic HCV infection, promote inflammation and liver injury. As a direct result of this inflammation and liver injury HCV can lead to progressive liver fibrosis, with a number of chronic HCV-infected patients eventually developing cirrhosis. A majority of the serious complications associated with chronic HCV infection results from the development of liver cirrhosis. The treatment of subjects with such a compound, with the ability to inhibit HCV replication and directly reduce fibrotic disease, would improve clinical outcomes.

BRIEF SUMMARY OF THE INVENTION

In one aspect, this invention is directed to a method of inhibiting Cathepsin B activity in a mammal, comprising administering to a mammal a therapeutically effective amount of a compound of Formula (I) or a pharmaceutically acceptable salt thereof:

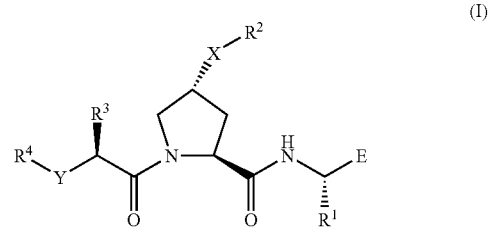

in which:

E is selected from the group consisting of —COCONR$^5$R$^6$, —COCF$_2$CONR$^5$R$^6$, —COCF$_2$C(O)OR$^5$, —COCOR$^7$, —COCF$_2$R$^8$, —COR$^9$, —COCOOR$^{10}$, —CONR$^{11}$R$^{12}$, and —B(OR$^{13}$)$_2$ where R$^5$, R$^6$, R$^7$, R$^9$, R$^{10}$, R$^{11}$, R$^{12}$ and each R$^{13}$ are independently selected from hydrogen, alkyl, alkenyl, alkynyl, cycloalkyl, cycloalkylalkyl, aryl, aralkyl, heteroaryl, heteroaralkyl, heterocyclyl, and heterocyclylalkyl and R$^8$ is selected from halo, alkyl, alkenyl, alkynyl, cycloalkyl, cycloalkylalkyl, aryl, aralkyl, heteroaryl, heteroaralkyl, heterocyclyl, and heterocyclylalkyl wherein the aliphatic, alicyclic and aromatic groups in E are optionally substituted with one, two, or three R$^a$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, alkenyloxycarbonyl, alkynyloxycarbonyl, alkenylaminocarbonyl, acylamino, aminocarbonyl, halo, and cyano and further wherein the aromatic or alicyclic ring in R$^a$ is optionally substituted with one, two, or three substituents independently selected from alkyl, alkoxy, halo, haloalkyl, haloalkoxy, carboxy, and carboxyalkyl; and optionally, $R^5$ and $R^6$, and $R^{11}$ and $R^{12}$ can be combined with the nitrogen to which they are attached to form a five- to seven-membered ring;

$R^1$ is selected from the group consisting of selected from alkyl, haloalkyl, alkenyl, alkynyl, cycloalkyl, cycloalkylalkyl, aryl, aralkyl, heteroaryl, heteroaralkyl, heterocyclyl and heterocyclylalkyl wherein the aliphatic, alicyclic and aromatic groups in $R^1$ are optionally substituted with one or two $R^b$ independently selected from hydroxy, alkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano and further wherein the aromatic or alicyclic ring in $R^b$ is optionally substituted with one, two, or three substituents independently selected from alkyl, alkoxy, halo, haloalkyl, haloalkoxy, cyano, carboxy, and carboxyalkyl;

X is selected from the group consisting of —O—, —$NR^{14}$—, —S—, —SO—, and —$SO_2$—;

$R^3$ is selected from the group consisting of alkyl, haloalkyl, alkenyl, alkynyl, cycloalkyl, cycloalkylalkyl, aryl, aralkyl, heteroaryl, heteroaralkyl, heterocyclyl and heterocyclylalkyl, wherein the aliphatic, alicyclic and aromatic groups in $R^3$ are optionally substituted with one or two $R^c$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano and further wherein the aromatic or alicyclic ring in $R^c$ is optionally substituted with one, two, or three substituents independently selected from alkyl, alkoxy, halo, haloalkyl, haloalkoxy, carboxy, and carboxyalkyl;

Y is selected from the group consisting of —C(O)NH—, —OC(O)NH—, —$NR^{14}$—C(O)NH— and —$NR^{14}$C(O)O—. For each of X and Y, each $R^{14}$ when present is independently selected from hydrogen and alkyl, wherein the alkyl is optionally substituted with halo, hydroxy, alkoxy, amino, monosubstituted amino, disubstituted amino, aryl, heteroaryl or heterocyclyl, and wherein each aryl, heteroaryl and heterocyclyl is optionally substituted with one, two or three substituents independently selected from halo and alkyl;

$R^2$ is selected from the group consisting of heteroaryl and —CO-(fused heterocyclyl) ring wherein the heteroaryl and fused heterocyclyl rings are optionally substituted with one, two, three, or four $R^d$ independently selected from hydrogen, alkyl, cycloalkyl, alkenyl, alkynyl, alkylthio, hydroxy, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, amino, monosubstituted amino, and disubstituted amino, or when two $R^d$ are on adjacent carbon atoms they together with the carbon atoms to which they are attached form a four, five or six membered heterocyclyl ring containing one or two heteroatoms selected from nitrogen, oxygen, sulfur, and —$SO_2$— wherein the heterocyclyl ring is optionally substituted with one or two alkyl; and further wherein any aromatic or alicyclic ring in $R^d$ is optionally substituted with one, two, or three $R^e$ independently selected from alkyl, alkylcarbonylamino, alkoxycarbonylamino, cycloalkyl, cycloalkylalkyl, cycloalkoxycarbonylamino, cycloalkylalkyloxycarbonylamino, nitro, alkoxy, cycloalkyloxy, aryloxy, heteroaryloxy, halo, haloalkyl, haloalkoxy, hydroxyl, carboxy, alkoxycarbonyl, amino, monosubstituted amino, disubstituted amino, acylamino, and ureido wherein cycloalkyl and cycloalkylalkyl in $R^e$ are optionally substituted with one, two or three alkyl; and $R^4$ is selected from the group consisting of alkyl, cycloalkyl, cycloalkylalkyl, aryl, aralkyl, heteroaryl, heteroaralkyl, heterocyclyl, and heterocyclylalkyl; wherein any aromatic or alicyclic ring in $R^4$ is optionally substituted with one, two, or three $R^f$ independently selected from alkyl, alkoxy, halo, haloalkyl, haloalkoxy, cyano, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, and disubstituted amino wherein the aromatic or alicyclic ring in $R^f$ is optionally substituted with one, two, or three substituents independently selected from alkyl, alkoxy, halo, haloalkyl, haloalkoxy, hydroxy, carboxy, alkoxycarbonyl, monosubstituted amino, disubstituted amino, and acylamino; or the pharmaceutically acceptable salts thereof.

For the sake of clarity, it is pointed out that the point of attachment of the Y groups to the $R^4$ group is as follows: $R^4C(O)NH$—, $R^4OC(O)NH$—, $R^4NR^{14}$—C(O)NH—, or $R^4NR^{14}C(O)O$—.

In a second aspect, this invention is directed to a method of inhibiting Cathepsin B activity in a mammal, comprising administering to a mammal a therapeutically effective amount of a compound of Formula (I), or the pharmaceutically acceptable salts thereof, in admixture with one or more pharmaceutically acceptable excipients.

In a third aspect, the invention is directed to a method of treating a subject diagnosed with both HCV and fibrosis comprising administering to said mammal an effective amount of a compound of Formula (I) suitable to treat both HCV and fibrosis: In particular, the fibrosis condition is liver fibrosis. The method of treatment is also useful for treating a subject affirmatively diagnosed with both HCV and liver fibrosis, or a subject at risk of acquiring both HCV and liver fibrosis.

DETAILED DESCRIPTION OF THE INVENTION

Definitions

Figure 1:
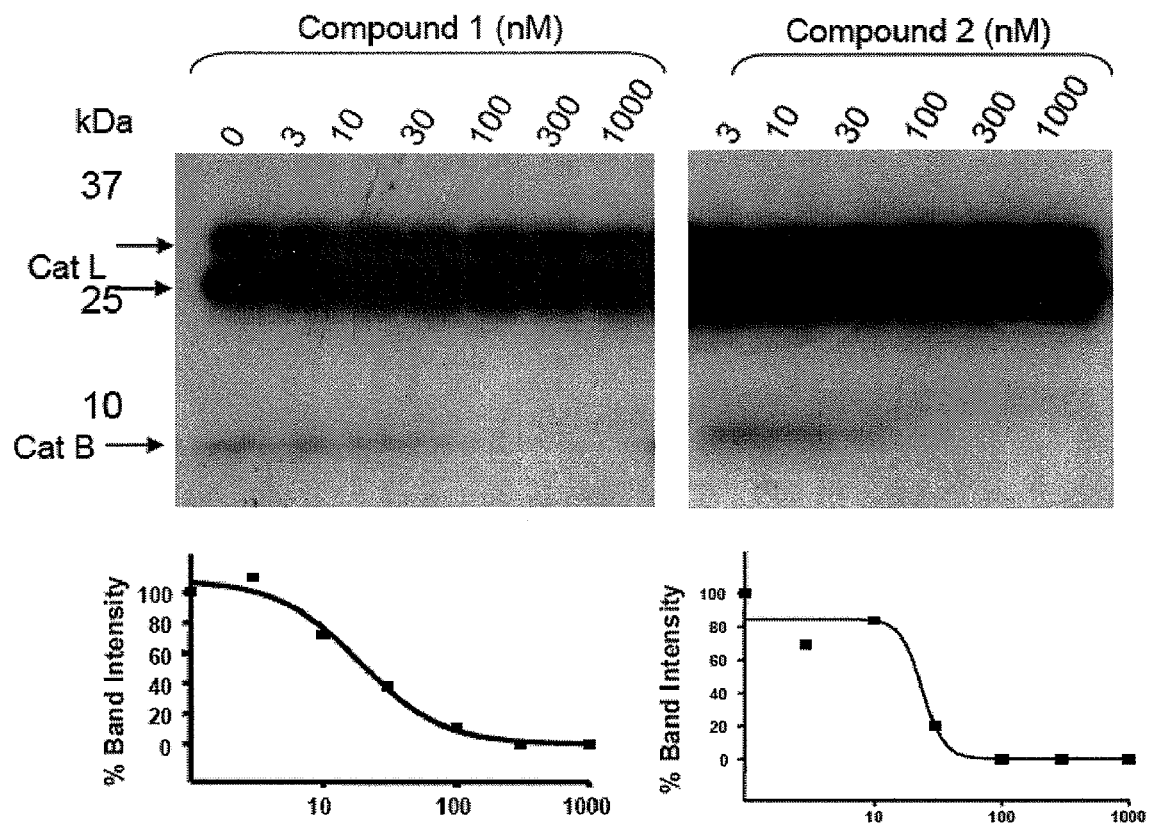
FIG. 1 shows a measure of the potency of the compounds identified as Compound 1 and Compound 2 in a cellular activity-based probe assay.

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl and heterocyclyl rings as defined herein.

"Aliphatic" means alkyl, alkenyl, or alkynyl radicals as defined herein

"Alkyl" represented by itself means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Alkylcarbonylamino" refers to a —NHC(O)R radical where R is an alkyl group as defined above e.g., methylcarbonylamino, ethylcarbonylamino, and the like.

"Alkylene", unless indicated otherwise, means a straight or branched, saturated aliphatic, divalent radical having the number of one to six carbon atoms, e.g., methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-methyltetramethylene (—CH$_2$CH(CH$_3$)CH$_2$CH$_2$—), pentamethylene (—CH$_2$CH$_2$CH$_2$CH$_2$CH$_2$—), and the like.

"Alkenyl" means a linear monovalent hydrocarbon radical of two to six carbon atoms or a branched monovalent hydrocarbon radical of three to six carbon atoms containing one or two double bonds e.g., ethenyl, propenyl (including all isomeric forms), 1-methylpropenyl, butenyl (including all isomeric forms), or pentenyl (including all isomeric forms), and the like.

"Alkenyloxycarbonyl" refers to a —C(O)OR radical where R is an alkenyl group as defined above e.g., 3-propen-1-yloxycarbonyl, and the like.

"Alkenylaminocarbonyl" refers to a —C(O)NHR radical where R is an alkenyl group as defined above e.g., 3-propen-1-ylaminocarbonyl, and the like.

"Alkynyl" means a linear monovalent hydrocarbon radical of two to six carbon atoms or a branched monovalent hydrocarbon radical of three to six carbon atoms containing one or two triple bonds e.g., ethynyl, propynyl (including all isomeric forms), 1-methylpropynyl, butynyl (including all isomeric forms), or pentynyl (including all isomeric forms), and the like.

"Alkynyloxycarbonyl" refers to a —C(O)OR radical where R is an alkynyl group as defined above e.g., 3-propyn-1-yloxycarbonyl, and the like.

"Alkylthio" means an —SR radical where R is alkyl as defined herein, e.g., methylthio, ethylthio, propylthio, or butylthio, and the like.

"Alkylsulfonyl" means —SO$_2$R radical where R is alkyl as defined herein e.g., methylsulfonyl, ethylsulfonyl, and the like.

"Alkoxy" refers to a —OR radical where R is an alkyl group as defined above e.g., methoxy, ethoxy, and the like.

"Alkoxycarbonylamino" refers to a —NHC(O)OR radical where R is an alkyl group as defined above e.g., methoxycarbonylamino, ethoxycarbonylamino, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxy-ethyl, 1-, 2-, or 3-methoxypropyl, 2-ethoxyethyl, and the like.

"Alkoxycarbonyl" refers to a —C(O)OR radical where R is an alkyl group as defined above e.g., methoxycarbonyl, ethoxycarbonyl, and the like.

"Amino" means a —NH$_2$ radical.

"Alkylamino" means a radical —NHR where R is alkyl as defined herein, e.g., methylamino, ethylamino, n-, iso-propylamino, n-, iso-, tert-butylamino, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, acyl, hydroxyalkyl, alkoxyalkyl, aryl, aralkyl, heteroaryl, heteroaralkyl or heterocyclylalkyl and R' is hydrogen, alkyl, hydroxyalkyl, alkoxyalkyl, aryl, aralkyl, heteroaryl, heteroaralkyl, heterocyclylalkyl, cycloalkyl, cycloalkylalkyl, aminocarbonyl, or aminosulfonyl as defined herein e.g., aminomethyl, methylaminoethyl, dimethylaminoethyl, 1,3-diaminopropyl, acetylaminopropyl, and the like.

"Acyl" refers to a —COR radical where R is hydrogen, alkyl, haloalkyl, cycloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like. When R is alkyl it is referred to in this application as alkylcarbonyl. When R is aryl it is referred to in this application as arylcarbonyl. When R is heteroaryl it is referred to in this application as heteroarylcarbonyl. When R is heterocyclyl it is referred to in this application as heterocyclylcarbonyl.

"Acylamino" refers to a —NRCOR' radical where R is hydrogen or alkyl and R' is hydrogen, alkyl, haloalkyl, cycloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Aminocarbonyl" means —CONRR' radical where R and R' are independently selected from hydrogen, alkyl, aryl, aralkyl, heteroaryl, heteroaralkyl, or heterocyclylalkyl or R and R' together with the nitrogen atom to which they are attached form heterocycloamino as defined herein.

"Aminosulfonyl" means —SO$_2$NRR' radical where R and R' are independently selected from hydrogen, alkyl, aryl, aralkyl, heteroaryl, heteroaralkyl, or heterocyclylalkyl or R and R' together with the nitrogen atom to which they are attached form heterocycloamino as defined herein.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp$^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aryloxy" refers to a —O—R radical where R is aryl as defined above e.g., phenoxy, napthyloxy, and the like.

"Aryloxycarbonyl" refers to a —C(O)OR radical where R is aryl as defined above e.g., phenyloxycarbonyl, naphthyloxycarbonyl, and the like.

"Aralkyl" refers to a -(alkylene)-R radical where R is aryl as defined above e.g., benzyl, phenethyl, and the like.

"Arylthio" means an —SR radical where R is aryl as defined herein, e.g., phenylthio or naphthylthio.

"Arylsulfonyl" means an —SO$_2$R radical where R is aryl as defined herein, e.g., phenylsulfonyl or naphthylsulfonyl.

"Carboxy" refers to —C(O)OH radical.

"Carboxyalkyl" means an alkyl radical, as defined herein, substituted with at least one, preferably one or two, —C(O)OH group(s), e.g., carboxymethyl, carboxyethyl, 1-, 2-, or 3-carboxypropyl, and the like.

"Cycloalkyl" refers to a monovalent saturated monocyclic ring containing three to eight ring carbon atoms e.g., cyclopropyl, cyclobutyl, cyclopentyl, cyclohexyl, and the like.

"Cycloalkylalkyl" refers to a -(alkylene)-R radical where R is cycloalkyl as defined above e.g., cyclopropylmethyl, cyclobutylethyl, cyclobutylmethyl, and the like.

"Cycloalkyloxy" refers to a —OR radical where R is cycloalkyl as defined above e.g., cyclopropyloxy, cyclopentyloxy, cyclohexyloxy, and the like.

"Cycloalkyloxycarbonylamino" refers to a —NHC(O)OR radical where R is cycloalkyl as defined above e.g., cyclopropyloxycarbonylamino, cyclopentyloxycarbonylamino, and the like.

"Cycloalkylalkyloxycarbonylamino" refers to a —NHC(O)OR radical where R is cycloalkylalkyl as defined above e.g., cyclopropylmethyloxycarbonylamino, cyclopentylmethyloxycarbonylamino, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Dialkylamino" means a radical —NRR' where R and R' are independently alkyl as defined herein, e.g., dimethylamino, diethylamino, N,N-methylpropylamino or N,N-methylethylamino, and the like.

"Disubstituted amino" means a radical —NRR' where R and R' are independently selected from alkyl, cycloalkyl, cycloalkylalkyl, hydroxyalkyl, alkoxyalkyl, aminoalkyl, aryl, aralkyl, heteroaryl, or heteroaralkyl as defined herein, e.g., dimethylamino, diethylamino, N,N-methylpropylamino or N,N-methylethylamino, methylphenylamino, and the like. Dialkylamino is a subgroup of disubstituted amino.

"Fused heterocyclyl" means heterocyclyl radical as defined herein that is fused to an aryl or heteroaryl ring as defined herein e.g., 2,3-dihydroisoindol-1-yl, 1,2,3,4-tetrahydroisoquinolin-1-yl, and the like.

"Halo" refers to fluoro, chloro, bromo or iodo.

"Haloalkyl" refers to alkyl as defined above substituted by one or more, preferably one to seven, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or bicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothiophenyl, benzimidazolyl, quinolinyl, isoquinolinyl, quinazolinyl, quinoxalinyl, pyrazolyl, thienopyridinyl, for example thieno[3,2-b]pyridinyl, thieno[2,3-b]pyridinyl, and the like, thienopyrimidinyl, for example thieno[3,2-d]pyrimidinyl or thieno [2,3-d]pyrimidinyl, and the like.

"Heteroaryloxy" refers to a —O—R radical where R is heteroaryl as defined above e.g., furanyloxy, pyridinyloxy, indolyloxy, and the like.

"Heteroaryloxycarbonyl" refers to a —C(O)O—R radical where R is heteroaryl as defined above e.g., pyridinyloxycarbonyl, pyrimidinyloxycarbonyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaralkyloxycarbonyl" refers to a —C(O)O—R radical where R is heteroaralkyl as defined above e.g., pyridinylmethyloxycarbonyl, pyrimidinylmethyloxycarbonyl, and the like.

"Heteroarylthio" means an —SR radical where R is heteroaryl as defined herein, e.g., pyridinylthio, furanylthio, thienylthio, and the like.

"Heteroarysulfonyl" means an —SO$_2$R radical where R is heteroaryl as defined herein, e.g., pyridinylsulfonyl, thienylsulfonyl, and the like.

"Heterocyclyl" refers to a saturated or partially unsaturated, mono or bicyclic radical of 4, 5, 6, or 7 carbon ring atoms wherein one or more, preferably one, two, or three of the ring carbon atoms are replaced by a heteroatom selected from —N=, —N—, —O—, —S—, —SO—, or —S(O)$_2$— and further wherein one or two ring carbon atoms are optionally replaced by a keto (—CO—) group. The heterocyclyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydrofuranyl, tetrahydropyranyl, tetrahydrothiopyranyl, 1-oxo-tetrahydrothiopyranyl, 1,1-dioxotetrathio-pyranyl, indolinyl, piperazinyl, piperidyl, pyrrolidinyl, pyrrolinyl, quinuclidinyl,3,4-dihydroisoquinolinyl, dihydroindolyl, and the like. When the heterocyclyl group contains at least one nitrogen ring atom it is referred to herein as "heterocycloamino" and is a subset of the heterocyclyl group as defined above.

"Heterocyclylalkyl" refers to a -(alkylene)-R radical where R is heterocyclyl as defined above e.g., pyrrolidinylmethyl, tetrahydrofuranylethyl, pyridinylmethylpiperidinylmethyl, and the like.

"Heterocyclyloxycarbonyl" refers to a —C(O)OR radical where R is heterocyclyl as defined above e.g., piperidinyloxycarbonyl, tetrahydrofuranoxycarbonyl, and the like.

"Heterocyclylsulfonyl" means an —SO$_2$R radical where R is heterocyclyl as defined herein, e.g., piperidin-1-ylsulfonyl, pyrrolidin-1-ylsulfonyl, and the like.

"Hydroxy" means —OH radical.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to encompass all possible stereoisomers.

"Monosubstituted amino" means a radical —NHR where R is selected from alkyl, cycloalkyl, cycloalkylalkyl, hydroxyalkyl, alkoxyalkyl, aminoalkyl, aryl, aralkyl, heteroaryl, or heteroarylalkyl as defined herein, e.g., methylamino, ethylamino, propylamino, phenylamino, benzylamino, and the like.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example, an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-βb-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates. It is understood that the names and illustration used in this Application to describe compounds of Formula (I) are meant to be encompassed all possible prodrugs thereof.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active Cathepsin S inhibitors. A comprehensive list of suitable protecting groups can be found in T. W. Greene, *Protective Groups in Organic Synthesis*, 3rd edition, John Wiley & Sons, Inc. 1999. It is understood that the names and illustration used in this Application to describe compounds of Formula (I) are meant to be encompassed all possible protected derivatives thereof.

"Therapeutically effective amount" means that amount which, when administered to an animal for treating a disease, is sufficient to effect such treatment for the disease.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Ureido" means a radical —NHCONRR' where R is hydrogen or alkyl and R' is hydrogen, alkyl, cycloalkyl, or cycloalkylalkyl.

The names of the compounds of the invention were generated by ChemBioDraw Ultra, Version 11.

As described above, the compounds of Formula (I) are useful for treating both HCV and disease states mediated by Cathepsin B in a mammal, particularly human subjects. It should be noted that as a result of inflammation and liver injury, chronic HCV infection can lead to progressive liver fibrosis and eventually cirrhosis, and patients with HCV are at risk for developing progressive fibrotic liver disease. Compounds that inhibit HCV virus replication would therefore inhibit further fibrosis of the liver. However, such compounds would not treat the fibrosis itself but only reduce a source of further liver injury, whereas the compounds of the invention, by virtue of their ability to inhibit Cathepsin B activity, not only inhibit HCV but also reverse or reduce in severity the existing fibrosis of the liver previously induced by the associated HCV infection, and this is clearly advantageous. The compounds of the invention, by virtue of their ability to inhibit Cathepsin B and unlike compounds that inhibit only HCV viral replication, would also be advantageous in the treatment of liver fibrosis not associated with HCV infection but associated with other chronic liver injuries such as, but not limited to, hepatic steatosis. It should also be noted that the compounds of the invention are useful not only for treating subjects affirmatively diagnosed with HCV and fibrosis of the liver but also subjects that are considered at risk for the development of liver fibrosis by means of a genetic marker or biochemical surrogate marker of fibrosis.

Preferred Embodiments of the Invention

In one embodiment, the invention relates to a method of inhibiting Cathepsin B activity in a mammal comprising administering a therapeutically effective amount of a compound of Formula (I), particularly those compounds of Formula (I) in which $R^2$ is heteroaryl, including those where $R^2$ is a 9 or 10 membered bicyclic heteroaryl group containing 1, 2, or 3 hetero atoms selected from nitrogen, oxygen, and sulfur, especially where the bicyclic rings are optionally substituted with alkyl, alkoxy, or heteroaryl.

Within the group, a preferred subgroup includes those compounds in which E is —C(O)C(O)NR$^5$R$^6$, particularly where $R^5$ is hydrogen and $R^6$ is alkyl or cycloalkyl, especially where $R^6$ is cyclopropyl or cyclobutyl.

A second preferred subgroup includes those compounds in which $R^1$ is hydrogen, alkyl, cycloalkyl, or cycloalkylalkyl, particularly where $R^1$ is methyl, ethyl, n-propyl, isopropyl, n-butyl, isobutyl, tert-butyl, cyclopropyl, cyclopropylmethyl, cyclobutyl, or cyclobutylmethyl.

A third preferred subgroup includes those compounds in which $R^3$ is hydrogen, alkyl, cycloalkyl, or cycloalkylalkyl, particularly where $R^3$ is methyl, ethyl, n-propyl, isopropyl, n-butyl, isobutyl, or tert-butyl.

A fourth preferred subgroup includes those compounds in which X is oxygen and Y is —NR$^{14}$C(O)NH—, particularly where $R^{14}$ is hydrogen.

A fifth preferred subgroup includes those compounds in which $R^4$ is alkyl, cycloalkyl, or cycloalkylalkyl, particularly where $R^4$ is methyl, ethyl, n-propyl, isopropyl, n-butyl, isobutyl, tert-butyl, cyclopropyl, cyclopropylmethyl, cyclobutyl, or cyclobutylmethyl, especially where $R^4$ is tert-butyl.

In a second aspect, the invention is directed to a method of treating a subject diagnosed with both HCV and fibrosis comprising administering to said mammal an effective amount of a compound of Formula (I) suitable to treat both HCV and fibrosis: In particular, the fibrosis condition is liver fibrosis. The method of treatment is also useful for treating a subject affirmatively diagnosed with both HCV and liver fibrosis, or a subject at risk of acquiring both HCV and liver fibrosis. In preferred embodiments, the compounds of Formula (I) are selected from the embodiments identified above as preferred embodiments.

At the present, particularly preferred compounds include:
(2S,4R)-1-((S)-2-(3-tert-Butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(6-methoxyisoquinolin-1-yloxy)-pyrrolidine-2-carboxamide;
(2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-methoxyisoquinolin-1-yloxy)-pyrrolidine-2-carboxamide;
(2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-ethoxyisoquinolin-1-yloxy)-pyrrolidine-2-carboxamide;
(2S,4R)-1-((S)-2-(3-tert-Butylureido)-3,3-dimethylbutanoyl)-N-((S)-1-(cyclopropylamino)-1,2-dioxohexan-3-yl)-4-(6-ethoxyisoquinolin-1-yloxy)-pyrrolidine-2-carboxamide;
(2S,4R)-1-((S)-2-(3-tert-Butylureido)-3,3-dimethylbutanoyl)-N-((S)-1-cyclopropylamino)-1,2-dioxoheptan-3-yl)-4-(6-methoxyisoquinolin-1-yloxy)-pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(6-methoxy-3-methylisoquinolin-1-yloxy)-pyrrolidine-2-carboxamide;
(2S,4R)-1-((S)-2-(3-tert-Butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(2-(pyridin-2-yl)thieno[3,2-d]pyrimidin-4-yloxy)pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(5-(pyridin-2-yl)thieno[3,2-b]pyridin-7-yloxy)pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(2-(pyridin-2-yl)thieno[2,3-d]pyrimidin-4-yloxy)pyrrolidine-2-carboxamide;
(2S,4R)-1-((S)-2-(3-tert-Butylureido)-3,3-dimethylbutanoyl)-N-((S)-1-cyclopropylamino)-1,2-dioxohexan-3-yl)-4-(2-(1,3-dimethyl-1H-pyrazol-5-yl)thieno[3,2-d]pyrimidin-4-yloxy)pyrrolidine-2-carboxamide;
(2S,4R)-N-((S)-1-(cyclopropylamino)-1,2-dioxohexan-3-yl)-1-((S)-2-(3-cyclopropylmethyl)ureido)-3,3-dimethylbutanoyl)-4-(7-methoxy-2-(1H-pyrazol-1-yl)quinolin-4-yloxy)pyrrolidine-2-carboxamide; and (2S,4R)-N-((S)-1-(cyclopropylamino)-1,2-dioxohexan-3-yl)-1-((S)-3,3-dimethyl-2-(3-neopentylureido)butanoyl)-4-(7-methoxy-2-(1H-pyrazol-1-yl)quinolin-4-yloxy)pyrrolidine-2-carboxamide.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1999.

Compounds of Formula (I) where Y is —OC(O)NH—, E is —COCONR$^5$R$^6$ and X, R$^1$, R$^2$, R$^3$, and R$^4$ are as defined in the Summary of the Invention can be prepared by proceeding as in the following Reaction Scheme 1 below.

Reaction Scheme 1

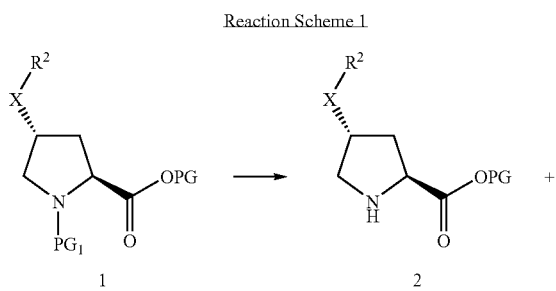

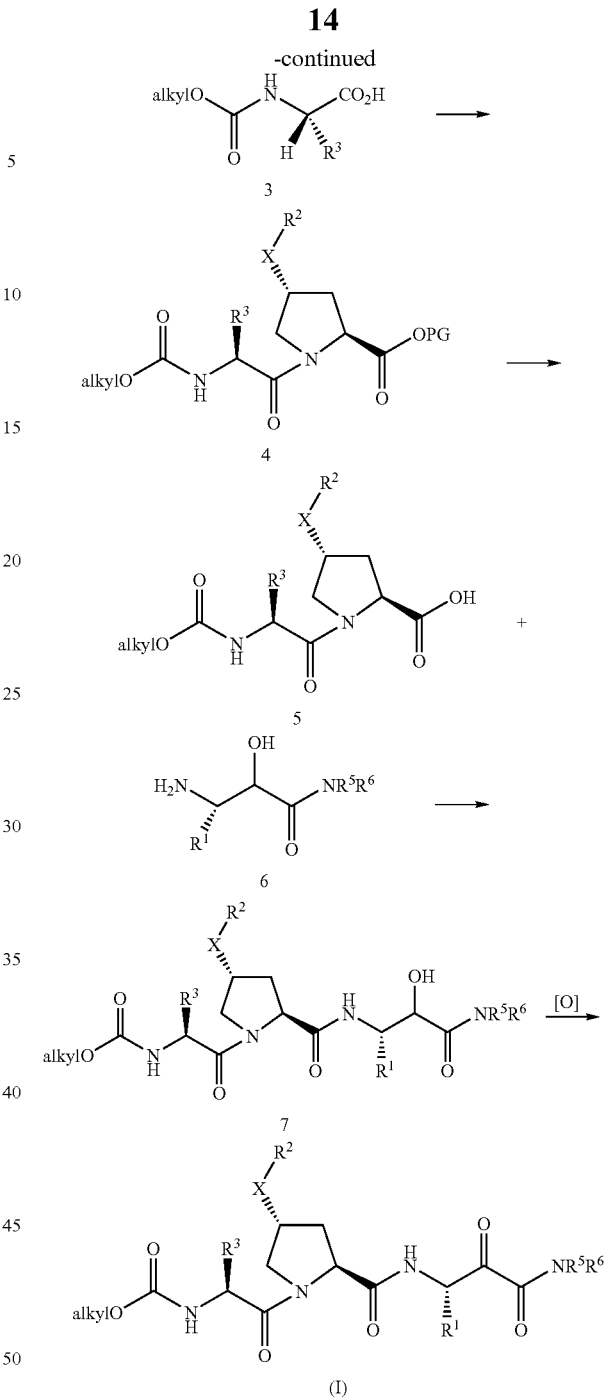

Deprotection of the amino protecting group PG$_1$ such as tert-butoxycarbonyl, benzyloxycarbonyl, and the like, in a pyrrolidine compound of formula 1 where PG is a suitable carboxy protecting group, preferably alkyl, and X and R$^2$ are as defined in the Summary of the Invention provides a compound of formula 2. The reaction conditions employed for the amino protecting group depends on the nature of the protecting group. For example, if PG$_1$ is tert-butoxycarbonyl, it is removed by treatment of 1 with an acid such as hydrochloric acid in an organic solvent such as dioxane, tetrahydrofuran, and the like. Other suitable nitrogen protecting groups with reaction conditions for putting them on and removing them can be found in Greene, T. W.; and Wuts, P. G. M.; *Protecting Groups in Organic Synthesis*; John Wiley & Sons, Inc. 1999.

Compounds of formula 1 can be prepared by methods well known in the art. Some such methods are described in US 2003191067, U.S. Pat. No. 6,608,027, U.S. Pat. No. 6,268,207, U.S. Pat. No. 6,404,397, U.S. Pat. No. 6,268,207, and WO 2005/028501, the disclosures of which are incorporated herein by reference in their entirety.

Treatment of compound 2 with an amino acid of formula 3 where $R^3$ is as defined in the Summary of the Invention under peptidic coupling reaction conditions provides a compound of formula 4 where Y is —O—C(O)NH— and $R^4$ is alkyl. The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxy-benzotriazole (HOBT), and a base such as N,N-diisopropylethylamine, triethylamine, N-methylmorpholine, and the like. The reaction is typically carried out at 20 to 30° C., preferably at about 25° C. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like or mixtures thereof. Amino acids of formula 3 are either commercially available or they can be prepared by methods well known in the art.

Hydrolysis of the ester group in compound 4 (PG=alkyl) under aqueous basic hydrolysis reaction conditions provides a compound of formula 5. The reaction is typically carried out with cesium carbonate, lithium hydroxide, sodium hydroxide, and the like in an aqueous alcohol such as methanol, ethanol, and the like.

Treatment of compound 5 with an α-hydroxyaminocarboxamide of formula 6 under peptidic coupling reaction conditions as described above provides a compound of formula 7. Compounds of formula 6 can be prepared by methods well known in the art some of which are described in details in working examples, References A and B below. Compound 6 can also be prepared from compound 17 (whose synthesis is described in Scheme 3 below). Briefly, after suitable protection of the amino group (for example as the t-Boc carbamate), the ester group of compound 17 is removed under basic hydrolysis reaction conditions to form the corresponding α-hydroxy acid. Treatment of the acid with an amine of formula $NHR^5R^6$ under coupling reaction conditions followed by acid catalyzed hydrolysis of the amine protecting group provides a compound of formula 6.

Alternatively, the above coupling step can be carried out by first converting 5 into an active acid derivative such as acid halide, succinimide ester, and the like, and then reacting it with an α-hydroxyketoamide of formula 6. The conditions utilized in this reaction depend on the nature of the active acid derivative. For example, if it is an acid chloride derivative of 5, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof. Oxidation of the hydroxy group in compound 8 with a suitable oxidizing agent such as Dess Martin Periodinane provides a compound of Formula (I).

Compounds of Formula (I) where Y is —NHC(O)NH—, E is —COCONR⁵R⁶ and X, $R^1$, $R^2$, $R^3$, and $R^4$ are as defined in the Summary of the Invention can be prepared by proceeding as in the following Reaction Scheme 2 below.

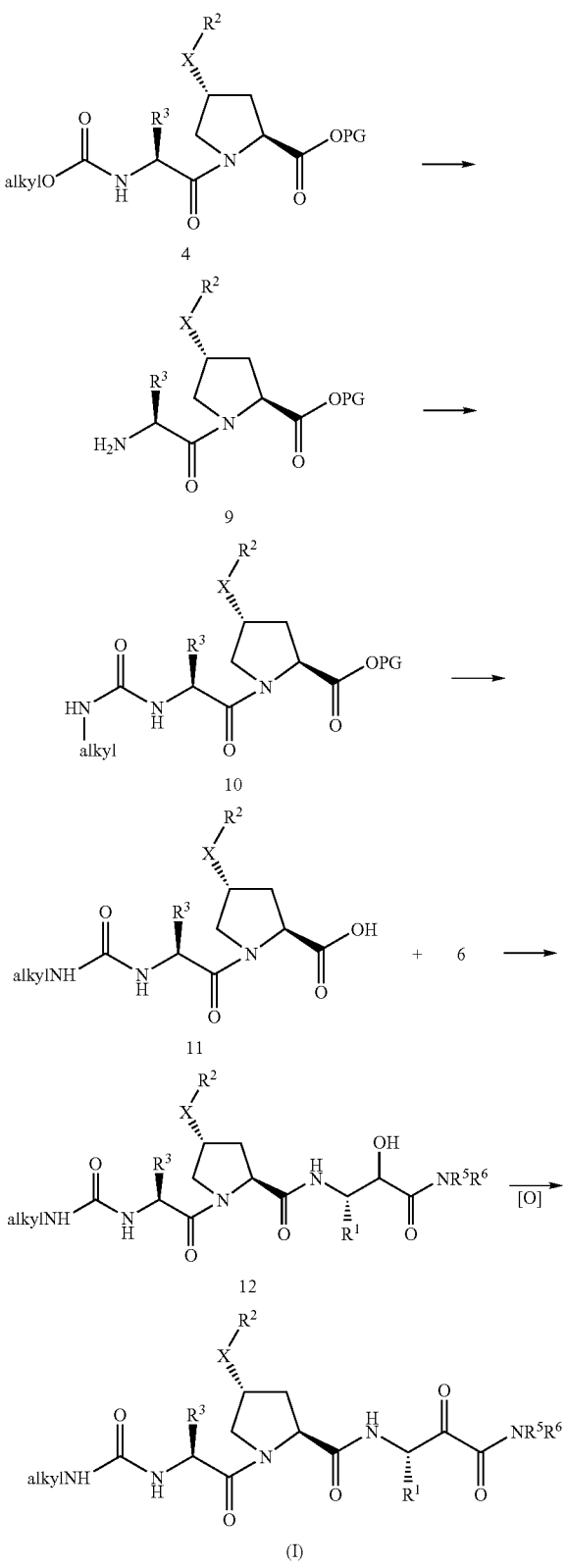

Removal of the Boc group in compound 4 under acid hydrolysis reaction conditions provides an amino compound of formula 9 which upon reaction with an alkyl isocyanate provides a ureido compound of formula 10. The reaction is carried out in the presence of an organic base such triethylamine, pyridine, and the like and in a suitable organic solvent such as dichloromethane, and the like. The ureido compounds can also be prepared by other methods well known in the art such as reaction of compound 9 with carbamoyl halides. Compound 10 is then converted to a compound of Formula (I) by proceeding as described in Scheme 1 above. Similarly compounds of Formula (I) where $R^4$ is other than alkyl can be prepared by substituting alkyl isocyanate with aryl-, heteroaryl-, or aralkyl-isocyanates or carbamyl halides.

Similarly, compound of Formula (I) where Y is —CONH— or —SO$_2$NH— can be prepared by reacting compound 9 with an acylating agent or formula $R^4COL$ respectively under conditions well known in the art.

Alternatively, compounds of Formula (I) can be prepared from compound 4 by deprotecting the acid protecting group to give the corresponding acid. The acid is reacted with the α-hydroxyaminocarboxamide 6 followed by removal of the Boc [alkylOC(O)—] group in the resulting product to give the free amino compound. Reaction of the amino compound with alkyl isocyanates or carbamyl halide gives compound 12 which is then converted to compound of Formula (I) upon oxidation of the hydroxyl group as described above.

Compounds of Formula (I) where E is —COCOOR$^{10}$ and X, Y, R$^1$, R$^2$, R$^3$, R$^4$, and R$^{10}$ are as defined in the Summary of the Invention can be prepared by proceeding as in the following Reaction Scheme 3 below.

Reaction Scheme 3

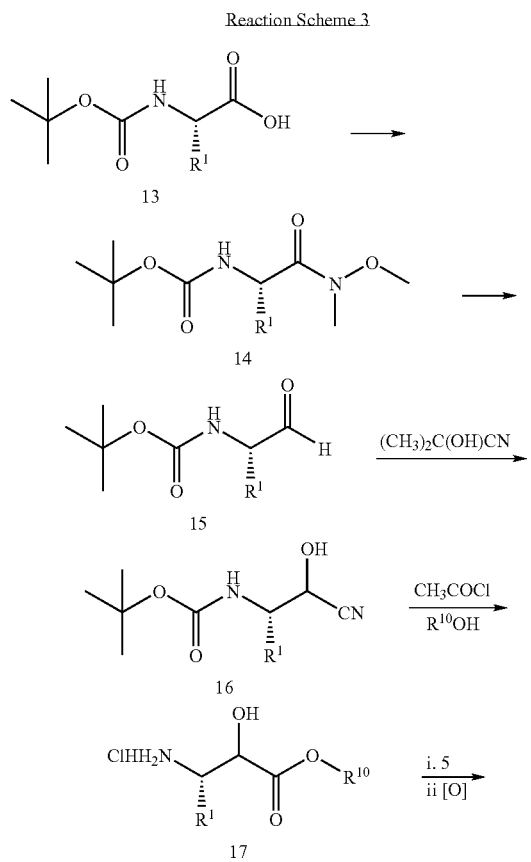

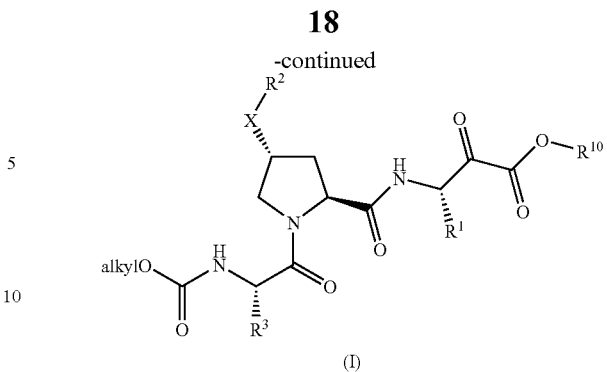

Treatment of a N-Boc-protected amino acid compound of formula 13 with N,O-dimethylamine under conditions well known in the art provides the Weinreb amide compound of formula 14. Compounds of formula 13 can be prepared from commercially available amino acids with tert-butoxycarbonyl anhydride under conditions well known in the art. Other suitable amino protecting groups can be utilized as well. Treatment of compound 14 with a suitable reducing agent such as lithium aluminum hydride in a suitable organic solvent such as tetrahydrofuran, and the like provides the corresponding aldehyde of formula 15. Treatment of compound 15 with acetone cyanohydrin provides compound 16 which is then reacted with acid halide in a hydroxyl compound of formula R$^{10}$OH where R$^{10}$ is as defined in the Summary of the Invention to give the alpha hydroxyl ester compound of formula 17.

Treatment of compound 17 with a compound of formula 5, under peptide coupling conditions as described earlier, followed by oxidation of the hydroxyl group in the resulting product provides a compound of Formula (I) where Y is —OC(O)NH— and R$^4$ is alkyl. Compound of Formula (I) where Y is —OC(O)NH— and R$^4$ is alkyl can be converted to other compounds of Formula (I) where Y and R$^4$ are as defined in the Summary of the Invention as described above.

Compounds of Formula (I) where E is —CONR$^{11}$R$^{12}$ and X, Y, R$^1$, R$^2$, R$^3$, R$^4$, R$^{11}$, and R$^{12}$ are as defined in the Summary of the Invention can be prepared by proceeding as in the following Reaction Scheme 4 below.

Reaction Scheme 4

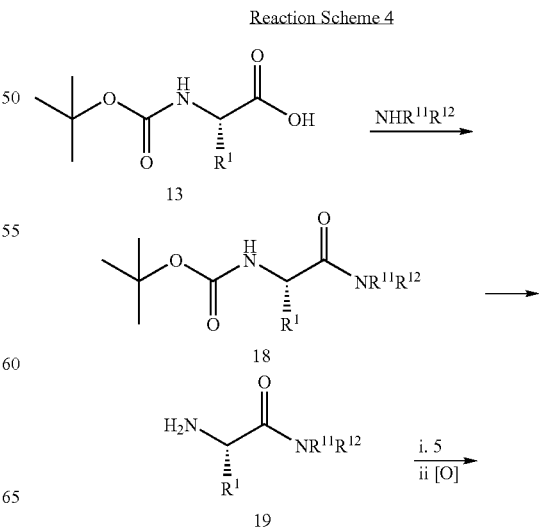

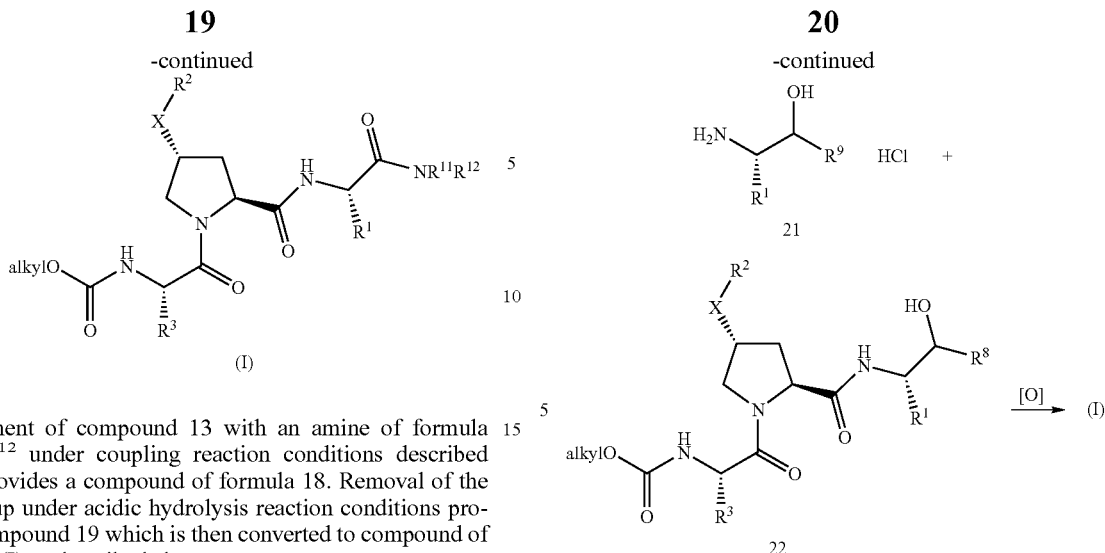

Treatment of compound 13 with an amine of formula NHR[11]R[12] under coupling reaction conditions described above provides a compound of formula 18. Removal of the Boc group under acidic hydrolysis reaction conditions provides compound 19 which is then converted to compound of Formula (I) as described above.

Compounds of Formula (I) where E is —COR[9] and X, Y, R[1], R[2], R[3], R[4], and R[9] are as defined in the Summary of the Invention can be prepared by proceeding as in the following Reaction Scheme 5 below.

Reaction Scheme 5

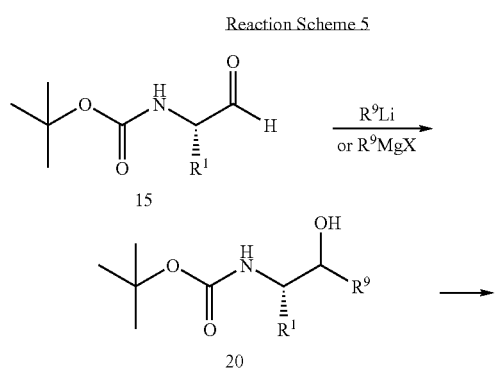

Treatment of a compound of formula 15 with an organolithium or Grignard reagent of formula R[9]Li or R[9]MgX respectively where R[9] is as defined in the Summary of the Invention provides a compound of formula 20. The reaction is typically carried out at low reaction temperatures such as −78° C. and in an organic solvent such as tetrahydrofuran, and the like. Removal of the Boc group provides compound 21 with upon reaction with compound 5 under coupling reaction conditions described above provides a compound of formula 22. Oxidation of the hydroxyl group then provides a compound of Formula (I) where Y is —OC(O)NH— and R[4] is alkyl. Compounds of Formula (I) where Y and R[4] are other groups as defined in the Summary of the Invention can be prepared as described above.

Compounds of Formula (I) where E is —CHO and X, Y, R[1], R[2], R[3], R[4], and R[8] are as defined in the Summary of the Invention can be prepared by proceeding as in the following Reaction Scheme 6 below.

Reaction Scheme 6

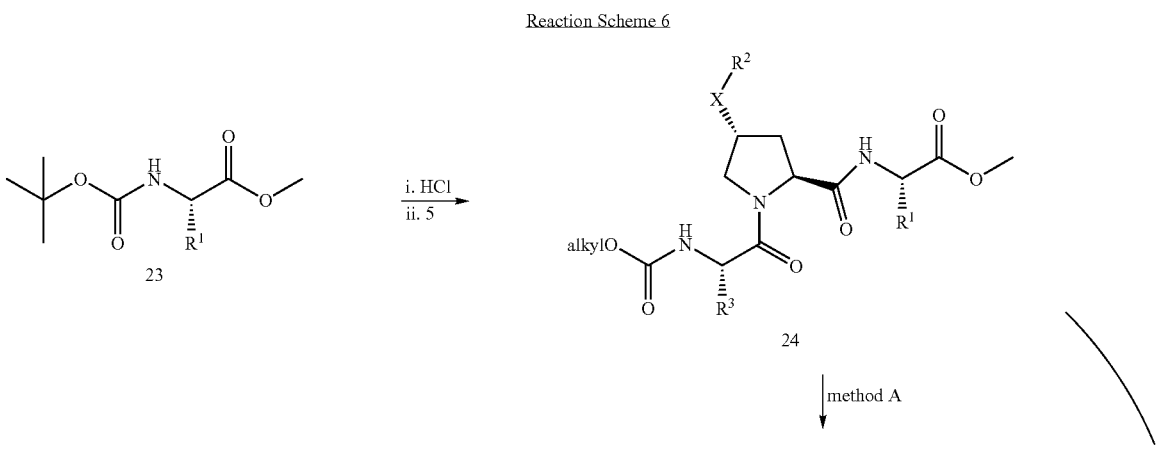

-continued

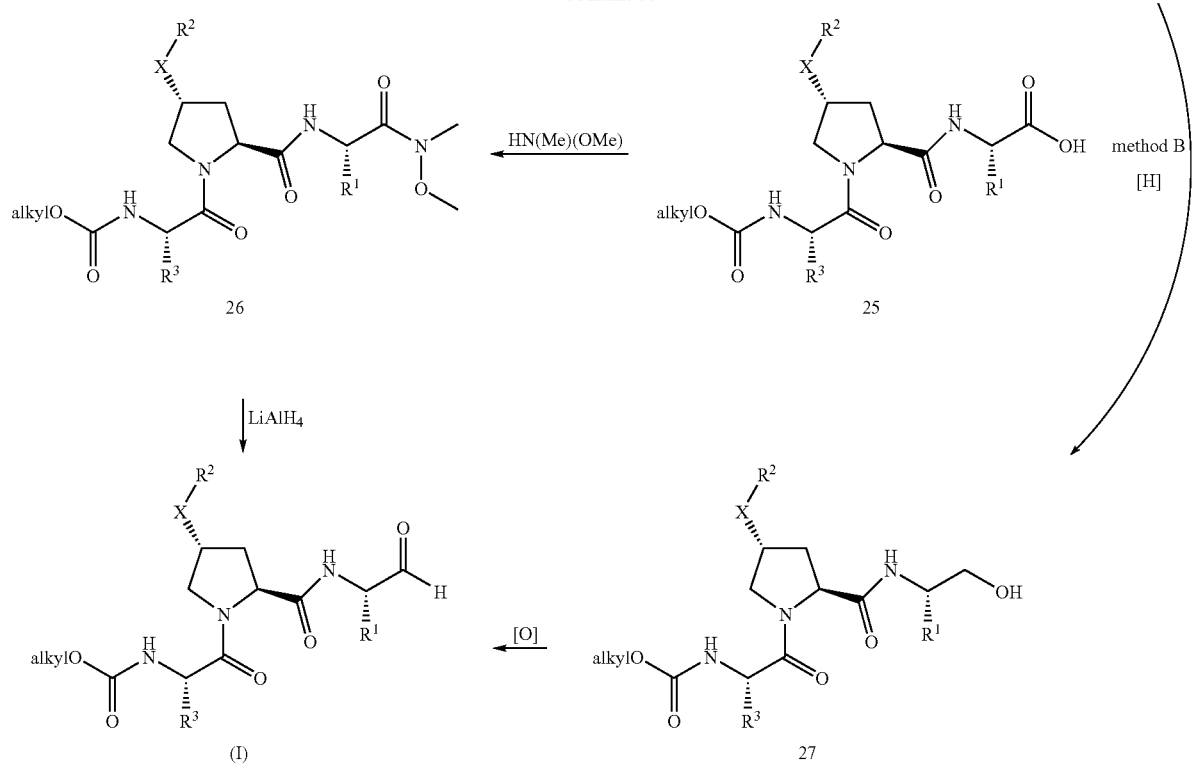

Removal of the amino protecting group in compound 23 under acidic hydrolysis reaction conditions, followed by coupling of the resulting amino compound with a compound of formula 5 provides a compound of formula 24. Compound 24 is then converted to a compound of Formula (I) where E is —CHO by proceeding as shown in method A or B above.

In method A, hydrolysis of the ester group under basic hydrolysis reaction conditions provides a compound of formula 25 which is converted to a Weinreb amide of formula 26. Reduction of the amido group in 26 with a suitable reducing agent such as lithium aluminum hydride then provides a compound of Formula (I) where E is —CHO and Y is —OC(O)NH—.

Alternatively, the ester group in compound 24 can be reduced with a suitable reducing agent such as lithium aluminum hydride to provide the corresponding alcohol of formula 27 which upon treatment with an oxidizing agent provides a compound of Formula (I) where E is —CHO and Y is —OC(O)NH—. Compounds of Formula (I) where Y is other than —OC(O)NH— are prepared as described above.

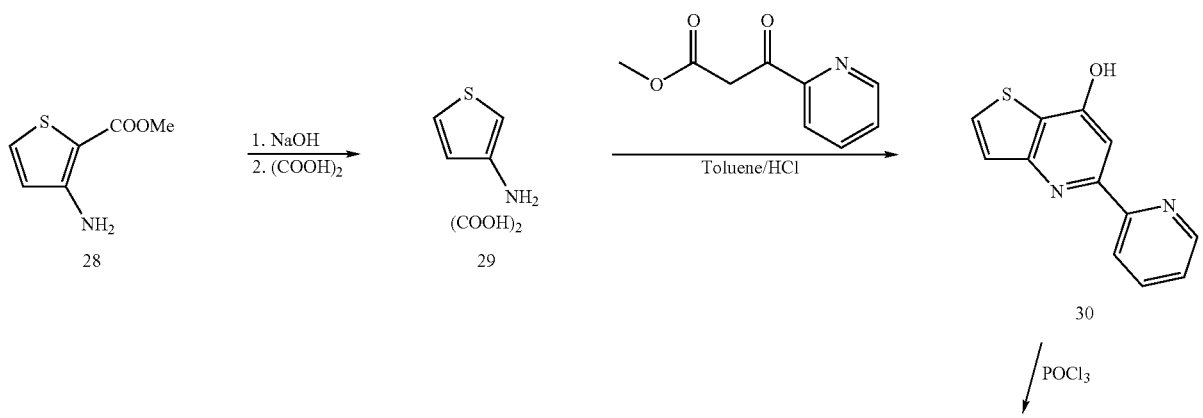

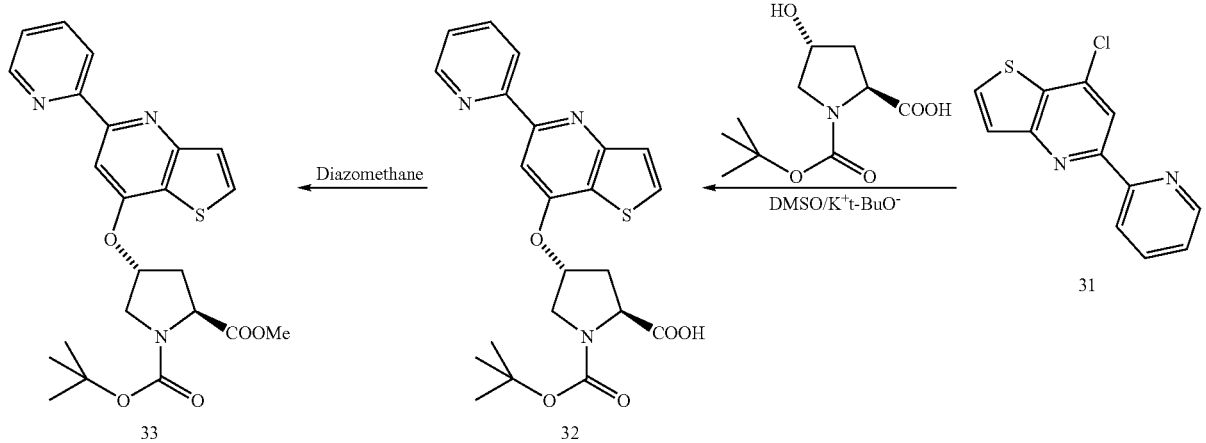

Conversion of 32 or 33 to target compounds can be accomplished using procedures as generally outlined in Example 14 of U.S. Ser. No. 11/478,337, the complete disclosure of which is hereby incorporated by reference.

In a similar manner, Reaction Scheme 8 illustrates the preparation of a heteroaryl substituted pyrimidinothiophene 35 and its conversion to key intermediates 36 and 37.

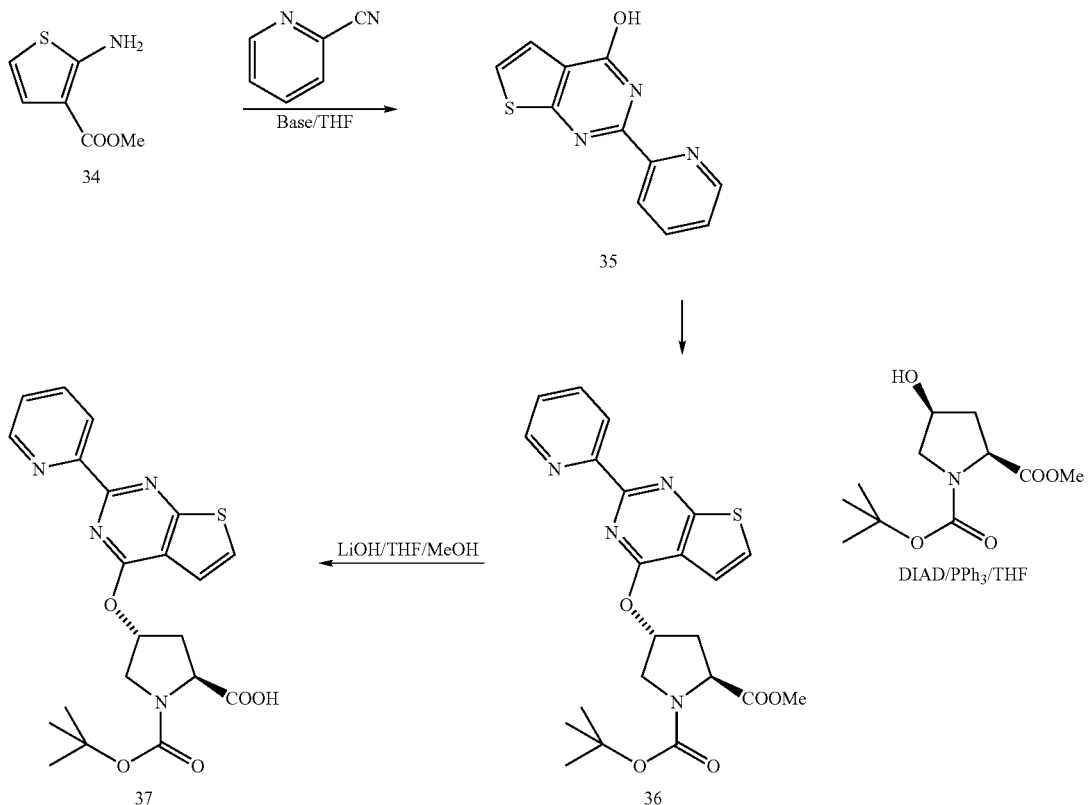

As above, conversion of 37 to target compounds can be accomplished using procedures as generally outlined in Example 14 of U.S. Ser. No. 11/478,337, the complete disclosure of which is hereby incorporated by reference.

A preparation of an isomeric pyrimidinothiophene intermediate is shown in Reaction Scheme 9.
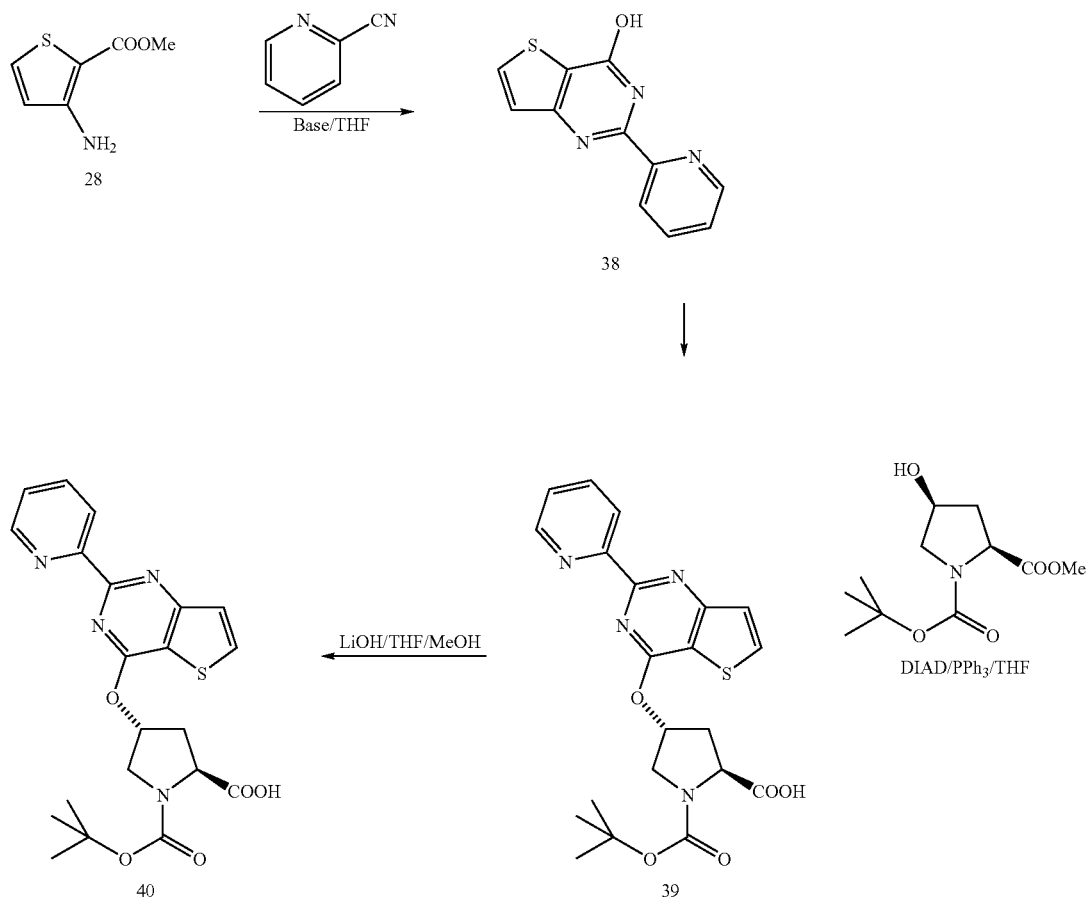
Reaction Scheme 10 illustrates the preparation of a pyrazole-substituted pyrimidinothiophene 44 and its coupling with a proline derivative to form intermediates 45 and 46.
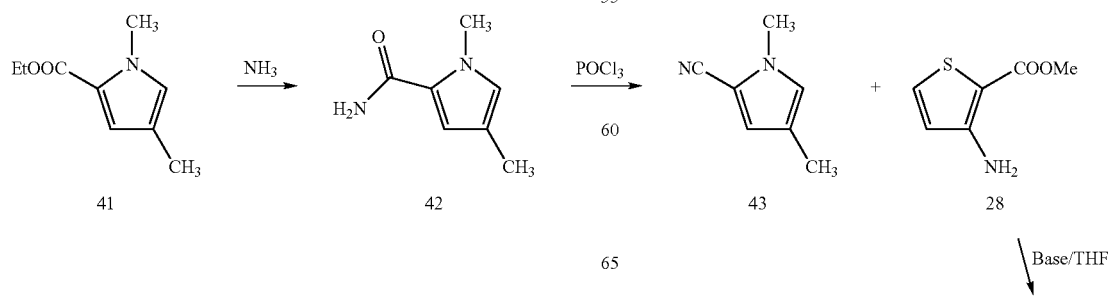

-continued

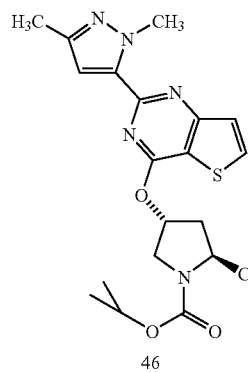 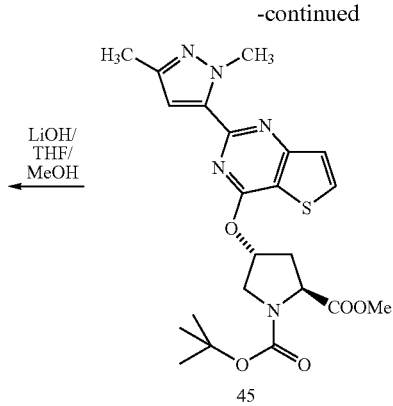 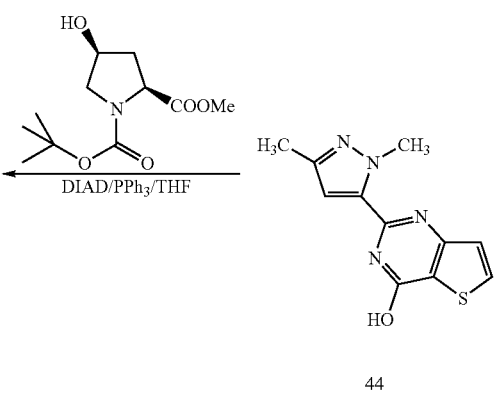

Reaction Scheme 11 shows the preparation of pyridine-substituted pyrimidinothiophene 50, which can be reacted with a proline derivative to form intermediates analogous to 45 and 46 in Scheme 10 for incorporation into the final molecules.

Reaction Scheme 13 shows the preparation of oxazole-substituted pyrimidinothiophene 56, which can be reacted with a proline derivative to form intermediates analogous to 45 and 46 shown in Reaction Scheme 10 for incorporation into the final molecules.

Reaction Scheme 11

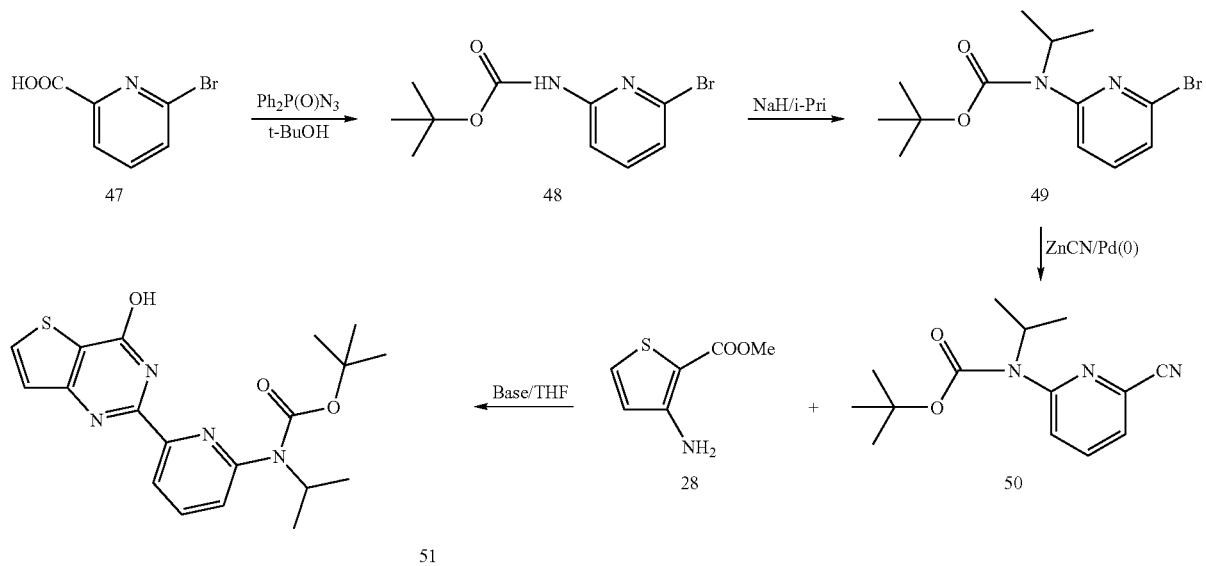

Reaction Scheme 12 shows intermediate 52 which is prepared as in WO 99/24440 and in U.S. Pat. No. 6,492,383 and used for incorporation into the final molecules as shown in Scheme 1.

Reaction Scheme 12

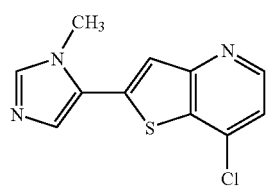

Reaction Scheme 13

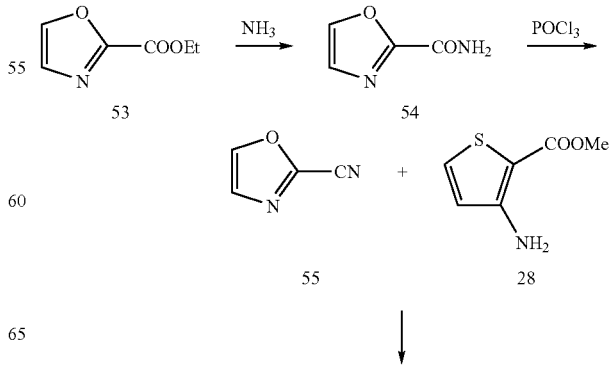

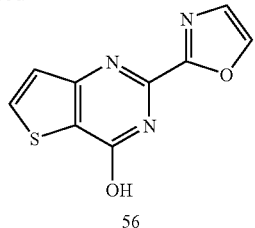
56

A compound of Formula (I) can be converted to other compounds of Formula (I). For example:

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (I). A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as diastereomers that have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure isomer is then recovered by any practical means that would not result in racemization of its chiral centers. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981).

Pharmacology and Utility

The compounds of the present invention are inhibitors of Cathepsin B, a lysosomal cysteine protease, and are therefore useful in treating disease states associated with the normal activity or the increased expression of Cathepsin B, for example tumor invasion, metastasis, Alzheimer's Disease, arthritis, inflammatory diseases such as chronic and acute pancreatitis, inflammatory airway disease, and bone and joint disorders, including osteoporosis, osteoarthritis, rheumatoid arthritis, psoriasis, and other autoimmune disorders, liver fibrosis, including liver fibrosis associated with HCV, all types of steatosis (including non-alcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis and fibrosis/gliosis in the eye, schleroderma, and systemic sclerosis. The compounds of the invention may be used alone, or optionally with one or more antiviral agents.

The inhibitory activities of the compounds of Formula (I) can be determined by methods known to those of ordinary skill in the art. A suitable in vitro assay for measuring the ability of compounds of this invention to inhibit Cathepsin B is set forth in Biological Example 1 infra., and a method of determining inhibition of Cathepsin B in human cells is described in Biological Example 2.

In one embodiment, the compounds of the present invention are particularly useful for treating fibrosis, including liver fibrosis, for example liver fibrosis associated with HCV, and for treating a subject with both HCV and liver fibrosis, or a subject with chronic liver injuries not associated with HCV, such as hepatic steatosis. Such activity is demonstrated by means well known in the art, for example by measuring plasma alanine aminotransferase (ALT) levels and aspartate aminotransferase (AST) in mice with liver damage, then measuring ALT, AST, and liver hydroxyproline levels in mice after administering a compound of the invention. In particular, Biological Example 3 describes such a procedure in more detail, and provides the results of such testing.

There are several other well-established methods of determining whether compounds are effective in reducing liver fibrosis. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (µg/kg) per day to about 100 milligram per kilogram body weight (mg/kg) per day, typically from about 100 µg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 90% w, preferably 5% w to 50% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described below.

EXAMPLES

The present invention is further exemplified, but not limited by, the following examples that illustrate the preparation of compounds of Formula (I) according to the invention.

Reference A

Synthesis of tert-butyl (3S)-1-(cyclopropyamino)-2-hydroxy-1-oxohexan-3-ylcarbamate

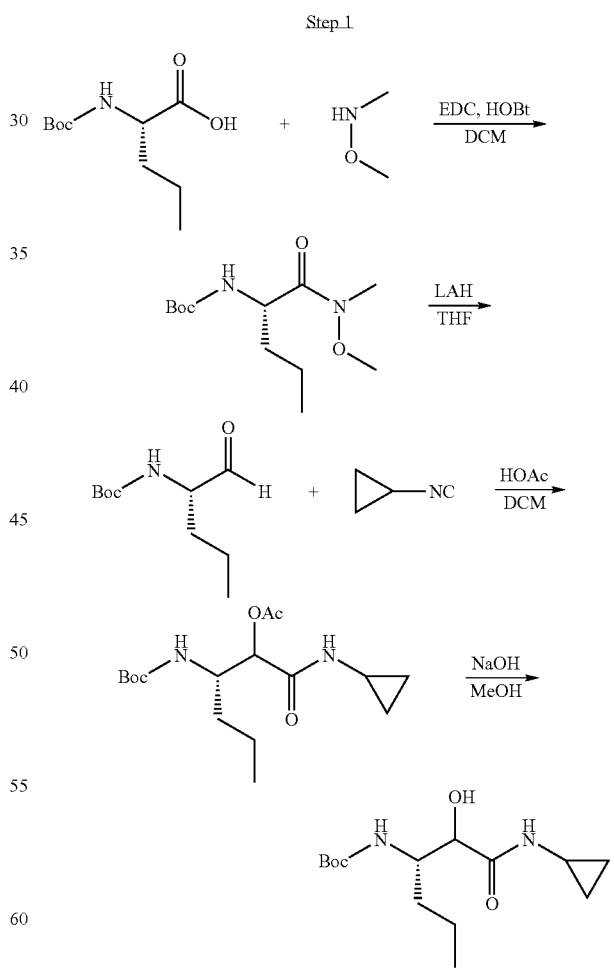

Step 1

To a mixture of Boc-NVa-OH (25 g, 0.115 mol), N,O-dimethylhydroxyamine hydrochloride (12.34 g, 0.127 mol), 1 (3 dimethylaminopropyl)-3 ethylcarbodiimide hydrochloride (EDC) (33.07 g, 0.173 mol), and 1-hydroxybenzotriazole (HOBT) (22.9 g, 0.15 mol) in dichloromethane (300 mL) was slowly added N-methylmorpholine (34.9 g, 0.35 mol) under stirring in 30 minutes. The reaction was left at room temperature for 2 hours, then diluted with 2000 mL ethyl acetate, washed with sodium bicarbonate, water, brine, and dried over magnesium sulfate. The solvent was removed under reduced pressure to give 20 g of (S)-tert-butyl 1-methoxy(methyl) amino)-1-oxopentan-2-ylcarbamate as a colorless oil.

Step 2

To a solution of (S)-tert-butyl 1-methoxy(methyl)amino)-1-oxopentan-2-ylcarbamate (7.2 g, 27.7 mmol) in anhydrous tetrahydrofuran (100 mL) under argon at −78° C., was slowly added lithium aluminum hydride (1M in tetrahydrofuran, 27.7 mL). After 2 hours, the reaction mixture was quenched by slowly adding 1N HCl (20 mL) and then allowed to warm up to room temperature. The reaction mixture was diluted with ethyl acetate (600 mL), washed with 1N HCl, H$_2$O, then brine, and dried over magnesium sulfate. Removal of the solvents under reduced pressure gave (S)-tert-butyl 1-oxopentan-2-ylcarbamate (4.8 g) as an oil.

Step 3

To a solution of cyclopropylisonitrile (1.91 g, 28.5 mmol), (S)-tert-butyl 1-oxopentan-2-ylcarbamate (3.8 g, 19 mmol) in methylene chloride (100 mL) was added acetic acid (2.28 g, 38 mmol) at 0° C. After the addition was complete the reaction mixture was allowed to warm to 25° C. and stirred for 6 hours. The reaction mixture was diluted with ethyl acetate (200 mL), then washed with a saturated solution of sodium bicarbonate and brine (30 mL) and dried over magnesium sulfate. The solvent was removed under reduced pressure, and the crude product was crystallized from 50 mL of ethyl acetate and hexane(v/v=1/1) to give tert-butyl (3S)-1-(cyclopropylamino)-2-hydroxy-1-oxohexan-3-ylcarbamate (4.8 g) as a white solid.

Step 4

Into the solution of tert-butyl (3S)-1-(cyclopropylamino)-2-hydroxy-1-oxohexan-3-ylcarbamate (4.8 g, 14.6 mmol) in methanol (50 mL) was added aqueous sodium hydroxide solution (1N, 22 mL) at room temperature. After 2 hours, methanol was removed under reduced pressure, and the concentrate was extracted with ethyl acetate (300 mL). The ethyl acetate layer was washed with brine and dried over magnesium sulfate. After removal of the solvent under reduced pressure, the residue was crystallized from 100 mL of ethyl acetate and hexane(v/v=3/1) to give tert-butyl (3S)-1-(cyclopropyamino)-2-hydroxy-1-oxohexan-3-ylcarbamate (3.5 g) as a white solid.

Reference B

Synthesis of tert-butyl (2S)-1-cyclobutyl-4-(cyclopropylamino)-3-hydroxy-4-oxobutan-2-ylcarbamate

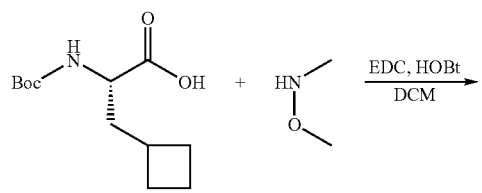

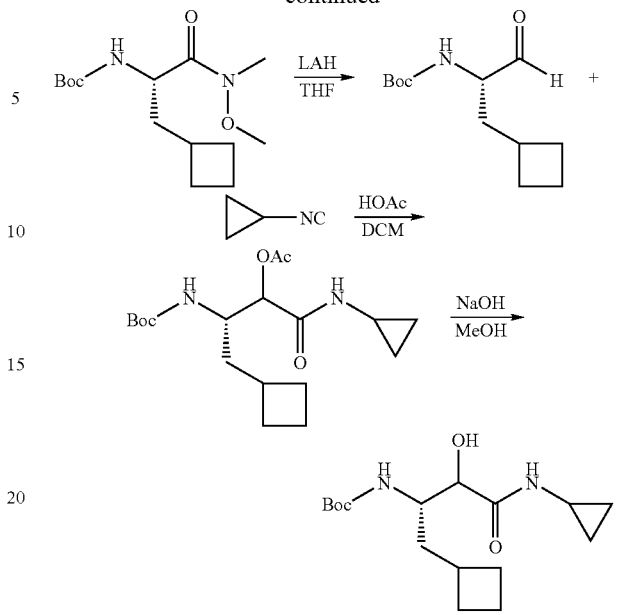

Step 1

To a mixture of the diisopropylamine salt of Boc-L-cyclobutylalanine, (10.33 g, 30 mmol), N,O-dimethylhydroxyamine hydrochloride (3.22 g, 33 mmol), 1 (3 dimethylaminopropyl)-3 ethylcarbodiimide hydrochloride (EDC) (8.63 g, 45 mmol), 1-hydroxybenzotriazole (HOBT) (5.52 g, 36 mmol) in dichloromethane (200 mL), was slowly added N-methylmorpholine (9.11 g, 90 mmol) while stirring over 30 minutes. After 2 hours, the reaction mixture was diluted with ethyl acetate (1000 mL), washed with sodium bicarbonate, water, then brine, and dried over magnesium sulfate. Removal of the solvent under reduced pressure gave (S)-tert-butyl 3-cyclobutyl-1-(methoxy(methyl)amino)-1-oxopropan-2-ylcarbamate (7.1 g) as a colorless oil.

Step 2

To the solution of (S)-tert-butyl 3-cyclobutyl-1-(methoxy (methyl)amino)-1-oxopropan-2-ylcarbamate (4.3 g, 15 mmol) in anhydrous tetrahydrofuran (100 mL) under argon at −78° C., was slowly added lithium aluminum hydride (1M in tetrahydrofuran, 15 mL, 15 mmol). After 2 hours, the reaction mixture was quenched by slowly adding 1N HCl (15 mL) and the reaction mixture was warmed up to room temperature after the addition was complete. The reaction mixture was diluted with ethyl acetate (500 mL), washed with 1N HCl, water, then brine, and dried over magnesium sulfate. Removal of the solvents under reduced pressure gave (S)-tert-butyl 1-cyclobutyl-3-oxopropan-2-ylcarbamate (2.95 g) as an oil.

Step 3

To a solution of cyclopropylisonitrile (1.21 g, 18 mmol), (S)-tert-butyl 1-cyclobutyl-3-oxopropan-2-ylcarbamate (2.95 g, 13 mmol) in methylene chloride(20 mL), was added acetic acid (1.56 g, 26 mmol) at 0° C. After the addition was complete, the reaction mixture was allowed to warm to 25° C. and stirred for another 4 hours. The reaction mixture was diluted with 200 mL ethyl acetate and washed with a saturated solution of sodium bicarbonate, then brine, and dried over magnesium sulfate. The solvent was removed under reduced pressure, and the crude product was crystallized from 50 mL of ethyl acetate and hexane (v/v=1/1) to give (3S)-3-(tert-butoxycarbonylamino)-4-cyclobutyl-1-(cyclopropylamino)-1-oxobutan-2-yl acetate (3.8 g) as a white solid.

Step 4

To a solution of (3S)-3-(tert-butoxycarbonylamino)-4-cyclobutyl-1-(cyclopropylamino)-1-oxobutan-2-yl acetate (3.8 g, 10.7 mmol) in methanol (50 mL) was added sodium hydroxide aqueous solution (1N, 15 mL) at room temperature. After 2 hours, methanol was removed under reduced pressure, and the concentrate was extracted with ethyl acetate. The ethyl acetate was washed with brine and dried over magnesium sulfate. The solvent was removed under reduced pressure, and the residue was crystallized from 100 mL of ethyl acetate and hexane(v/v=3/1) to give tert-butyl (2S)-1-cyclobutyl-4-(cyclopropylamino)-3-hydroxy-4-oxobutan-2-ylcarbamate (2.9 g) as a white solid.

Example 1

Synthesis of (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy)pyrrolidine-2-carboxamide

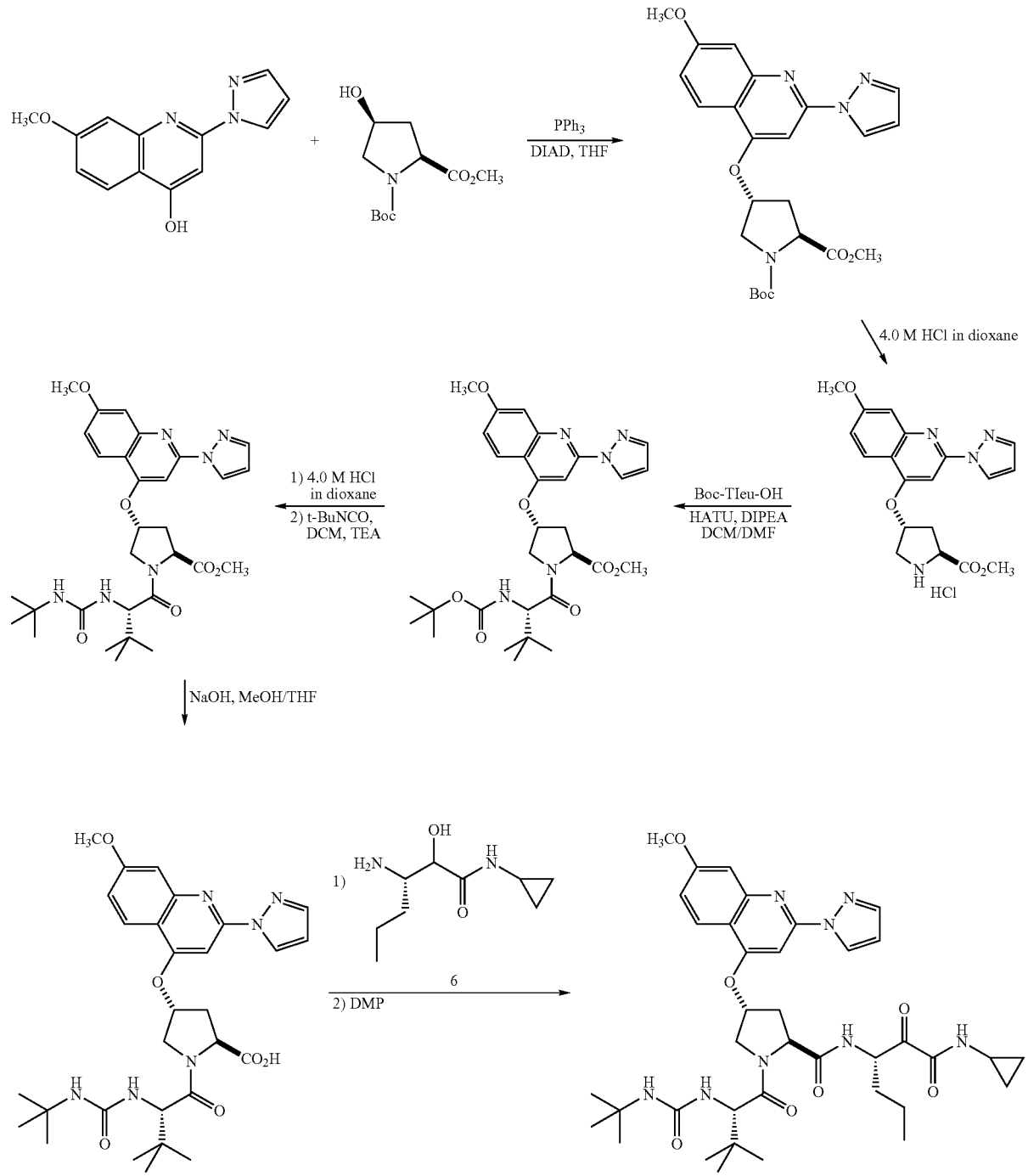

Step 1

To a solution of commercially available N-tert-Boc-cis-4S-hydroxy-L-proline methyl ester (370 mg, 1.51 mmol) and 7-methoxy-2-pyrazol-1-yl-quinolin-4-ol (PCT application publication No. WO 2000059929) (400 mg, 1.66 mmol) in dry tetrahydrofuran (15 mL) at 0° C. was added triphenylphosphine (594 mg, 2.27 mmol), followed by a slow addition of diisopropylazodicarboxylate (DIAD) (0.36 mL, 1.81 mmol) under $N_2$. The reaction mixture was slowly allowed to warm to room temperature and stirred for 18 hours. The crude reaction mixture was then concentrated and purified by flash chromatography to give (2S,4R)-1-tert-butyl-2-methyl-4-(7-methoxy-2-(1H-pyrazol-1-yl)quinolin-4-yloxy)-pyrrolidine-1,2-dicarboxylate in 69% yield.

Step 2

To a solution of (2S,4R)-1-tert-butyl-2-methyl-4-(7-methoxy-2-(1H-pyrazol-1-yl)quinolin-4-yloxy)-pyrrolidine-1,2-dicarboxylate (200 mg, 0.43 mmol) in dichloromethane (1 mL) was added 4.0 M HCl in dioxane (3.0 mL). After 1 hour, the reaction mixture was concentrated and dried to give (2S,4R)-methyl-4-(7-methoxy-2-(1H-pyrazol-1-yl)quinolin-4-yloxy)-pyrrolidine-2-carboxylate hydrochloride as a white solid.

Step 3

To a solution of (2S,4R)-methyl-4-(7-methoxy-2-(1H-pyrazol-1-yl)quinolin-4-yloxy)-pyrrolidine-2-carboxylate hydrochloride (67 mg, 0.165 mmol) in dichloromethane/N,N-dimethylformaide (2.0 mL, 1:1) was added Boc-L-tert-Leu-OH (38.1 mg, 0.165 mmol), O-(7-azabenzotriazol-1-yl)-1,1,3,3-tetramethyl-uronium hexafluorophosphate (HATU), (69 mg, 0.182 mmol) and diisopropylethylamine (0.1 mL, 0.5 mmol), and the mixture was stirred at room temperature. After 16 hours, the reaction mixture was diluted with ethyl acetate and washed with 1N HCl, saturated sodium bicarbonate, and brine. The ethyl acetate layer was dried over magnesium sulfate, filtered and evaporated to dryness under reduced pressure to give (2S,4R)-methyl-1-((S)-tert-butoxycarbonylamino)-3,3-dimethylbutanoyl)-4-(7-methoxy-2-(1H-pyrazol-1-yl)quinolin-4-yloxy)-pyrrolidine-2-carboxylate in quantitative yield.

Step 4

To a solution of crude (2S,4R)-methyl-1-((S)-tert-butoxycarbonylamino)-3,3-dimethylbutanoyl)-4-(7-methoxy-2-(1H-pyrazol-1-yl)quinolin-4-yloxy)-pyrrolidine-2-carboxylate in dichloromethane (1 mL) was added 4.0 M HCl in dioxane (3.0 mL). After 1 hour, the reaction mixture was concentrated and dried to give (S)-1-((2S,4R)-4-(7-methoxy-2-(1H-pyrazol-1-yl)quinolin-4-yloxy)-2-(methoxycarbonyl)pyrrolidin-1-yl)-3,3-dimethyl-1-oxobutan-2-ylcarbamic acid hydrochloride as a white solid which was used in the next step without further purification.

Step 5

To a solution of (S)-1-((2S,4R)-4-(7-methoxy-2-(1H-pyrazol-1-yl)quinolin-4-yloxy)-2-(methoxycarbonyl)pyrrolidin-1-yl)-3,3-dimethyl-1-oxobutan-2-ylcarbamic acid hydrochloride (0.165 mmol) in dichloromethane (3.0 mL) was added triethylamine (0.06 mL, 0.413 mmol) and tert-butyl-isocyanate (0.02 mL, 0.165 mmol) and the reaction mixture was stirred at room temperature. After 16 hours, the reaction mixture was diluted with dichloromethane and washed with 1N HCl, saturated sodium bicarbonate, and brine. The dichloromethane layer was then evaporated to dryness to give (2S,4R)-methyl-1-((S)-2-(3-tert-butylureido)-3,3-dimethylbutanoyl)-4-(7-methoxy-2-(1H-pyrazol-1-yl)quinolin-4-yloxy)-pyrrolidine-2-carboxylate.

Step 6

(2S,4R)-methyl-1-((S)-2-(3-tert-butylureido)-3,3-dimethylbutanoyl)-4-(7-methoxy-2-(1H-pyrazol-1-yl)quinolin-4-yloxy)-pyrrolidine-2-carboxylate was treated with methanol (6.0 mL), tetrahydrofuran (3.0 mL) and 1N sodium hydroxide (6. mL). After 1 hour at room temperature, the reaction mixture was concentrated, acidified with 1N HCl and extracted with ethyl acetate. The combined ethyl acetate layers were then washed with brine and dried ($MgSO_4$). The ethyl acetate layer was then filtered and evaporated to dryness to give (2S,4R)-methyl-1-((S)-2-(3-tert-butylureido)-3,3-dimethylbutanoyl)-4-(7-methoxy-2-(1H-pyrazol-1-yl)quinolin-4-yloxy)-pyrrolidine-2-carboxylic acid.

Step 7 tert-butyl-(3S)-1-(cyclopropylamino)-2-hydroxy-1-oxo-3-ylcarbamate (48 mg, 0.165 mmol) was dissolved in dichloromethane (3.0 mL) and trifluoroacetic acid (3.0 mL) was added. After stirring for 1 hour at room temperature, the reaction mixture was evaporated to dryness to give (3S)-3-amino-N-cyclopropyl-2-hydroxyhexanamide trifluoroacetic acid salt as a white solid. A solution of (2S,4R)-methyl-1-((S)-2-(3-tert-butylureido)-3,3-dimethylbutanoyl)-4-(7-methoxy-2-(1H-pyrazol-1-yl)quinolin-4-yloxy)-pyrrolidine-2-carboxylic acid in dichloromethane/N,N-dimethylformamide (1:1, 6.0 mL) was added to the (3S)-3-amino-N-cyclopropyl-2-hydroxyhexanamide trifluoroacetic acid salt, followed by O (7 azabenzotriazol 1 yl) 1,1,3,3 tetramethyl-uronium hexafluorophosphate (HATU) (75 mg, 0.198 mmol) and diisopropylethylamine (0.1 mL, 0.7 mmol). After 24 hours at room temperature, the reaction mixture was diluted with ethyl acetate and washed with 1N HCl, sodium bicarbonate, and brine. The ethyl acetate layer was dried over magnesium sulfate, filtered and evaporated to dryness under reduced pressure. The crude product was then dissolved in dry dichloromethane (10.0 mL) and Dess-Martin periodinane (112 mg, 0.264 mmol) was added. After stirring at room temperature for 2 hours, the reaction mixture was quenched with 0.26M sodium thiosulfate in saturated sodium bicarbonate and extracted with ethyl acetate. The combined ethyl acetate layers were then washed with saturated sodium bicarbonate and brine. Purification by preparative HPLC gave (2S,4R)-1-((S)-2-(3-tert-butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide in >99% purity by HPLC.

1H NMR: (DMSO-$d_6$) δ 8.76-8.70 (m, 2H); 8.22 (d, J=6.8 Hz, 1H); 8.11 (d, J=9.6 Hz, 1H); 7.87 (d, J=1.2 Hz, 1H); 7.45 (s, 1H); 7.27 (d, J=2.4 Hz, 1H); 7.00-6.97 (dd, J=2.8 and 9.6 Hz, 1H); 6.64-6.62 (m, 1H); 5.92 (brs, 1H); 5.49 (brs, 1H); 5.00-4.96 (m, 1H); 4.55-4.49 (m, 2H); 4.18 (d, J=5.6 Hz, 1H); 3.90 (s, 3H); 3.91-3.82 (m, 1H); 3.54 (brs, 1H); 2.75-2.72 (m, 1H); 2.54-2.51 (m, 1H); 2.17-2.14 (m, 1H); 1.69-1.66 (m, 1H); 1.40-1.34 (m, 3H); 1.13 (m, 9H); 0.93 (m, 9H); 0.90-0.82 (m, 3H); 0.65-0.53 (m, 4H). MS ($M^+$+1) 733.

Example 2

Synthesis of (2S,4R)-1-((S)-(3-tert-butylureido)-3,3-dimethylbutanoyl]-N-((S)-1-cyclobutyl-4-(cyclopropylamino)-3,4-dioxobutan-2-yl)-4-(7-methoxy-2-(1H-pyrazol-1-yl)-quinolin-4-yloxy)pyrrolidine-2-carboxamide

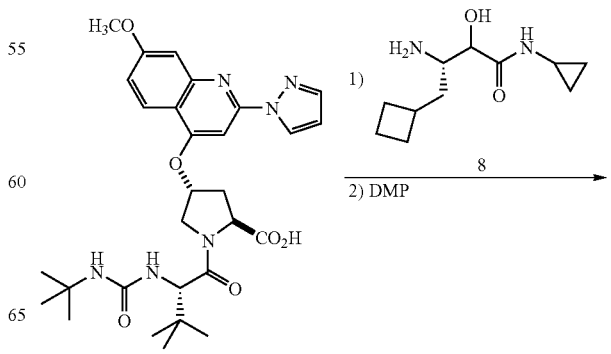

-continued

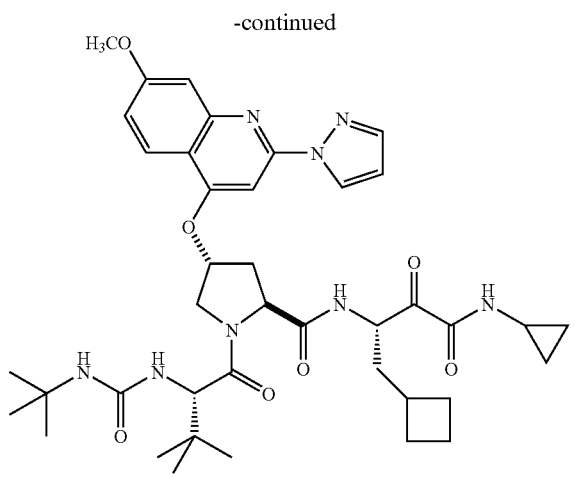

Step 1

Tert-butyl-(2S)-1-cyclobutyl-4-(cyclopropylamino)-3-hydroxy-4-oxobutan-2-ylcarbamate (51 mg, 0.165 mmol) was dissolved in dichloromethane (3.0 mL) and trifluoroacetic acid (3.0 mL) was added. After stirring for 1 hour at room temperature, the reaction mixture was evaporated to dryness to give (3S)-3-amino-4-cyclobutyl-N-cyclopropyl-2-hydroxy-butanamide trifluoroacetic acid salt as a white solid. A solution of (2S,4R)-1-((S)-2-(3-tert-butylureido)-3,3-dimethylbutanoyl)-4-(7-methoxy-2-(1H-pyrazol-1-yl)quinolin-4-yloxy)pyrrolidine-2-carboxylic acid in dichloromethane/N,N-dimethylformamide (1:1, 6.0 mL) was added to the (3S)-3-amino-4-cyclobutyl-N-cyclopropyl-2-hydroxy-butanamide trifluoroacetic acid salt followed by O (7 azabenzotriazol 1 yl) 1,1,3,3 tetramethyl-uronium hexafluorophosphate (HATU) (75 mg, 0.198 mmol) and diisopropylethylamine (0.1 mL, 0.7 mmol). After 24 hours at room temperature, the reaction mixture was diluted with ethyl acetate and washed with 1N HCl, saturated sodium bicarbonate, and brine. The ethyl acetate layer was dried (magnesium sulfate), filtered and evaporated to dryness under reduced pressure. The crude product was then dissolved in dry dichloromethane (10.0 mL) and 1,1,1-triacetoxy-1,1-dihydro-1,2-benziodoxol-3(1H)-one (Dess-Martin periodinane reagent, 112 mg, 0.264 mmol) added. After stirring at room temperature for 2 hours, the reaction mixture was quenched with 0.26M sodium thiosulfate in saturated sodium bicarbonate and extracted with ethyl acetate. The combined ethyl acetate layers were then washed with saturated sodium bicarbonate and brine. Purification by preparative HPLC gave (2S,4R)-1-((S)-(3-tert-butylureido)-3,3-dimethylbutanoyl]-N-((S)-1-cyclobutyl-4-(cyclopropylamino)-3,4-dioxobutan-2-yl)-4-(7-methoxy-2-(1H-pyrazol-1-yl)-quinolin-4-yloxy)pyrrolidine-2-carboxamide in >99% purity by HPLC.

$^1$H NMR: (DMSO-$d_6$) δ 8.76-8.69 (m, 2H); 8.19 (d, J=8.0 Hz, 1H); 8.10 (d, J=8.0 Hz, 1H); 7.87-7.86 (m, 1H); 7.45 (s, 1H); 7.27 (d, J=2.8 Hz, 1H); 7.00-6.97 (dd, J=2.8 and 9.6 Hz, 1H); 6.64-6.62 (m, 1H); 5.93 (brs, 1H); 5.48 (brs, 1H); 5.00-4.96 (m, 1H); 4.53-4.49 (m, 2H); 4.18 (d, J=9.2 Hz, 1H); 3.90 (s, 3H); 3.91-3.82 (m, 1H); 3.42 (brs, 2H); 2.75-2.72 (m, 1H); 2.54-2.51 (m, 1H); 2.17-2.14 (m, 1H); 1.96-1.89 (m, 2H); 1.78-1.50 (m, 6H); 1.13 (m, 9H); 0.94 (m, 9H); 0.65-0.53 (m, 4H). MS (M$^+$+1) 759.

Example 3

Synthesis of (2S,4R)-1-((S)-2-(3-tert-butylureido)-3,3-dimethylbutanoyl)-4-(5-chloro-pyridin-2-yloxy)-N-((S)-1-cyclobutyl-4-(cyclopropylamino)-3,4-dioxobutan-2-yl))pyrrolidine-2-carboxamide

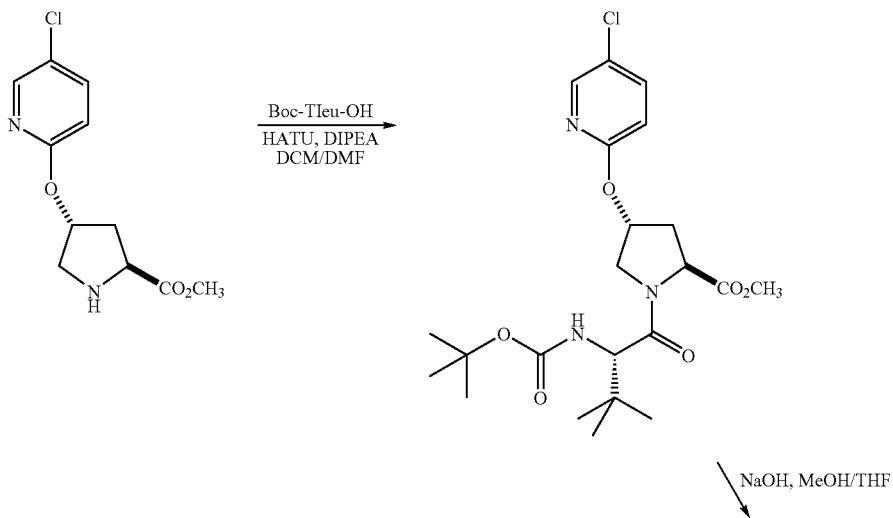

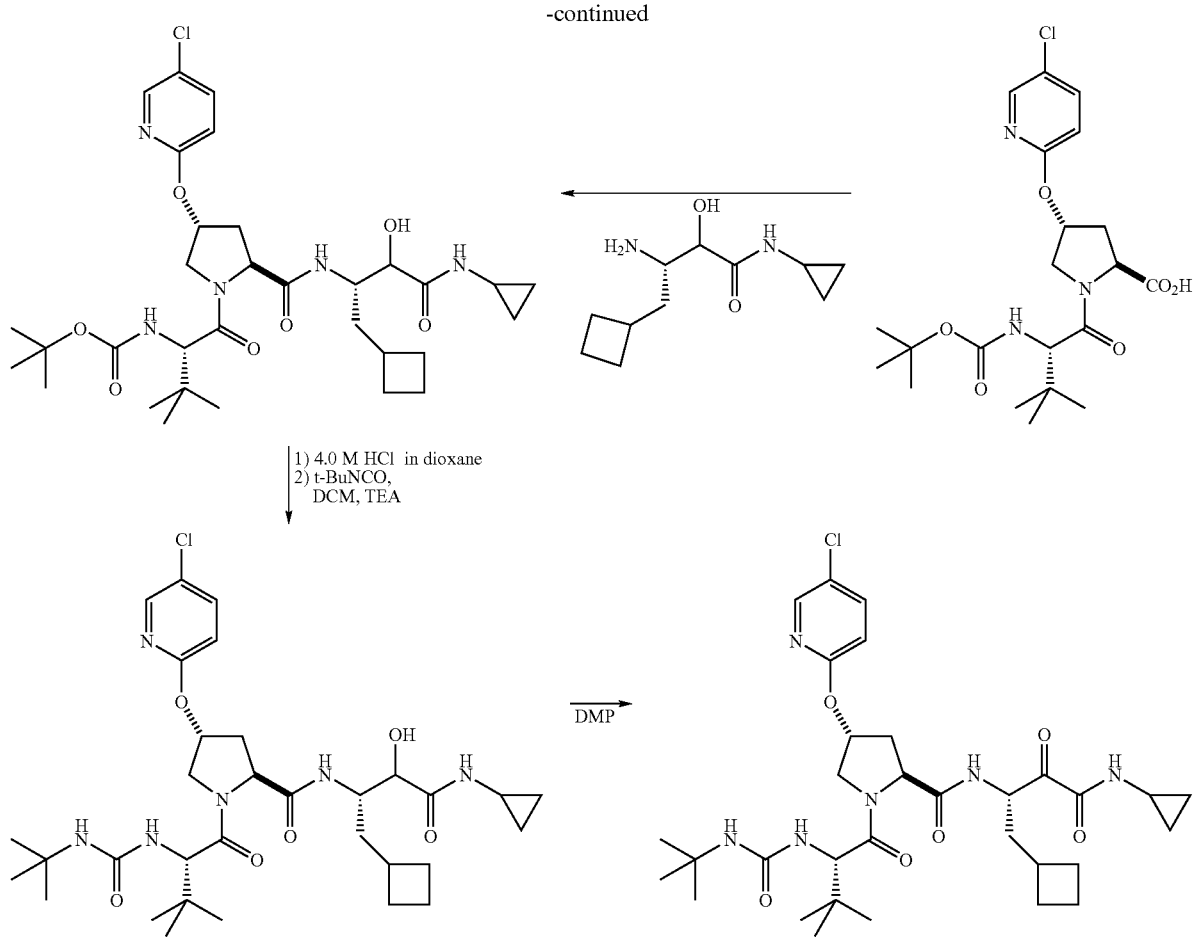

To commercially available t-Boc-(2S,4R)-hydroxyproline (1 mmol) in dimethylsulfoxide was added potassium tert-butoxide (3 mmol) in small portions over 15 minutes at 23° C. The mixture was stirred at 23° C. for 30 minutes, then cooled to 0° C. before adding 2,5-dichloropyridine (1.1 mmol) in small portions over 10 minutes. The reaction mixture was stirred at 23° C. for 16 hours. The resulting suspension was poured into 5% aqueous citric acid and extracted with ethyl acetate. The combined ethyl acetate layers were washed with brine and dried over magnesium sulfate. The organic portions were filtered and concentrated under reduced pressure to give a white solid. The solid material was dissolved in 4.0 M HCl in dioxane (10 mL). After 1 hour, the reaction mixture was concentrated under reduced pressure and dried to give (2S, 4R)-methyl-4-(5-chloropyridin-2-yloxy)pyrrolidine-2-carboxylate as the hydrochloride salt.

Step 1

To (2S,4R)-methyl-4-(5-chloropyridin-2-yloxy)pyrrolidine-2-carboxylate hydrochloride (242 mg, 0.829 mmol) in dichloromethane/N,N-dimethylformamide (10 mL, 1:1) was added Boc-L-tert-Leu-OH (192 mg, 0.829 mmol), O (7 azabenzotriazol 1 yl) 1,1,3,3 tetramethyl-uronium hexafluorophosphate (HATU) (347 mg, 0.912 mmol) and diisopropylethylamine (0.37 mL, 2.07 mmol), and the reaction mixture was stirred at room temperature. After 16 hours, the reaction mixture was diluted with ethyl acetate and washed with saturated sodium bicarbonate, and brine. The ethyl acetate layer was dried over magnesium sulfate, filtered and evaporated to dryness under reduced pressure to give (2S,4R)-methyl-1-((S)-2-(3-tert-butoxycarbonylamino)-3,3-dimethylbutanoyl)-4-(5-chloro-pyridin-2-yloxy)-pyrrolidine-2-carboxylate in quantitative yield.

Step 2

(2S,4R)-methyl-1-((S)-2-(3-tert-butoxycarbonylamino)-3,3-dimethylbutanoyl)-4-(5-chloro-pyridin-2-yloxy)-pyrrolidine-2-carboxylate was treated with methanol (5.0 mL), tetrahydrofuran (3.0 mL) and 1N sodium hydroxide (5.0 mL). After 2 hours at room temperature, the reaction mixture was concentrated, acidified with 1N HCl and extracted with ethyl acetate. The combined ethyl acetate layers were then washed with brine and dried over magnesium sulfate. The ethyl acetate layer was then filtered and evaporated to dryness under reduced pressure to give (2S,4R)-1-((S)-2-(3-tert-butoxycarbonylamino)-3,3-dimethylbutanoyl)-4-(5-chloro-pyridin-2-yloxy)-pyrrolidine-2-carboxylic acid.

Step 3

To (3S)-3-amino-4-cyclobutyl-N-cyclopropyl-2-hydroxybutanamide (214 mg, 0.83 mmol) was added 4.0 M HCl in dioxane (11.0 mL). After 1 hour, the reaction mixture was concentrated and dried to give (3S)-3-amino-4-cyclobutyl-N-cyclopropyl-2-hydroxy-butanamide HCl salt as a white solid. To this salt was added (2S,4R)-1-((S)-2-(3-tert-butoxycarbonylamino)-3,3-dimethylbutanoyl)-4-(5-chloro-pyridin-2-yloxy)-pyrrolidine-2-carboxylic acid in dichloromethane/N, N-dimethylformamide (1:1, 10.0 mL), 1 (3 dimethylaminopropyl)-3 ethylcarbodiimide hydrochloride (EDCI) (238 mg, 1.24 mmol), 1-hydroxybenzotriazole (HOBT) (190 mg, 1.24 mmol) and N-methylmorpholine (0.6 mL, 3.32 mmol). After 16 hours at room temperature, the reaction mixture was diluted with ethyl acetate and washed with saturated sodium bicarbonate, brine, and dried over magnesium sulfate. The ethyl acetate layer was then filtered, concentrated under reduced pressure, and the residue purified by flash chromatography to give tert-butyl (2S)-1-((2S,4R)-4-(5-chloro-pyridin-2-yloxy)-2-((2S)-1-cyclobutyl-4-(cyclopropylamino)-3-hydroxy-4-oxobutan-2-ylcarbamoyl)pyrrolidin-1-yl)-3,3-dimethyl-1-oxobutan-2-ylcarbamate in 58% yield.

Step 4

To tert-butyl (2S)-1-((2S,4R)-4-(5-chloro-pyridin-2-yloxy)-2-((2S)-1-cyclobutyl-4-(cyclopropylamino)-3-hydroxy-4-oxobutan-2-ylcarbamoyl)pyrrolidin-1-yl)-3,3-dimethyl-1-oxobutan-2-ylcarbamate (313 mg, 0.482 mmol) in dichloromethane (2 mL) was added 4.0 M HCl in dioxane (3.0 mL). After 1 hour, the reaction mixture was concentrated under reduced pressure and dried to give (2S,4R)-1-((S)-2-amino-3,3-dimethylbutanoyl)-4-(5-chloro-pyridin-2-yloxy)-N-((2S)-1-cyclobutyl-4-(cyclopropylamino)-3-hydroxy-4-oxobutan-2-yl)pyrrolidine-2-carboxamide HCl salt as a white solid.

Step 5

To a solution of (2S,4R)-1-((S)-2-amino-3,3-dimethylbutanoyl)-4-(5-chloro-pyridin-2-yloxy)-N-((2S)-1-cyclobutyl-4-(cyclopropylamino)-3-hydroxy-4-oxobutan-2-yl)pyrrolidine-2-carboxamide HCl salt (45 mg, 0.077 mmol) in dichloromethane (3.0 mL) was added triethylamine (0.02 mL, 0.154 mmol). After 5 minutes at room temperature, tert-butylisocyanate (0.01 mL, 0.077 mmol) was added and the reaction mixture was stirred at room temperature. After 16 hours, the reaction mixture was diluted with dichloromethane and washed with 1N HCl, saturated sodium bicarbonate, and brine. The dichloromethane layer was then evaporated to dryness under reduced pressure to give (2S,4R)-1-((S)-2-(3-tert-butylureido)-3,3-dimethylbutanoyl)-4-(5-chloropyridin-2-yloxy)-N-((2S)-1-cyclobutyl-4-(cyclopropylamino)-3-hydroxy-4-oxobutan-2-yl)pyrrolidine-2-carboxamide.

Step 6

(2S,4R)-1-((S)-2-(3-tert-butylureido)-3,3-dimethylbutanoyl)-4-(5-chloropyridin-2-yloxy)-N-((2S)-1-cyclobutyl-4-(cyclopropylamino)-3-hydroxy-4-oxobutan-2-yl)pyrrolidine-2-carboxamide was dissolved in dry dichloromethane (4.0 mL) and Dess-Martin periodinane (44 mg, 0.103 mmol) was added. After stirring at room temperature for 2 hours the reaction mixture was quenched with 0.26M sodium thiosulfate in saturated sodium bicarbonate and extracted with ethyl acetate. The combined ethyl acetate layers were then washed with saturated sodium bicarbonate and brine, the organic layer dried over magnesium sulfate, and the solvent removed under reduced pressure. Purification of the residue by preparative HPLC gave (2S,4R)-1-((S)-2-(3-tert-butylureido)-3,3-dimethylbutanoyl)-4-(5-chloro-pyridin-2-yloxy)-N-((S)-1-cyclobutyl-4-(cyclopropylamino)-3,4-dioxobutan-2-yl))pyrrolidine-2-carboxamide in >90% purity by HPLC.

$^1$H NMR: (DMSO) 8.91-8.73 (m, 1H); 8.30-8.24 (m, 2H); 7.92-7.7.80 (m, 1H); 6.94-6.84 (m, 1H); 5.97 (brs, 1H); 5.50 (s, 1H); 5.00-4.95 (m, 1H); 4.54-4.52 (m, 1H); 4.17-3.88 (m, 3H); 2.75-2.72 (m, 1H); 2.54-2.51 (m, 1H); 2.40-2.32 (m, 1H); 2.17-1.60 (m, 10H); 1.13 (m, 9H); 0.91 (m, 9H); 0.67-0.58 (m, 4H). MS (M$^+$+1) 648.

Example 4

Synthesis of tert-butyl (S)-1-((2S,4R)-2-((S)-1-(cyclopropylamino)-1,2-dioxohexan-3-ylcarbamoyl)-4-(7-methoxy-2-(1H-pyrazol-1-yl)quinolin-4-yloxy)pyrrolidin-1-yl)-3,3-dimethyl-1-oxobutan-2-ylcarbamate

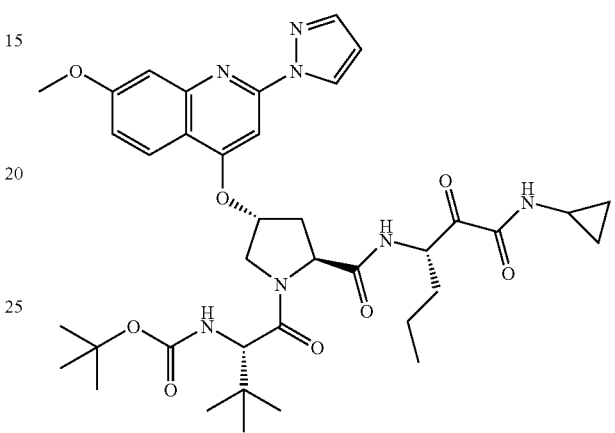

Similarly, following the procedure of Example 1 above, but eliminating steps 4 and 5, tert-butyl (S)-1-(2S,4R)-2-(cyclopropylamino)-1,2-dioxohexan-3-ylcarbamoyl)-4-(7-methoxy-2-(1H-pyrazol-1-yl)quinolin-4-yloxy)pyrrolidin-1-yl)-3,3-dimethyl-1-oxobutan-2-ylcarbamate was obtained. MS: 734 (M+1).

Example 5

Synthesis of tert-butyl (S)-1-((2S,4R)-2-(cyclopropylamino)-1,2-dioxohexan-3-ylcarbamoyl)-4-(7-methoxy-2-phenylquinolin-4-yloxy)pyrrolidin-1-yl)-3,3-dimethyl-1-oxobutan-2-ylcarbamate

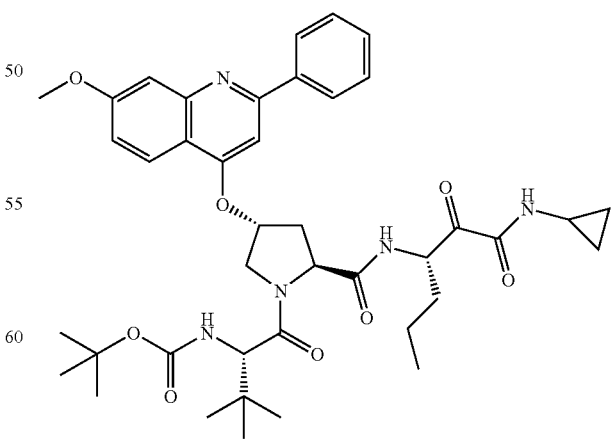

Similarly, following the procedure of Example 4 above, but substituting 7-methoxy-2-pyrazol-1-yl-quinolin-4-ol with 7-methoxy-2-phenyl-quinolin-4-ol, tert-butyl (S)-1-(2S,4R)-2-(cyclopropylamino)-1,2-dioxohexan-3-ylcarbamoyl)-4-(7-methoxy-2-phenylquinolin-4-yloxy)pyrrolidin-1-yl)-3,3-dimethyl-1-oxobutan-2-ylcarbamate was obtained MS: 744 (M+1)

Example 6

Synthesis of tert-butyl (S)-1-((2S,4R)-4-(5-chloropyridin-2-yloxy)-2-((S)-1-(cyclopropylamino)-1,2-dioxohexan-3-ylcarbamoyl)pyrrolidin-1-yl)-3,3-dimethyl-1-oxobutan-2-ylcarbamate

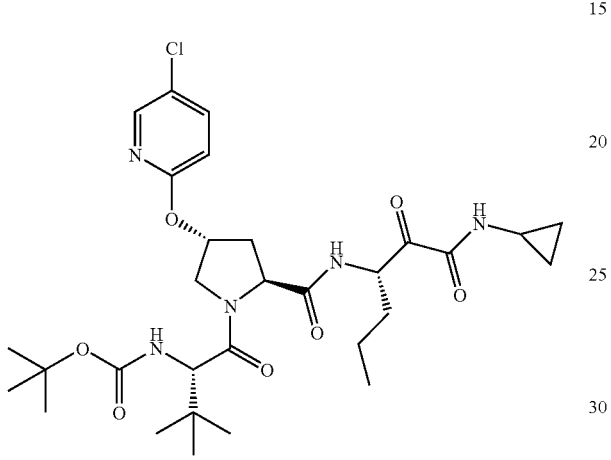

Similarly, following the procedure of Example 4 above, but substituting 4R-(7-methoxy-2-pyrazol-1-yl-quinolin-4-yloxy)-pyrrolidine-2S-carboxylic acid methyl ester hydrochloride with 4R-(5-chloropyridin-2-yloxy)pyrrolidine-2-carboxylic acid methyl ester hydrochloride the title compound was obtained MS: 622 (M+1).

Example 7

Synthesis of tert-butyl-1-((2S,4R)-4-(5-chloropyridin-2-yloxy)-2-((S)-1-cyclobutyl-4-(cyclopropylamino)-3,4-dioxobutan-2-ylcarbamoyl)pyrrolidin-1-yl)-3,3-dimethyl-1-oxobutan-2-ylcarbamate

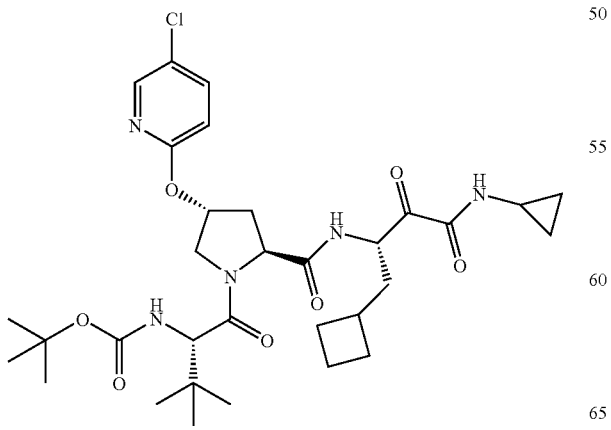

Similarly, following the procedure of Example 4 above, but substituting 4R-(7-methoxy-2-pyrazol-1-yl-quinolin-4-yloxy)-pyrrolidine-2S-carboxylic acid methyl ester hydrochloride with 4R-(5-chloro-pyridin-2-yloxy)pyrrolidine-2-carboxylic acid methyl ester hydrochloride and (1S-cyclobutylmethyl-2-cyclopropylcarbamoyl-2-hydroxyethyl)-carbamic acid tert-butyl ester in place of [1S-(cyclopropylcarbamoylhydroxymethyl)butyl]carbamic acid tert-butyl ester, the title compound was obtained. MS: 648 (M+1)

Example 8

Synthesis of (2S,4R)-1-((S)-2-(3-tert-butylureido)-3,3-dimethylbutanoyl]-4-(5-chloro-pyridin-2-yloxy)-N-((S)-1-(cyclopropylamino)-1,2-dioxohexan-3-yl0pyrrolidine-2-carboxamide

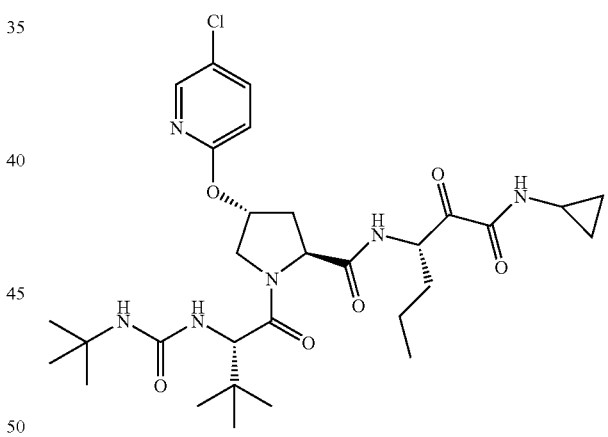

Similarly, following the procedure of Example 3 above, but substituting (1S-cyclobutylmethyl-2-cyclopropylcarbamoyl-2-hydroxyethyl)-carbamic acid tert-butyl ester with [1S-(cyclopropyl-carbamoylhydroxymethyl)butyl]carbamic acid tert-butyl ester, the title compound was obtained. MS: 621 (M+1).

Example 9

Synthesis of (2S,4R)-1-((S)-2-(3-tert-Butylureido)-3,3-dimethylbutanoyl)-N-((S)-1-cyclopropylamino)-1,2-dioxohexan-3-yl)-4-(6-methoxyisoquinolin-1-yloxy)-pyrrolidine-2-carboxamide

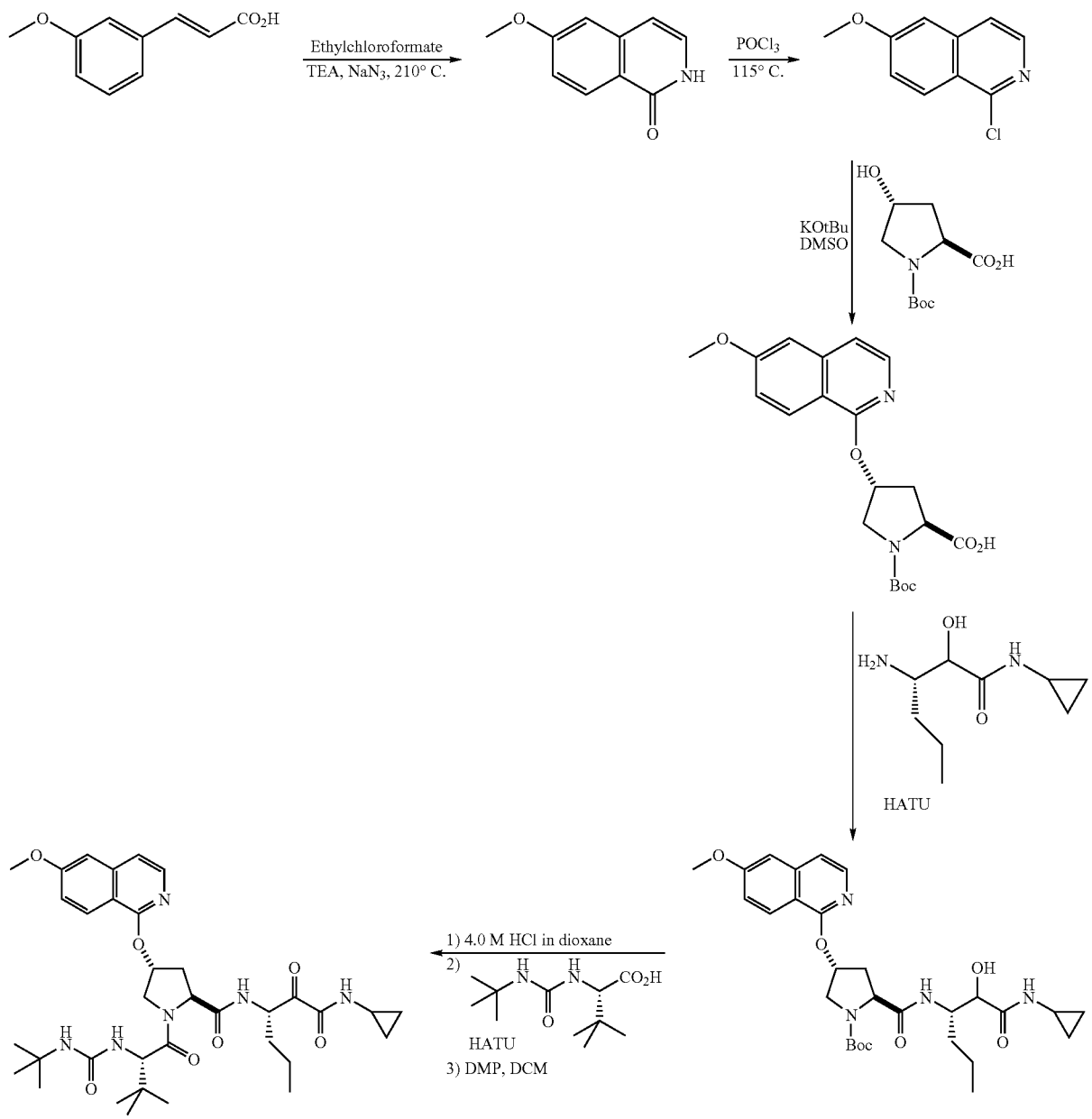

Step 1

Ethyl chloroformate (4.3 mL, 44.5 mmol) was added drop wise at 0° C. to a solution of 3-methoxycinnamic acid (5.3 g, 29.7 mmol) and triethylamine (8.3 mL, 59.4 mmol) in acetone (35 mL). After 1 hour at 0° C., aqueous sodium azide (3.1 g, 47.5 mmol, 16 mL water) was added drop wise, and the reaction mixture was stirred at 23° C. for 16 hours. Water (50 mL) was added to the mixture and the volatile removed under reduced pressure. The resulting slurry was extracted with toluene (3×25 mL) and the combined organic layers were dried over magnesium sulfate. The dried solution was filtered and added dropwise to a solution of diphenylmethane (25 mL) and tributylamine (14.2 mL, 59.4 mmol) at 190° C. The toluene was distilled off as added. After complete addition, the reaction temperature was raised to 210° C. for 2 hours. After cooling, the precipitated product was collected by filtration, washed with hexanes, and dried under vacuum to yield 6-methoxyisoquinolin-1(2H)-one (1.7 g, 9.7 mmol, 33% yield). MS m/z 176 (M$^+$+H).

Step 2

A suspension of 6-methoxyisoquinolin-1(2H)-one (900 mgs, 5.1 mmol) in phosphorus oxychloride (POCl$_3$, 4 mL) was heated at 110° C. for 3 hours (clear solution obtained upon heating). After 3 hours, the reaction mixture was concentrated under reduced pressure. The residue was poured into iced water (10 mL), the pH was then adjusted to 10 with 3N sodium hydroxide, and the mixture extracted with chloroform (3×25 mL). The combined chloroform layers were washed with brine and dried over magnesium sulfate. The organic layer was then filtered, concentrated under reduced pressure, and purified by flash chromatography (50% ethyl acetate/hexane) to give 1-chloro-6-methoxyisoquinoline (720 mgs, 3.7 mmol, 73% yield) as white solid. $^1$H NMR (CD$_3$OD): 8.23 (d, 1H, J=8.8 Hz); 8.11 (d, 1H, J=6.0 Hz); 7.69 (d, 1H, J=6.0 Hz); 7.37-7.33 (m, 2H); 3.97 (s, 3H). MS m/z 194 (M$^+$+H).

Step 3

To commercially available N-t-Boc-(2S,4R)-hydroxyproline (684 mg, 2.96 mmol) in dimethylsulfoxide (20 mL), potassium tert-butoxide (997 mgs, 8.88 mmol) was added in small portions, over 15 minutes at 23° C. The mixture was stirred at 23° C. for 30 minutes, and then cooled to 0° C. 1-Chloro-6-methoxy-isoquinoline (600 mgs, 3.11 mmol) was then added in small portions over 10 minutes. The reaction mixture was stirred at 23° C. for 16 hours. The resulting suspension was poured into 5% aqueous citric acid (100 mL) and extracted with ethyl acetate (3×50 mL). The combined ethyl acetate layers were washed with brine and dried over magnesium sulfate. The organic layer was then filtered and concentrated under reduced pressure to give (2S,4R)-1-(tert-butoxycarbonyl)-4-(6-methoxy-isoquinolin-1-yloxy)pyrrolidine-2-carboxylic acid (1.04 g, 2.68 mmol, 91% yield) as a white solid. MS m/z 389 (M$^+$+H). This material was used in the next step as crude without further purification.

Step 4

To tert-butyl-(3S)-1-(cyclopropylamino)-2-hydroxy-1-oxo-hexan-3-ylcarbamate (100 mg, 0.35 mmol) was added 4.0 M HCl in dioxane (10 mL). After 1 hour, the reaction mixture was concentrated and dried to give the corresponding HCl salt as a white solid. To the above amine HCl salt in dichloromethane/N,N-dimethylformamide (8:3, 11.0 mL) was added (2S,4R)-1-(tert-butoxycarbonyl)-4-(6-methoxy-isoquinolin-1-yloxy)pyrrolidine-2-carboxylic acid (136 mg, 0.35 mmol), O (7 azabenzotriazol 1 yl) 1,1,3,3 tetramethyl-uronium hexafluorophosphate (HATU) (160 mg, 0.42 mmol) and diisopropylethylamine (0.2 mL, 1.05 mmol). After 2 hours at room temperature reaction the mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure to give (2S,4R)-tert-butyl-2-((3S)-1-(cyclopropylamino)-2-hydroxy-1-oxohexan-3-ylcarbamoyl)-4-(6-methoxy-isoquinolin-1-yloxy)-pyrrolidine-1-carboxylate.

Step 5

To the above crude compound was added 4.0 M HCl in dioxane (10 mL). After 1 hour, the reaction mixture was concentrated and dried to give the corresponding HCl salt as a white solid. To the amine HCl salt in dichloromethane/N,N-dimethylformamide (8:3, 11.0 mL) was added 2S-(3-tert-butyl-ureido)-3,3-dimethyl-butyric acid (81.0 mg, 0.35 mmol), O (7 azabenzotriazol 1 yl) 1,1,3,3 tetramethyl-uronium hexafluorophosphate (HATU) (160 mg, 0.42 mmol) and diisopropylethylamine (0.2 mL, 1.05 mmol). After 16 hours at room temperature, the reaction mixture was diluted with ethyl acetate and washed with 1N HCl (2×), sodium bicarbonate (1×), and brine (1×). The ethyl acetate layer was dried over magnesium sulfate, filtered, and evaporated to dryness under reduced pressure.

Step 6

The crude product was then dissolved in dry dichloromethane (10.0 mL) and Dess-Martin periodinane (223 mg, 0.525 mmol) was added. After stirring at room temperature for 2 h, the reaction mixture was quenched with 0.26M sodium thiosulfate in saturated sodium bicarbonate and extracted with ethyl acetate (3×). The combined ethyl acetate layers were then washed with saturated sodium bicarbonate (2×) and brine (1×). Purification by preparative HPLC gave (2S,4R)-1-((S)-2-(3-tert-butylureido)-3,3-dimethylbutanoyl)-N-((S)-1-(cyclopropylamino)-1,2-dioxohexan-3-yl)-4-(6-methoxyisoquinolin-1-yloxy)-pyrrolidine-2-carboxamide in >95% purity by HPLC. $^1$H NMR: (DMSO-d$_6$) 8.74 (d, 1H, J=4.8 Hz); 8.28 (d, 1H, J=7.2 Hz); 8.15 (d, 1H, J=9.2 Hz); 7.97 (d, 1H, J=6.0 Hz); 7.34-7.32 (m, 2H); 7.11-7.08 (m, 1H); 5.94 (brs, 1H); 5.72-5.70 (m, 1H); 5.04-5.00 (m, 1H); 4.58 (t, 1H, J=8.4 Hz); 4.34-4.22 (m, 2H); 3.91 (s, 3H); 3.90-3.86 (m, 1H); 2.79-2.74 (m, 1H); 2.54-2.51 (m, 1H); 2.18-2.11 (m, 1H); 1.77-1.70 (m, 1H); 1.48-1.38 (m, 3H); 1.15 (m, 9H); 0.91 (m, 9H); 0.90-0.86 (m, 3H); 0.69-0.56 (m, 4H). MS m/z 667 (M$^+$+H), 689 (M$^+$+Na), 665 (M$^+$−H).

Example 10

Synthesis of (2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-methoxyisoquinolin-1-yloxy)-pyrrolidine-2-carboxamide

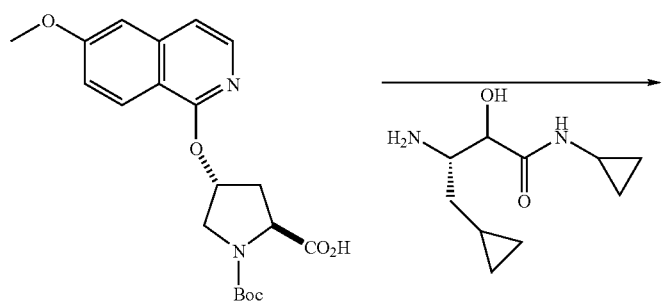

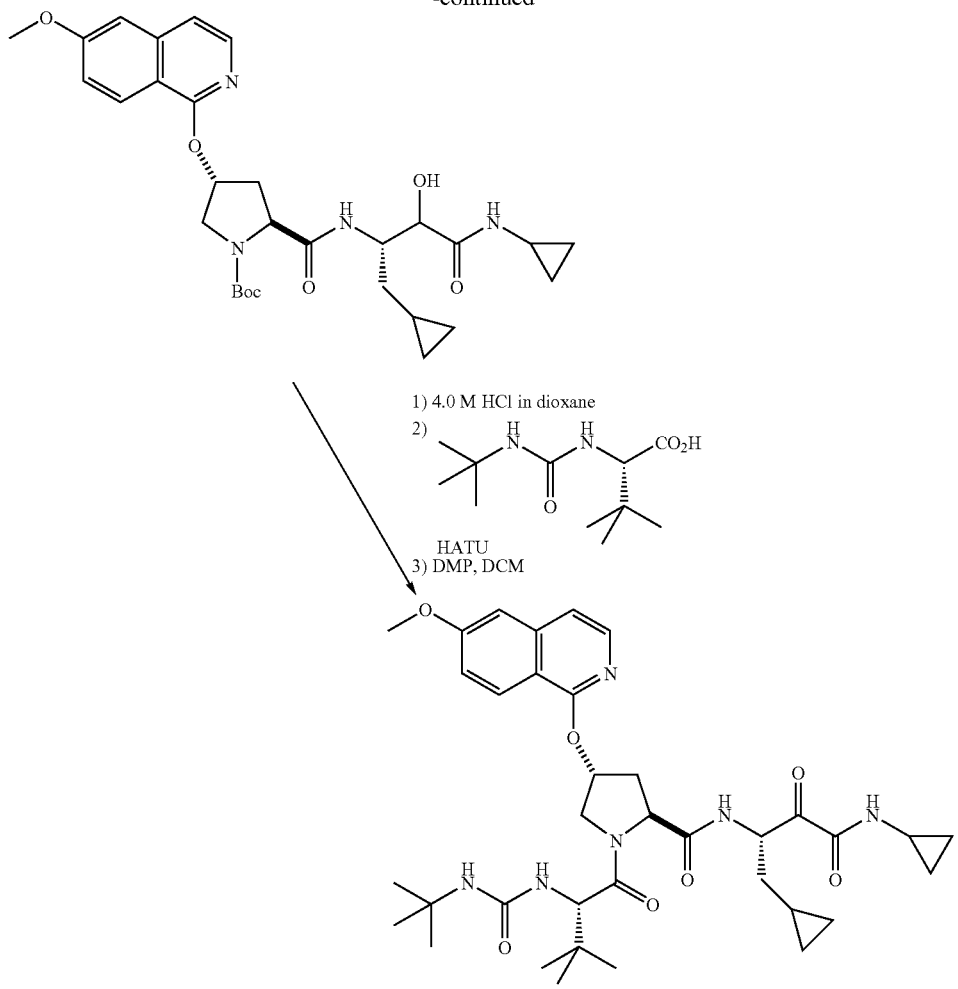

Step 1

To (3S)-3-amino-N-dicyclopropyl-2-hydroxy-butanamide HCl salt (47 mg, 0.2 mmol) in dichloromethane/N,N-dimethylformamide (5:1.5, 6.5 mL) was added (2S,4R)-1-(tert-butoxycarbonyl)-4-(6-methoxyisoquinolin-1-yloxy)-pyrrolidine-2-carboxylic acid (78 mg, 0.2 mmol), O (7 azabenzotriazol 1 yl) 1,1,3,3 tetramethyl-uronium hexafluorophosphate (HATU) (91 mg, 0.4 mmol) and diisopropylethylamine (0.1 mL, 0.6 mmol). After 16 hours at room temperature, the reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure to give (2S,4R)-tertbutyl-2-((2S)-1-cyclopropyl-4-(cyclopropylamino)-3-hydroxy-4-oxobutan-2-y; carbamoyl)-4-(6-methoxyisoquinolin-1-yloxy)-pyrrolidine-1-carboxylate.

Step 2

To the above crude compound was added 4.0 M HCl in dioxane (5.0 mL). After 1 hour, the reaction mixture was concentrated and dried to give the corresponding HCl salt as a white solid. To the above amine HCl salt in dichloromethane/N,N-dimethylformamide (7:3. 10.0 mL) was added S-2-(3-tert-butylureido)-3,3-dimethylbutanoic acid (46 mg, 0.2 mmol), O (7 azabenzotriazol 1 yl) 1,1,3,3 tetramethyl-uronium hexafluorophosphate (HATU) (91 mg, 0.24 mmol) and diisopropylethylamine (0.1 mL, 0.6 mmol). After 3 hours at room temperature, the reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure.

Step 3

The crude product was then dissolved in dry dichloromethane (8.0 mL) and Dess-Martin periodinane (127 mg, 0.3 mmol) was added. After stirring at room temperature for 2 hours, the reaction mixture was quenched with 0.26M sodium thiosulfate in saturated sodium bicarbonate and extracted with ethyl acetate (3×). The combined ethyl acetate layers were then washed with saturated sodium bicarbonate (2×) and brine (1×). Purification by preparative HPLC gave (2S,4R)-1-((S)-2-(3-tert-butylureido)-3,3-dimethylbutanoyl)-N-((S)-1-cyclopropyl-4-(cyclopropylamino)-3,4-dioxobutan-2-yl)-4-(6-methoxyisoquinolin-1-yloxy)-pyrrolidine-2-carboxamide in >95% purity by HPLC. MS m/z 679 (M$^+$+H), 701 (M$^+$+Na), 677 (M$^+$−H).

Example 11

Synthesis of (2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-ethoxyisoquinolin-1-yloxy)-pyrrolidine-2-carboxamide

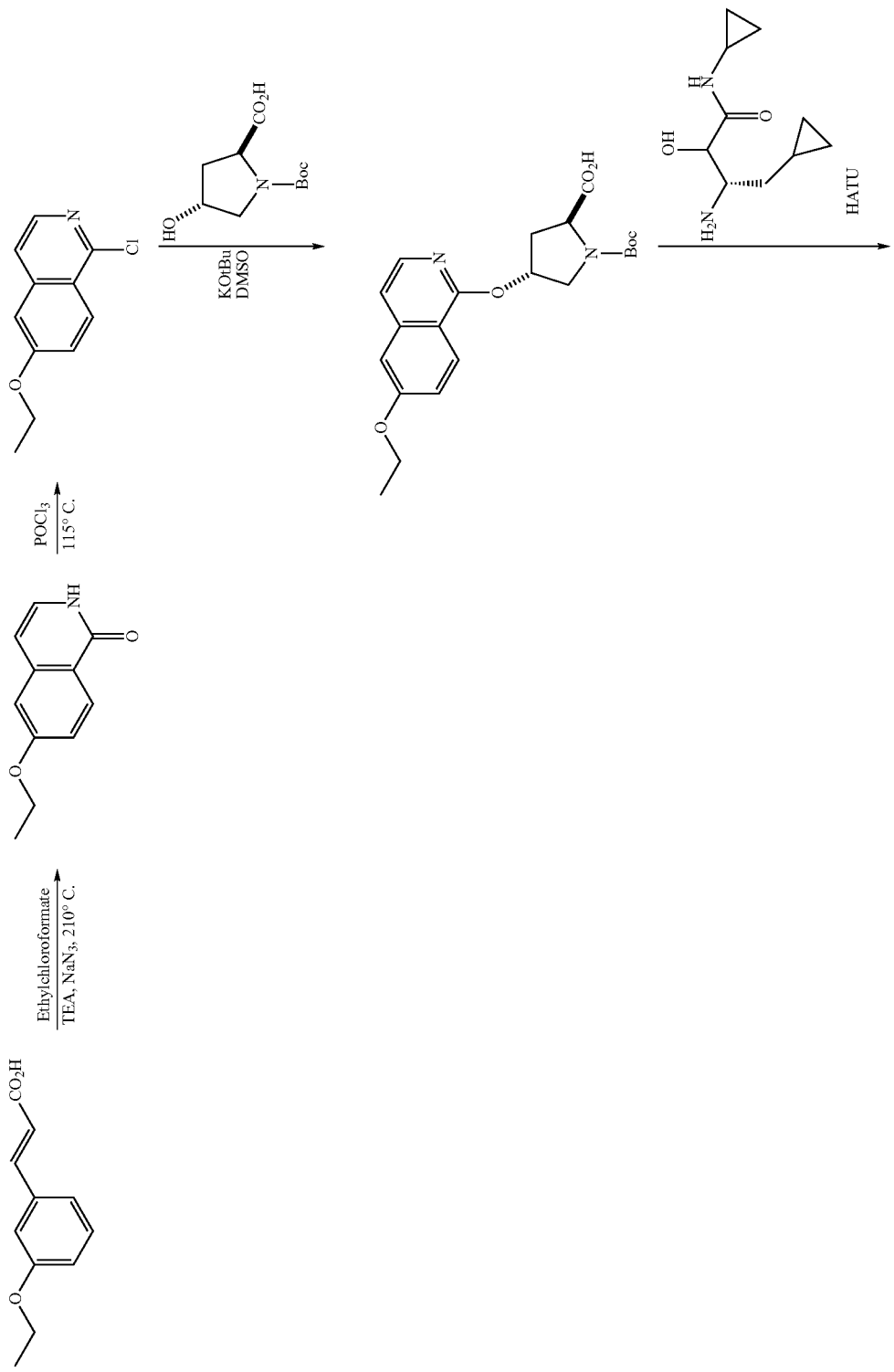

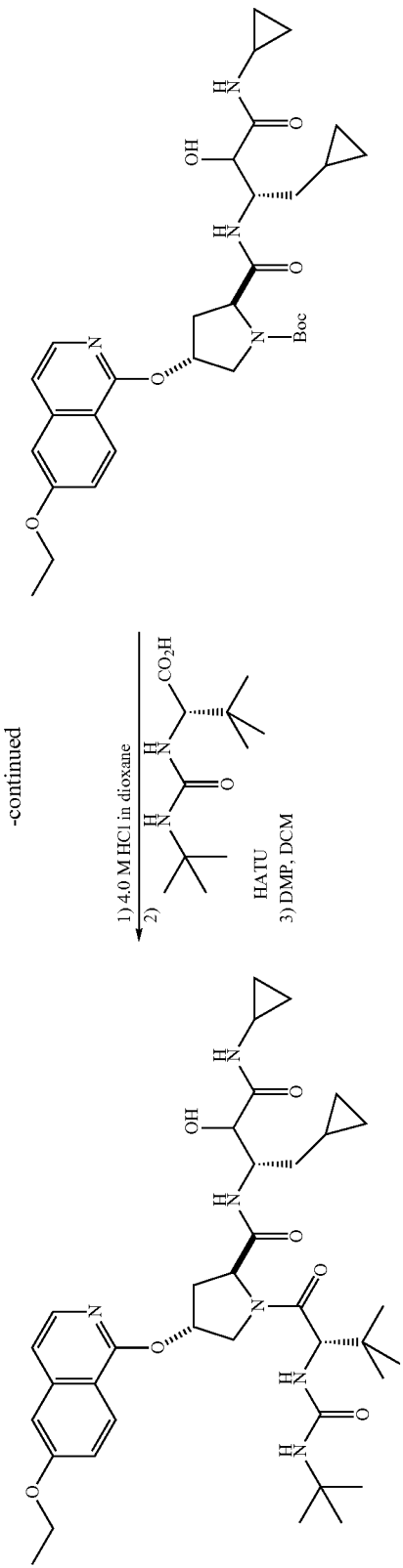

Step 1

Ethyl chloroformate (4.3 mL, 44.5 mmol) was added drop wise at 0° C. to a solution of 3-ethoxycinnamic acid (5.71 g, 29.7 mmol) and triethylamine (8.3 mL, 59.4 mmol) in acetone (35 mL). After 1 hour at 0° C., aqueous sodium azide (3.1 g, 47.5 mmol, 16 mL water) was added dropwise and the reaction mixture was stirred at 23° C. for 16 hours. Water (50 mL) was added to the mixture and the volatile was removed under vacuo. The resulting slurry was extracted with toluene (3×25 mL) and the combined organic layers were dried ($MgSO_4$). The dried solution was filtered and added dropwise at 190° C. to a solution of diphenylmethane (25 mL) and tributylamine (14.2 mL, 59.4 mmol). The toluene was distilled off as added. After complete addition, the reaction temperature was raised to 210° C. for 2 h. After cooling, the precipitated product was collected by filtration and washed with hexanes and dried under vacuum to yield 6-ethoxy-2H-isoquinolin-1-one (1.92 g, 10.2 mmol, 34% yield). MS m/z 190 ($M^+$+H).

Step 2

A suspension of 6-ethoxy-2H-isoquinolin-1-one (896 mg, 4.74 mmol) in phosphorus oxychloride ($POCl_3$, 4 mL) was heated at 110° C. for 3 hours (clear solution obtained upon heating). After 3 hours, the reaction mixture was concentrated under reduced pressure. The residue was poured into iced water (10 mL), the pH adjusted to 10 with 3N sodium hydroxide, and the mixture extracted with chloroform (3×25 mL). The combined chloroform layers were washed with brine and dried over magnesium sulfate. The organic layer was then filtered and concentrated under reduced pressure to give 1-chloro-6-ethoxy-isoquinoline (866 mg, 4.18 mmol, 88% yield, >90% pure) as tan solid. MS m/z 208 ($M^+$+H).

Step 3

To commercially available N-t-Boc-(2S,4R)-hydroxyproline (531 mg, 2.30 mmol) in dimethylsulfoxide (20 mL), potassium tert-butoxide (774 mg, 6.9 mmol) was added in small portions, over 15 minutes at 23° C. The mixture was stirred at 23° C. for 30 minutes and then cooled to 0° C. To this mixture was added at 0° C. 1-chloro-6-ethoxy-isoquinoline (500 mgs, 2.41 mmol) in small portions over 10 minutes. The reaction mixture was stirred at 23° C. for 16 hours. The resulting suspension was poured into water, and the mixture was washed with ether (2×) and ethyl acetate (2×). The aqueous layer was acidified with aqueous 1N HCl to about pH 4, and extracted with dichloromethane (3×). The combined dichloromethane layers were washed with brine and dried over magnesium sulfate. The organic layer was then filtered, and concentrated under reduced pressure to give (2S,4R)-1-(tert-butoxycarbonyl)-4-(6-ethoxyisoquinolin-1-yloxy)pyrrolidine-2-carboxylic acid (crude wt=1.18 g, >90% pure). MS m/z 403 ($M^+$+H), 401 ($M^+$−H), 303 ($M^+$−Boc). This material was used in the next step as crude without further purification.

Step 4

To (3S)-3-amino-N,4-dicyclopropyl-2-hydroxybutanamide HCl salt (66 mgs, 0.28 mmol) in dichloromethane/N,N-dimethylformamide (10:3, 13 mL) was added (2S,4R)-1-(tert-butoxycarbonyl)-4-(6-ethoxyisoquinolin-1-yloxy)pyrrolidine-2-carboxylic acid (114 mgs, 0.28 mmol), O (7 azabenzotriazol 1 yl) 1,1,3,3 tetramethyl-uronium hexafluorophosphate (HATU) (128 mg, 0.34 mmol) and diisopropylethylamine (0.15 mL, 0.84 mmol). After 1 hour at room temperature, the reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure to give (2S,4R)-tert-butyl-2-((2S)-1-cyclopropyl-4-(cyclopropylamino)-3-hydroxy-4-oxobutan-2-yl-carbamoyl)-4-(6-ethoxy-isoquinolin-1-yloxy)pyrrolidine-1-carboxylate.

Step 5

To the above crude compound was added 4.0 M HCl in dioxane (10 mL). After 1 hour, the reaction mixture was concentrated and dried to give the corresponding HCl salt as a white solid. To the above amine HCl salt in dichloromethane/N,N-dimethylformamide (10:3, 13 mL) was added 2S-(3-tert-butyl-ureido)-3,3-dimethyl-butyric acid (64 mgs, 0.28 mmol), O (7 azabenzotriazol 1 yl) 1,1,3,3 tetramethyl-uronium hexafluorophosphate (HATU) (128 mg, 0.34 mmol) and diisopropylethylamine (0.15 mL, 0.84 mmol). After 1 hour at room temperature, the reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure Step 6

The crude product was then dissolved in dry dichloromethane (10.0 mL) and Dess-Martin periodinane (154 mgs, 0.364 mmol) was added. After stirring at room temperature for 1 hour, the reaction mixture was quenched with 0.26M sodium thiosulfate in saturated sodium bicarbonate and extracted with ethyl acetate (3×). The combined ethyl acetate layers were then washed with saturated sodium bicarbonate (2×), brine (1×) and dried over magnesium sulfate. The organic layer was then filtered, concentrated under reduced pressure, and purified by flash chromatography (65% ethyl acetate/hexane) to give (2S,4R)-1-((S)-2-(3-tert-butylureido)-3,3-dimethylbutanoyl)-N-((S)-1-cyclopropyl-4-(cyclopropylamino)-3,4-dioxobutan-2-yl)-4-(6-ethoxyisoquinolin-1-yloxy)-pyrrolidine-2-carboxamide (80.7 mg, 0.116 mmol, 42% yield) as white solid. $^1$H NMR: (DMSO) 8.67 (d, 1H, J=5.6 Hz); 8.26 (d, 1H, J=6.8 Hz); 8.06 (d, 1H, J=8.8 Hz); 7.89 (d, 1H, J=5.6 Hz); 7.24-7.22 (m, 1H); 7.01-6.98 (dd, 1H, J=2.4, 8.8 Hz); 5.90-5.85 (m, 2H); 5.65-5.62 (m, 1H); 5.06-5.01 (m, 1H); 4.53 (t, 1H, J=8.0 Hz); 4.26-4.23 (m, 1H); 4.16-4.08 (m, 3H); 3.84-3.80 (m, 1H); 2.69-2.65 (m, 1H); 2.11-2.04 (m, 1H); 1.64-1.57 (m, 1H); 1.35-1.29 (m, 3H); 1.15 (m, 9H); 0.91 (m, 9H); 0.89-0.81 (m, 3H); 0.61-0.48 (m, 4H); 0.36-0.27 (m, 2H). MS m/z 693 ($M^+$+H), 715 ($M^+$+Na), 691 ($M^+$−H).

Example 12

(2S,4R)-1-((S)-2-(3-tert-Butylureido)-3,3-dimethylbutanoyl)-N-((S)-1-(cyclopropylamino)-1,2-dioxohexan-3-yl)-4-(6-ethoxyisoquinolin-1-yloxy)-pyrrolidine-2-carboxamide

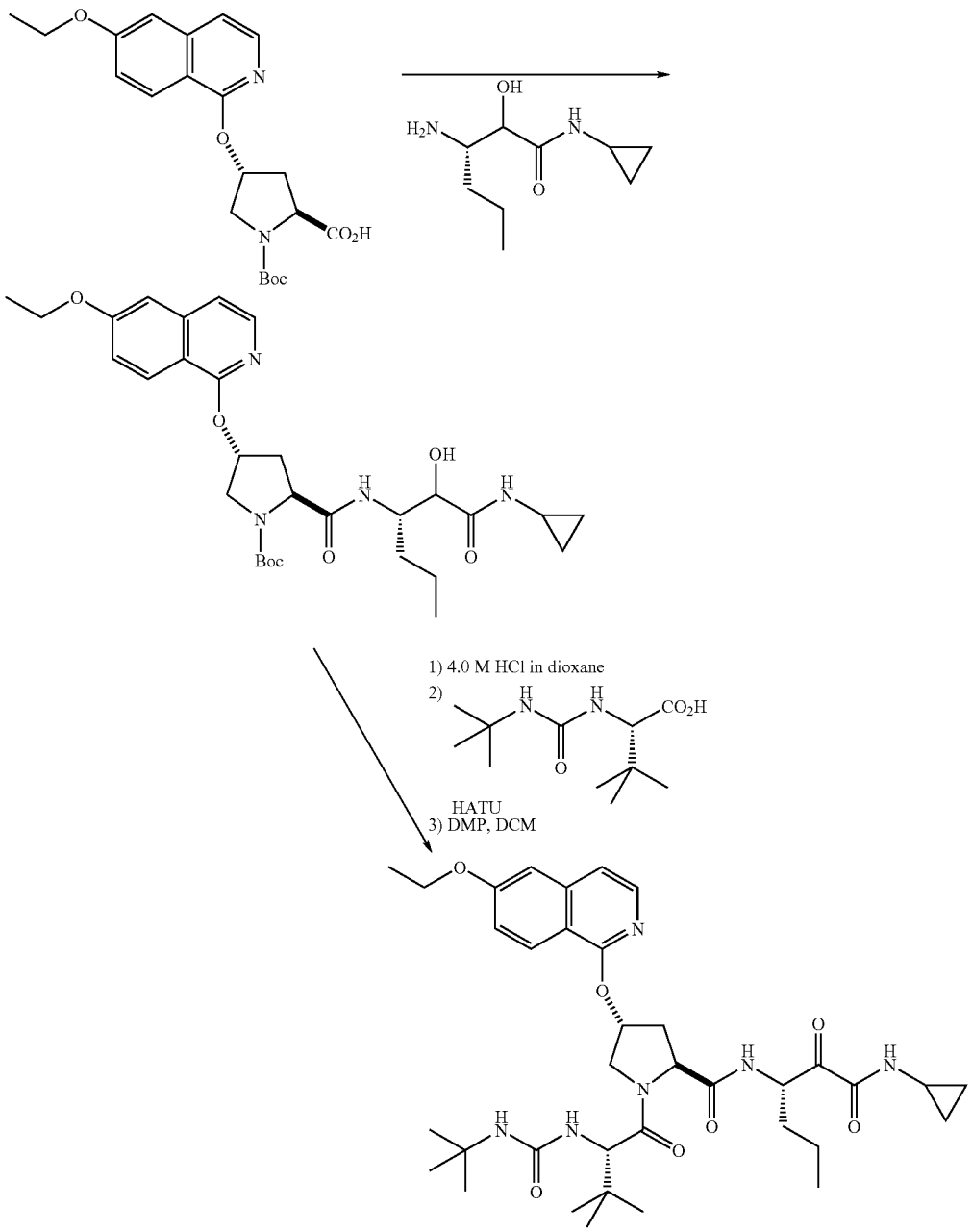

Step 1

To tert-butyl-(3S)-1-(cyclopropylamino)-1-oxohexan-3-ylcarbamate (75 mg, 0.26 mmol) was added 4.0 M HCl in dioxane (6.0 mL). After 1 hour, the reaction mixture was concentrated and dried to give the (3S)-3-amino-N-cyclopropyl-2-hydroxyhexanamide HCl salt as a white solid. To this salt in dichloromethane/N,N-dimethylformamide (10:3, 13 mL) was added (2S,4R)-1-(tert-butoxycarbonyl)-4-(6-ethoxyisoquinolin-1-yloxy)-pyrrolidine-2-carboxylic acid (106 mgs, 0.26 mmol), O (7 azabenzotriazol 1 yl) 1,1,3,3 tetramethyl-uronium hexafluorophosphate (HATU) (119 mg, 0.31 mmol) and diisopropylethylamine (0.15 mL, 0.78 mmol). After 1 hour at room temperature reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure to give (2S,4R)-1-(tert-butyl-2-((3S)-1-cyclopropylamino)-2-hydroxy-1-oxohexan-3-ylcarbamoyl)-4-(6-ethoxyisoquinolin-1-yloxy) pyrrolidine-1-carboxylate.

Step 2

To the above crude compound was added 4.0 M HCl in dioxane (10 mL). After 1 hour, the reaction mixture was concentrated and dried to give the corresponding deprotected HCl salt as a white solid. To this HCl salt in dichloromethane/N,N-dimethylformamide (10:3, 13 mL) was added (S)-2-(3-tert-butylureido)-3,3-dimethylbutanoic acid (60 mgs, 0.26 mmol), O (7 azabenzotriazol 1 yl) 1,1,3,3 tetramethyl-uronium hexafluorophosphate (HATU) (128 mg, 0.34 mmol) and diisopropylethylamine (0.15 mL, 0.84 mmol). After 1 hour at room temperature, the reaction mixture was diluted with ethyl acetate and washed with 1N HCl (2×), sodium bicarbonate (1×), and brine (1×). The ethyl acetate layer was dried over magnesium sulfate, filtered and evaporated to dryness.

Step 3

The crude product was then dissolved in dry dichloromethane (10.0 mL) and Dess-Martin periodinane (143 mgs, 0.338 mmol) was added. After stirring at room temperature for 1 hour reaction mixture was quenched with 0.26M sodium thiosulfate in saturated sodium bicarbonate and extracted with ethyl acetate (3×). The combined ethylacetate layers were then washed with saturated sodium bicarbonate (2×), brine (1×) and dried (MgSO$_4$). The organic layer was then filtered, concentrated and purified by flash chromatography (65% ethyl acetate/hexane) to give (2S,4R)-1-((S)-2-(3-tert-Butylureido)-3,3-dimethylbutanoyl)-N-((S)-1-(cyclopropylamino)-1,2-dioxohexan-3-yl)-4-(6-ethoxyisoquinolin-1-yloxy)-pyrrolidine-2-carboxamide (28) (75.7 mg, 0.11 mmol, 43% yield) as a white solid. $^1$H NMR: (DMSO-d$_6$) 8.75 (d, 1H, J=4.8 Hz); 8.28 (d, 1H, J=7.2 Hz); 8.13 (d, 1H, J=8.8 Hz); 7.96 (d, 1H, J=6.0 Hz); 7.31-7.29 (m, 2H); 7.10-7.06 (dd, 1H, J=2.4, 9.2 Hz); 5.94-5.92 (m, 2H); 5.72-5.70 (m, 1H); 5.04-5.00 (m, 1H); 4.58 (t, 1H, J=7.6 Hz); 4.34-4.30 (m, 1H); 4.23-4.17 (m, 3H); 3.90-3.86 (m, 1H); 2.79-2.74 (m, 1H); 2.54-2.51 (m, 1H); 2.18-2.11 (m, 1H); 1.77-1.70 (m, 1H); 1.48-1.38 (m, 3H); 1.15 (m, 9H); 0.91 (m, 9H); 0.89-0.86 (m, 3H); 0.69-0.59 (m, 4H). MS m/z 681 (M$^+$+H), 703 (M$^+$+Na), 679 (M$^+$−H).

Example 13

Synthesis of (2S,4R)-1-((S)-2-(3-tert-Butylureido)-3,3-dimethylbutanoyl)-N-((S)-1-cyclopropylamino)-1,2-dioxoheptan-3-yl)-4-(6-methoxyisoquinolin-1-yloxy)-pyrrolidine-2-carboxamide

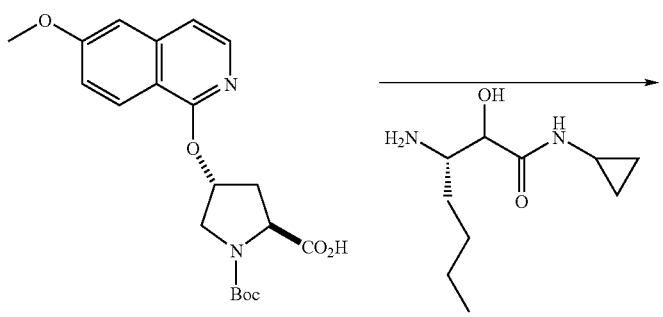

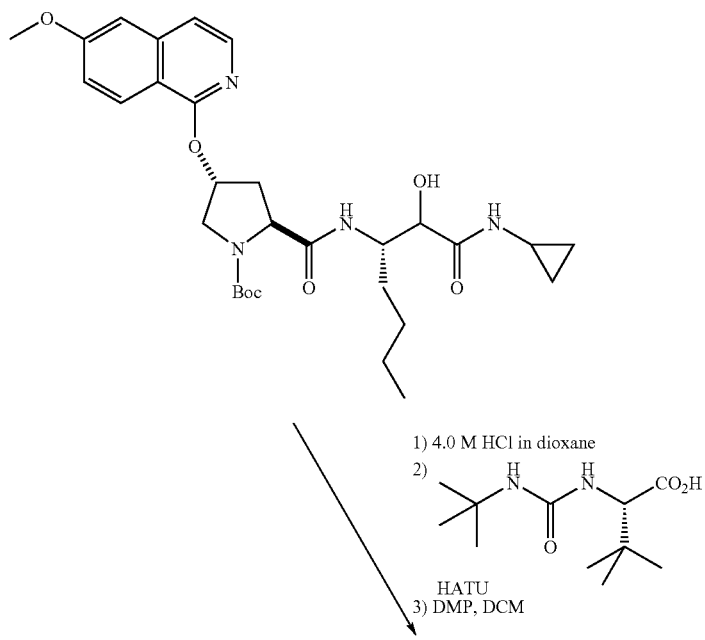

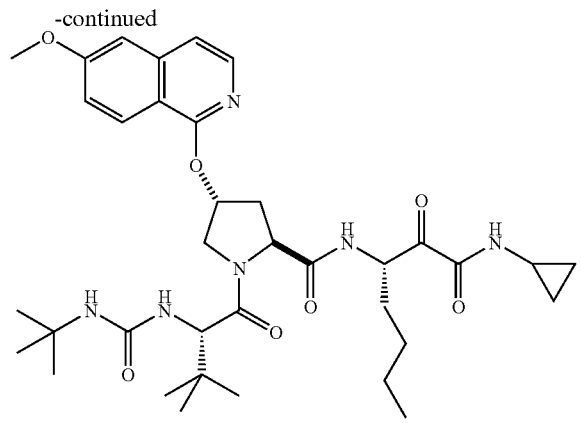

Step 1

To (3S)-3-amino-N-cyclopropyl-2-hydroxyheptamide HCl salt (96 mgs, 0.40 mmol) in dichloromethane/N,N-dimethylformamide (10:3, 13 mL) was added (2S,4R)-1-(tert-butoxycarbonyl)-4-(6-methoxy-isoquinolin-1-yloxy)pyrrolidine-2-carboxylic acid (157 mgs, 0.40 mmol), O (7 azabenzotriazol 1 yl) 1,1,3,3 tetramethyl-uronium hexafluorophosphate (HATU) (200 mg, 0.53 mmol) and diisopropylethylamine (0.35 mL, 2.0 mmol). After 1 hour at room temperature reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure to give (2S,4R)-tert-butyl-2-((3S)-1-(cyclopropylamino)-2-hydroxy-1-oxoheptan-3-ylcarbamoyl)-4-(6-methoxy-isoquinolin-1-yloxy)pyrrolidine-1-carboxylate. MS m/z 571 (M$^+$+H), 593 (M$^+$+Na), 569 (M$^+$–H), 471 (M$^+$–Boc).

Step 2

To the above crude compound was added 4.0 M HCl in dioxane (10 mL). After 1 hour at room temperature, the reaction mixture was concentrated and dried to give the corresponding HCl salt as a white solid. To this salt in dichloromethane/N,N-dimethylformamide (10:3, 13 mL) was added (S)-2-(3-tert-butylureido)-3,3-dimethylbutanoic acid (93 mgs, 0.40 mmol), O (7 azabenzotriazol 1 yl) 1,1,3,3 tetramethyl-uronium hexafluorophosphate (HATU) (200 mg, 0.53 mmol) and diisopropylethylamine (0.35 mL, 2.0 mmol). After 1 hour at room temperature reaction mixture was diluted with ethyl acetate and washed with 1N HCl (2×), sodium bicarbonate (1×), and brine (1×). The ethyl acetate layer was dried over magnesium sulfate, filtered and evaporated to dryness under reduced pressure. MS m/z 683 (M$^+$+H), 705 (M$^+$+Na), 681 (M$^+$–H).

Step 3

The crude product was then dissolved in dry dichloromethane (10.0 mL) and Dess-Martin periodinane (223 mgs, 0.53 mmol) was added. After stirring at room temperature for 2 hours, the reaction mixture was quenched with 0.26M sodium thiosulfate in saturated sodium bicarbonate and extracted with ethyl acetate (3×). The combined ethylacetate layers were then washed with saturated sodium bicarbonate (2×), brine (1×) and dried over magnesium sulfate. The organic layer was then filtered, concentrated under reduced pressure and purified by flash chromatography (45% ethyl acetate/hexane) to give (2S,4R)-1-((S)-2-(3-tert-butylureido)-3,3-dimethylbutanoyl)-N-((S)-1-cyclopropylamino)-1,2-dioxoheptan-3-yl)-4-(6-methoxyisoquinolin-1-yloxy)-pyrrolidine-2-carboxamide (30) (83.5 mg, 0.12 mmol, 31% yield) as white solid. $^1$H NMR: (DMSO) 8.74 (d, 1H, J=4.8 Hz); 8.27 (d, 1H, J=7.2 Hz); 8.15 (d, 1H, J=9.2 Hz); 7.97 (d, 1H, J=6.0 Hz); 7.33-7.31 (m, 2H); 7.10-7.08 (dd, 1H, J=2, 8.8 Hz); 5.96 (s, 1H); 5.94 (d, 1H, J=9.6 Hz); 5.71-5.69 (m, 1H); 5.02-4.98 (m, 1H); 4.60 (t, 1H, J=8.4 Hz); 4.34-4.22 (m, 1H); 4.23 (d, 1H, J=9.2 Hz); 3.91 (s, 3H); 3.90-3.87 (m, 1H); 2.78-2.73 (m, 1H); 2.54-2.51 (m, 1H); 2.17-2.11 (m, 1H); 1.77-1.72 (m, 1H); 1.43-1.33 (m, 5H); 1.20 (m, 9H); 0.95 (m, 9H); 0.88-0.85 (m, 5H); 0.69-0.58 (m, 4H). MS m/z 681 (M$^+$+H), 703 (M$^+$+Na), 680 (M$^+$–H).

Example 14

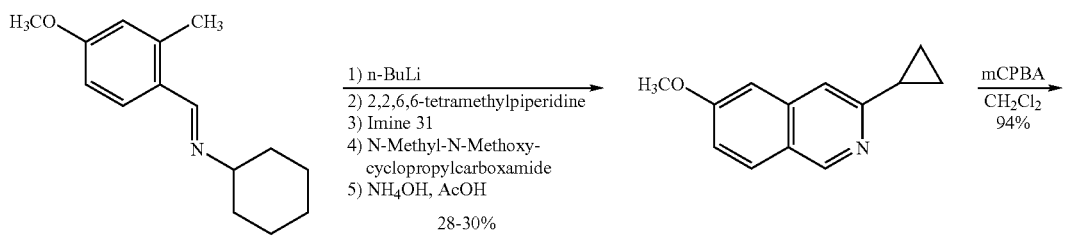

-continued
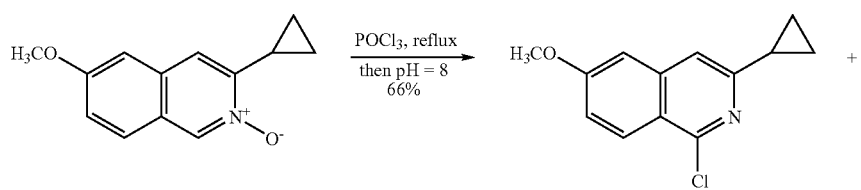
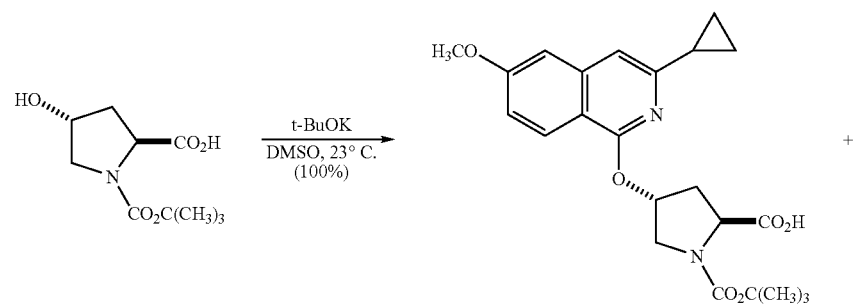
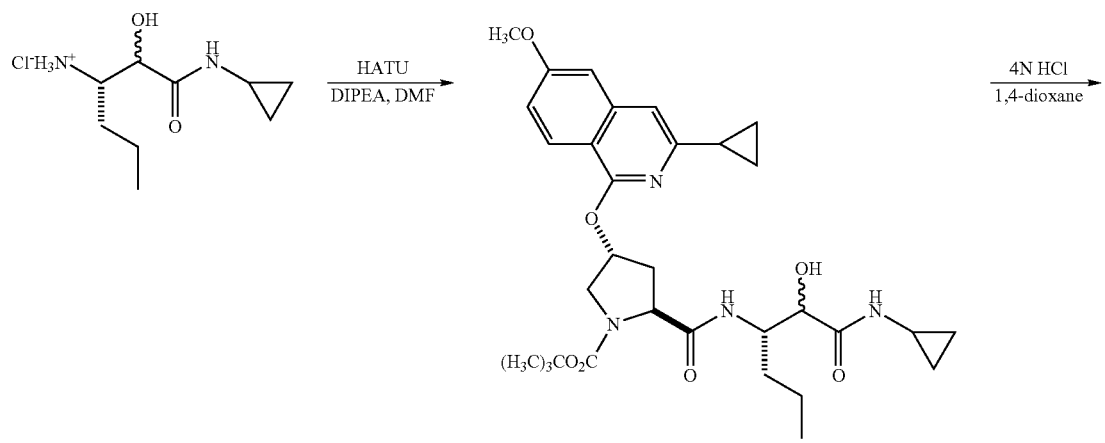
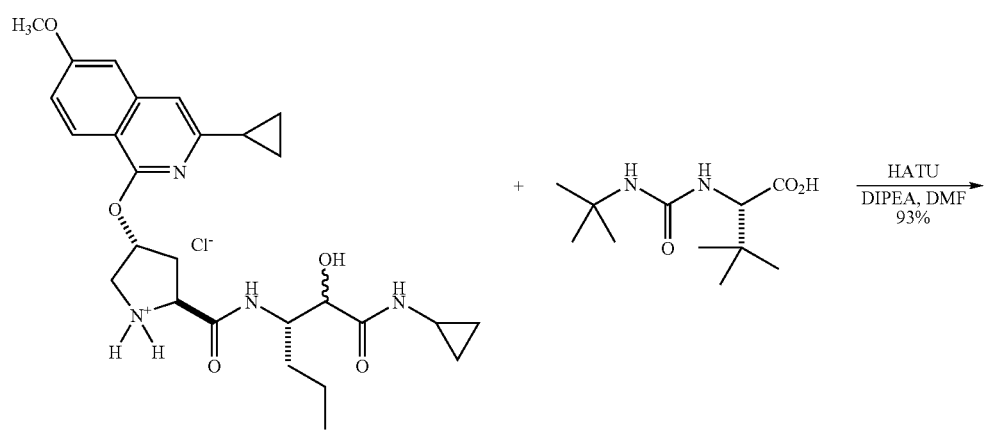

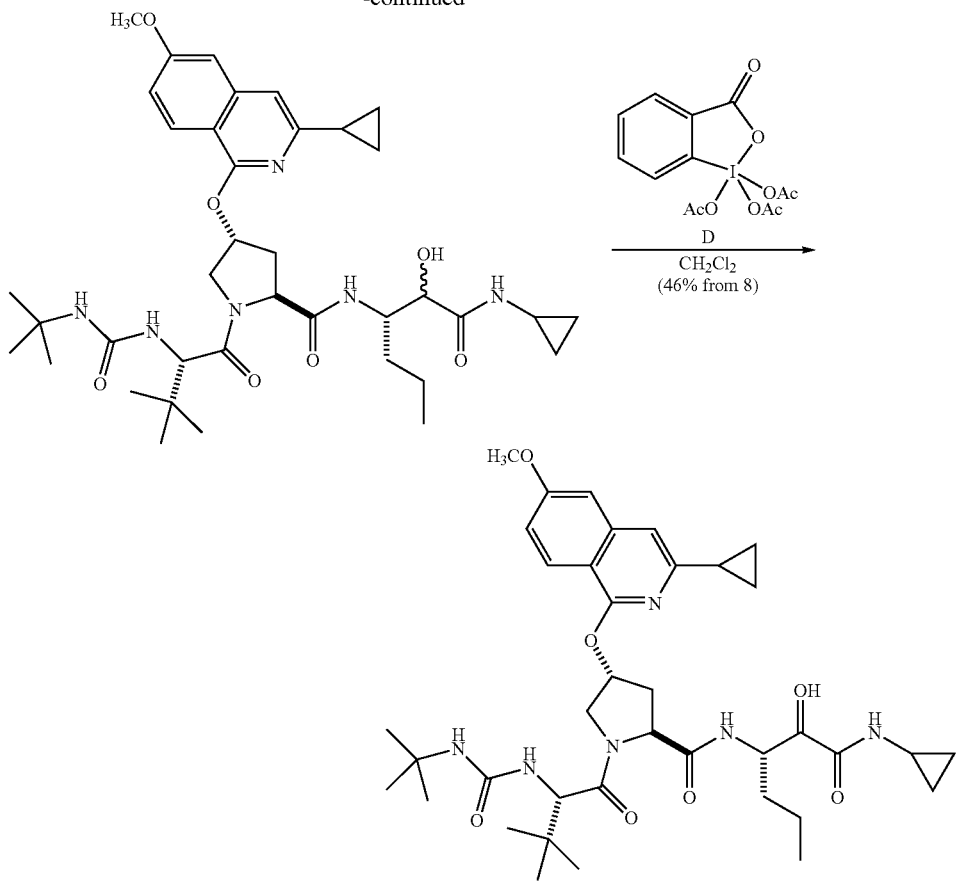

Step 1

3-Cyclopropyl-6-methoxyisoquinoline. Lithium tetramethylpiperidide was prepared by the treatment of 2,2,6,6-tetramethylpiperidine (1.0 g; 7.0 mmol) in tetrahydrofuran (17 mL) with n-BuLi (1.6 M in hexanes; 8.0 mmol) dropwise at −15° C. After 15 minutes at −15° C., a solution of N-(4-methoxy-2-methylbenzylidene)-cyclohexanamine (660 mg; 2.86 mmol) in tetrahydrofuran (3 mL) was added dropwise to give a purple solution. The reaction mixture was allowed to warm to 0° C. over a 20 minute period, then a solution of N-methyl-N-methoxycyclopropanecarboxamide (630 mg: 4.4 mmol) in tetrahydrofuran (2 mL) was added in one portion while at 0° C. The reaction mixture was kept at room temperature for 30 minutes and then added to saturated aqueous ammonium chloride. The solution was extracted with diethyl ether and the organic phase was washed with brine, dried and concentrated under reduced pressure.

The residue was dissolved in concentrated ammonia (15 mL), treated with acetic acid (1 mL) then heated to reflux. The mixture was diluted with water, and the resulting solution extracted with diethyl ether. The ether extracts were washed with water, brine, then dried and concentrated under reduced pressure. Chromatography (SiO$_2$; 4:1 hexane/ethyl acetate) provided 160 mg (28%) of 3-cyclopropyl-6-methoxyisoquinoline. Execution of the process with 1.5 g of the imine provided 400 mg (30%) of 3-cyclopropyl-6-methoxyisoquinoline.

Step 2

1-Chloro-3-cyclopropyl-6-methoxy-isoquinoline. 3-Cyclopropyl-6-methoxyisoquinoline was dissolved in dichloromethane (8 mL) and cooled to 0° C. This solution was treated with a solution of m-chloroperbenzoic acid (mCPBA; 412 mg; 2.4 mmol) in dichloromethane (8 mL) and the mixture was stirred for 2 hours at room temperature. The reaction mixture was quenched with dimethyl sulfide (100 µL) and stirred for another 15 minutes. The mixture was treated with saturated aqueous sodium bicarbonate (20 mL) and the layers were separated. The aqueous phase was extracted with dichloromethane and the combined organic phases were dried over magnesium sulfate, concentrated under reduced pressure, and chromatographed (SiO$_2$; 10% methanol in methylene chloride) to give 405 mg (94%) of the N-oxide of 3-cyclopropyl-6-methoxyisoquinoline.

The N-oxide was dissolved in dichloromethane (5 mL) and 1 mL of phosphorus oxychloride was added. The mixture was heated at reflux for 2 hours, cooled and poured onto ice. The mixture was treated with ammonium hydroxide to pH 8, and the resulting solution was extracted with ethyl acetate. The organic phase was washed with brine, dried and concentrated under reduced pressure. The crude product was purified by chromatography (SiO$_2$; Hexane/ethyl acetate, 4:1) to provide 310 mg (66% overall) of 1-chloro-3-cyclopropyl-6-methoxy-isoquinoline.

Step 3

(2S,4R)-tert-butyl 4-(3-cyclopropyl-6-methoxyisoquinolin-1-yloxy)-2-((S)-1-(cyclopropylamino)-2-hydroxy-1-oxohexan-3-ylcarbamoyl)pyrrolidine-1-carboxylate N-BOC-4-hydroxy-L-proline (192 mg; 830 µmol) was dissolved in dimethylsulfoxide (5 mL) at room temperature, then potassium t-butoxide (270 mg; 2.4 mmol) was added. The resulting solution was stirred at room temperature for 1.5 hours, then 1-chloro-3-cyclopropyl-6-methoxyisoquinoline (4; 192 mg; 820 μmol) was added. The resulting solution was stirred overnight, diluted with 15 mL of 5% aqueous citric acid, and extracted with ethyl acetate. The organic phase was washed with brine, dried and concentrated under reduced pressure to give 375 mg of the crude arylether of N-BOC-4-hydroxy-L-proline.

The crude aryl ether was dissolved in N,N-dimethylformamide (2 mL) and (O-7-azabenzotriazol-1-yl)-1,1,3,3-tetramethyluronium hexafluorophosphate (O(7 azabenzotriazol 1 yl) 1,1,3,3 tetramethyl-uronium hexafluorophosphate (HATU); 380 mg; 830 μmol) was added followed by 3-(S)-amino-2-(RS)-hydroxyhexanoic acid-N-cyclopropylcarboxamide hydrochloride (190 mg; 830 μmol) and N,N-diisopropylethylamine (800 μL). The resulting mixture was stirred overnight then diluted with water. The resulting precipitate was filtered, washed with water and dried to give 460 mg (93%) of (2S,4R)-tert-butyl 4-(3-cyclopropyl-6-methoxyisoquinolin-1-yloxy)-2-((S)-1-(cyclopropylamino)-2-hydroxy-1-oxohexan-3-ylcarbamoyl)pyrrolidine-1-carboxylate.

Step 4

(2S,4R)-1-((S)-2-(3-tert-butylureido)-3,3-dimethylbutanoyl)-4-(3-cyclopropyl-6-methoxyisoquinolin-1-yloxy)-N-((S)-1-(cyclopropylamino)-2-hydroxy-1-oxohexan-3-yl)pyrrolidine-2-carboxamide The compound from step 3 was dissolved in 4N HCl in 1,4-dioxane (2 mL) and stirred 1 hour at room temperature. The reaction mixture was concentrated under reduced pressure and the residue dissolved in N,N-dimethylformamide (2 mL). The solution was treated with (S)-2-(3-tert-butylureido)-3,3-dimethylbutanoic acid (100 mg; 440 μmol), O (7 azabenzotriazol 1 yl) 1,1,3,3 tetramethyl-uronium hexafluorophosphate (HATU) (200 mg; 520 μmol), and diisopropylethylamine (800 mL). The reaction mixture was diluted with water and the resulting precipitate was filtered, washed with water and dried to give 250 mg (80%) of the corresponding 2-hydroxycarboxamide. The solid was dissolved in dichloromethane (20 mL) and treated with 1,1,1-tris(acetyloxy)-1,1-dihydro-1,2-benziodoxol-3-(1H)-one (220 mg; 660 μmol). The reaction mixture was stirred for 2 hours at room temperature. The solution was diluted with diethyl ether (40 mL) followed by the addition of saturated aqueous sodium thiosulfate (10 mL) and 10 mL of aqueous sodium bicarbonate (10 mL). The biphasic mixture was stirred for 10 minutes and the layers were separated. The organic phase was washed with brine, dried and concentrated under reduced pressure. The residue was purified by chromatography (SiO$_2$; Hexane/ethyl acetate, 1:1) then the isolated material was lyophilized from acetonitrile and 0.01% aq. HCl to give 150 mg (46%) of (2S,4R)-1-((S)-2-(3-tert-butylureido)-3,3-dimethylbutanoyl)-4-(3-cyclopropyl-6-methoxyisoquinolin-1-yloxy)-N-((S)-1-(cyclopropylamino)-2-hydroxy-1-oxohexan-3-yl)pyrrolidine-2-carboxamide. Mass Spec (M+Na) 705.

Example 15

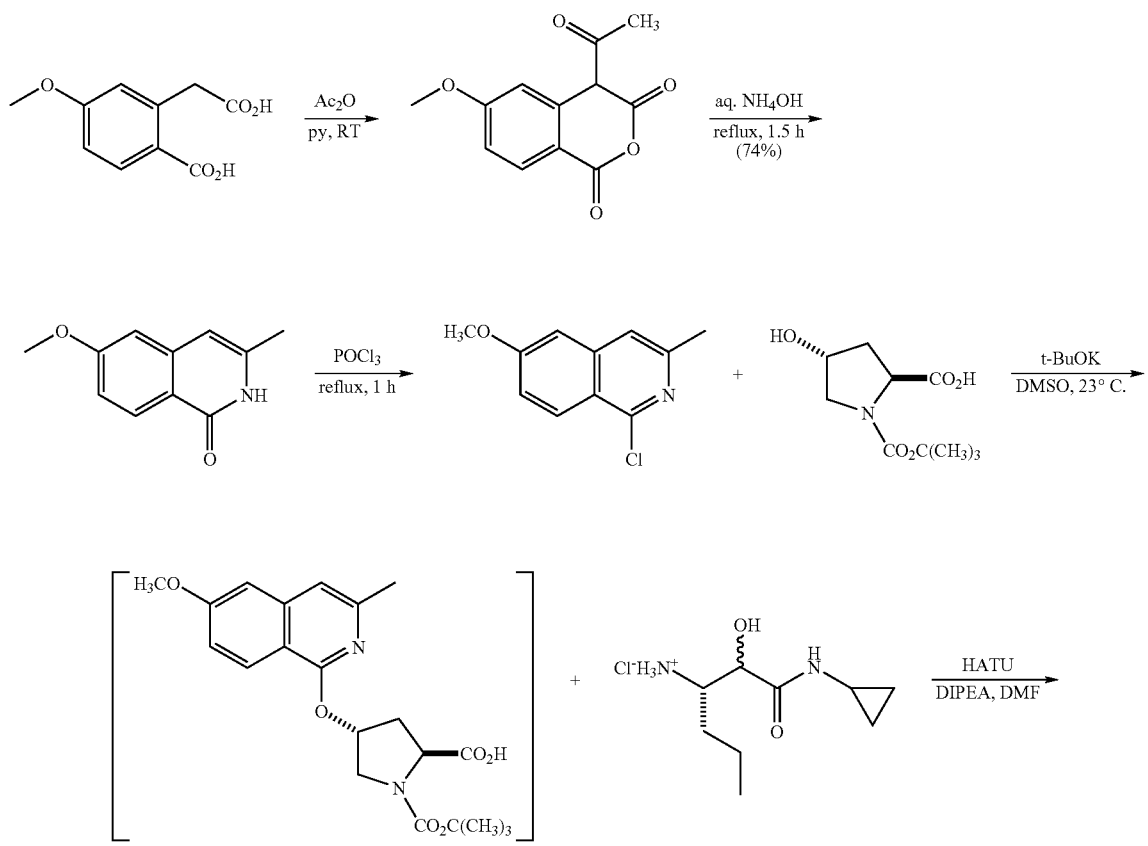

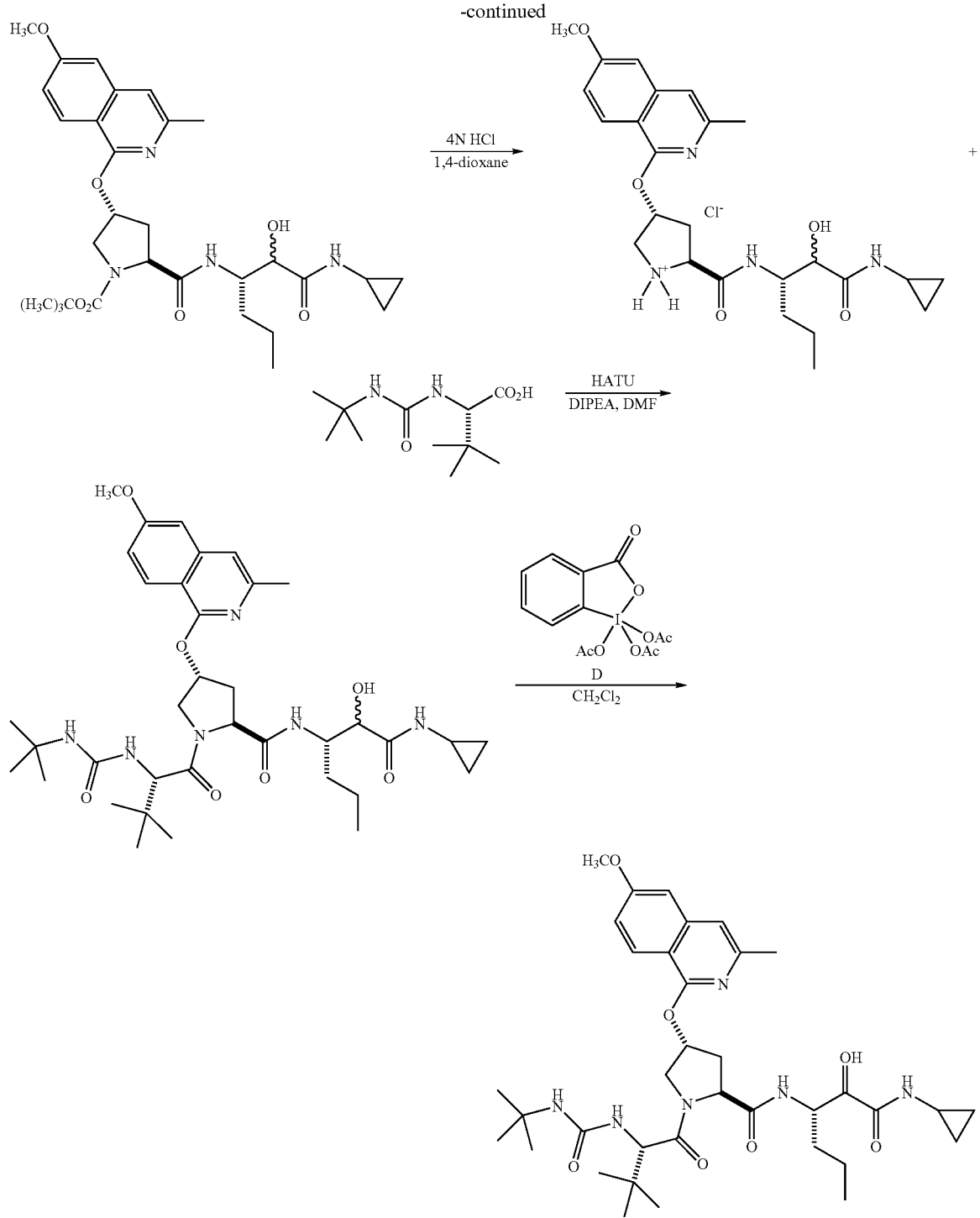

Step 1

4-Acetyl-6-methoxyisochroman-1,3-dione. Following a literature procedure (*Ind. J. Chem. Sec. B*, 1986, 25B, 640-643), 2-carboxymethyl-4-methoxybenzoic acid (1.0 g; 4.8 mmol) was dissolved in a mixture of pyridine (1.4 mL) and acetic anhydride (8.6 mL; 9.3 g; 91 mmol) then stirred for 3 hours, during which time a solid had formed. The suspension was diluted with diethyl ether, filtered and the filter cake washed with diethyl ether. Yield: 905 mg (81%) of 4-acetyl-6-methoxyisochroman-1,3-dione.

Step 2

6-Methoxy-3-methylisoquinolin-1(2H)-one. The cyclic anhydride of step 1 (405 mg; 1.73 mmol) was dissolved in aqueous ammonium hydroxide, and heated at reflux for 1.5 hours. The mixture was cooled to room temperature and the solid was filtered then dried overnight to give 270 mg (74%) of 6-methoxy-3-methylisoquinolin-1(2H)-one.

Step 3

1-Chloro-6-methoxy-3-methylisoquinoline. The isoquinoline of step 2 was dissolved in phosphorus oxychloride (2.5 mL) and heated at reflux for 1 hour. The excess phosphorus oxychloride was removed under reduced pressure and the residue was dissolved in chloroform. The resulting solution was washed with 1N aq. sodium hydroxide, water and brine. Evaporation of the solvent under reduced pressure gave crude 1-chloro-6-methoxy-3-methylisoquinoline, which was used directly in the next step.

Step 4

(2S,4R)-1-(tert-butoxycarbonyl)-4-(6-methoxy-3-methylisoquinolin-1-yloxy)pyrrolidine-2-carboxylic acid. N-BOC-4-hydroxy-L-proline (A; 281 mg; 1.21 mmol) was dissolved in dimethylsulfoxide (3 mL) at room temperature then potassium t-butoxide (270 mg; 2.4 mmol) was added. The resulting solution was stirred at room temperature for 2 hours, then cooled to 0° C. A solution of 1-chloro-6-methoxy-3-methylisoquinoline in dimethylsulfoxide (3 mL) was then added dropwise to the cold solution, followed by t-BuOK, and the mixture was allowed to warm to room temperature. The solution was stirred for 16 hours. The reaction mixture was acidified to pH=4 with 5% aq. citric acid. The solution was extracted with ethyl acetate and the organic phase washed with water followed by brine. The organic phase was concentrated under reduced pressure to give (2S,4R)-1-(tert-butoxycarbonyl)-4-(6-methoxy-3-methylisoquinolin-1-yloxy)pyrrolidine-2-carboxylic acid.

Step 5

(2S,4R)-tert-butyl 2-((S)-1-(cyclopropylamino)-2-hydroxy-1-oxohexan-3-ylcarbamoyl)-4-(6-methoxy-3-methylisoquinolin-1-yloxy)pyrrolidine-1-carboxylate. The compound produced in step 4 (196 mg; 487 μmol) was converted to (2S,4R)-tert-butyl 2-((S)-1-(cyclopropylamino)-2-hydroxy-1-oxohexan-3-ylcarbamoyl)-4-(6-methoxy-3-methylisoquinolin-1-yloxy)pyrrolidine-1-carboxylate by reaction with 3-(S)-amino-2-(RS)-hydroxyhexanoic acid-N-cyclopropylcarboxamide hydrochloride as previously described in Reaction Scheme 14, step 3, above, to provide (2S,4R)-tert-butyl 2-((S)-1-(cyclopropylamino)-2-hydroxy-1-oxohexan-3-ylcarbamoyl)-4-(6-methoxy-3-methylisoquinolin-1-yloxy)pyrrolidine-1-carboxylate. (210 mg; 77% yield), which was used in the subsequent step without further purification.

Step 6

(2S,4R)-1-((S)-2-(3-tert-butylureido)-3,3-dimethylbutanoyl)-N-((S)-1-(cyclopropylamino)-1,2-dioxohexan-3-yl)-4-(6-methoxy-3-methylisoquinolin-1-yloxy)pyrrolidine-2-carboxamide. The compound produced in step 5 (210 mg; 368 μmol) was converted to the corresponding HCl salt as previously described. The HCl salt was then converted to the tripeptide by reaction with (S)-2-(3-tert-butylureido)-3,3-dimethylbutanoic acid and O (7 azabenzotriazol 1 yl) 1,1,3,3 tetramethyl-uronium hexafluorophosphate (HATU) using the same conditions previously described. The compound thus produced was converted to (2S,4R)-1-((S)-2-(3-tert-butylureido)-3,3-dimethylbutanoyl)-N-((S)-1-(cyclopropylamino)-1,2-dioxohexan-3-yl)-4-(6-methoxy-3-methylisoquinolin-1-yloxy)pyrrolidine-2-carboxamide employing Dess-Martin periodinane reagent in dichloromethane as previously described. Purification of the crude product by chromatography (SiO₂; 45% ethyl acetate in hexane) provided 85 mg of (2S,4R)-1-((S)-2-(3-tert-butylureido)-3,3-dimethylbutanoyl)-N-((S)-1-(cyclopropylamino)-1,2-dioxohexan-3-yl)-4-(6-methoxy-3-methylisoquinolin-1-yloxy)pyrrolidine-2-carboxamide (34%). Mass Spec (M+) 680.

Example 16

Synthesis of (2S,4R)-1-((S)-2-(3-tert-butylureido)-3,3-dimethylbutanoyl)-N-((S)-1-(cyclopropylamino)-1,2-dioxohexan-3-yl)-4-(2-(pyridin-2-yl)thieno[2,3-d]pyrimidin-4-yloxy)pyrrolidine-2-carboxamide (62)

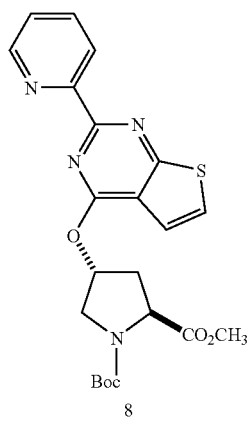

8

4.0 M HCl in dioxane

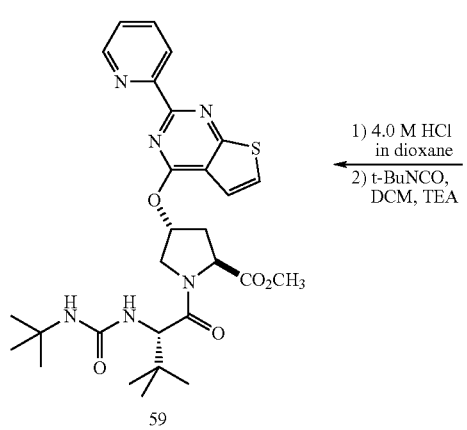
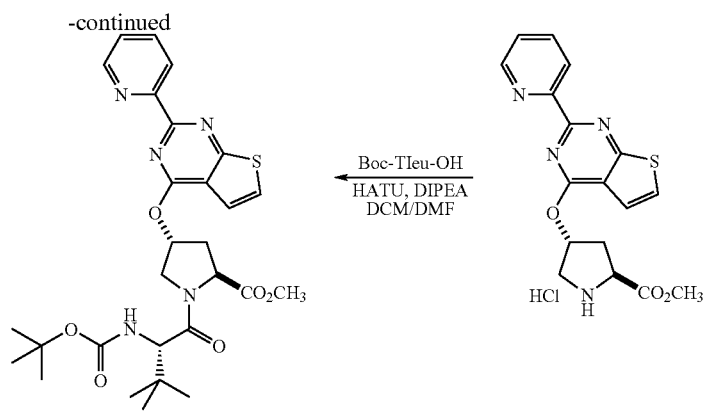
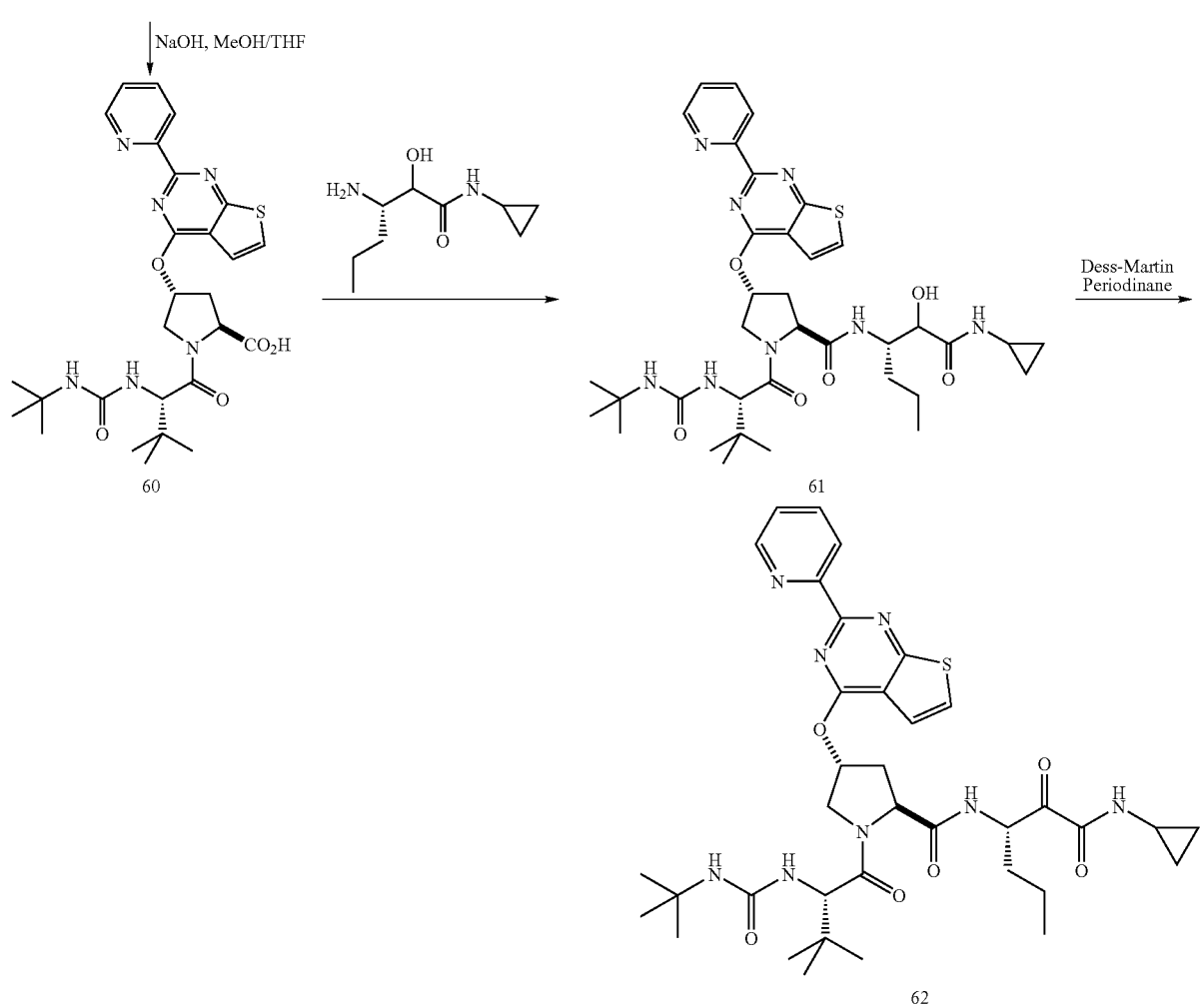

Step 1

(2S,4R)-1-tert-butyl 2-methyl 4-(2-(pyridin-2-yl)thieno[2,3-d]pyrimidin-4-yloxy)pyrrolidine-1,2-dicarboxylate (8) (1 mmol, prepared as shown in Reaction Scheme 8 and described in WO 2006/043145) was converted into (57) by reaction with 4.0 M HCl in dioxane (6.0 mL) in dichloromethane (2 mL). After 1 hour, evaporation of the reaction mixture to dryness gave (2S,4R)-methyl 4-(2-(pyridin-2-yl)thieno[2,3-d]pyrimidin-4-yloxy)pyrrolidine-2-carboxylate hydrochloride (57).

Step 2

(2S,4R)-methyl 4-(2-(pyridin-2-yl)thieno[2,3-d]pyrimidin-4-yloxy)pyrrolidine-2-carboxylate hydrochloride (57) was converted into (58) by dissolving 0.165 mmol of (57) in dichloromethane/dimethylformamide (2.0 mL, 1:1) and adding Boc-L-tert-Leu-OH (0.165 mmol), O-(7-azabenzotriazole-1-yl)-N,N,N,N'-tetramethyluronium hexafluorophosphate (O (7 azabenzotriazol 1 yl) 1,1,3,3 tetramethyluronium hexafluorophosphate (HATU)) (0.182 mmol) and diisopropylethylamine (0.5 mmol), and stirring the mixture at room temperature for 16 hours. After diluting the reaction mixture with ethyl acetate, and washing with 1N hydrochloric acid, saturated sodium bicarbonate, and brine, separating the ethyl acetate layer, drying over magnesium sulfate, filtering and evaporating to dryness, (2S,4R)-methyl 1-((S)-2-(tert-butoxycarbonylamino)-3,3-dimethylbutanoyl)-4-(2-(pyridin-2-yl)thieno[2,3-d]pyrimidin-4-yloxy)pyrrolidine-2-carboxylate (58) was isolated.

Step 3

(2S,4R)-methyl 1-((S)-2-(tert-butoxycarbonylamino)-3,3-dimethylbutanoyl)-4-(2-(pyridin-2-yl)thieno[2,3-d]pyrimidin-4-yloxy)pyrrolidine-2-carboxylate (58) was converted to (59) by first treating the crude material prepared in Step 2 with 4.0 M HCl in dioxane (3.0 mL) in dichloromethane (2 mL) to remove the t-Boc group and then, after evaporating the solvents under reduced pressure, reacting the resultant crude product with triethylamine (0.413 mmol) and tert-butylisocyanate (0.165 mmol) in dichloromethane (3.0 mL) at room temperature for 16 hours. After aqueous/organic work up (diluting with dichloromethane and washing with 1N hydrochloric acid, saturated sodium bicarbonate, and brine) and evaporating to dryness under reduced pressure, (2S,4R)-methyl 1-((S)-2-(3-tert-butylureido)-3,3-dimethylbutanoyl)-4-(2-(pyridin-2-yl)thieno[2,3-d]pyrimidin-4-yloxy)pyrrolidine-2-carboxylate (59) was isolated.

Step 4

(2S,4R)-methyl 1-((S)-2-(3-tert-butylureido)-3,3-dimethylbutanoyl)-4-(2-(pyridin-2-yl)thieno[2,3-d]pyrimidin-4-yloxy)pyrrolidine-2-carboxylate (59) was converted into (60) by treatment with methanol (6.0 mL), tetrahydrofuran (3.0 mL) and 1N sodium hydroxide (6 mL) for 1 hour at room temperature. (2S,4R)-1-((S)-2-(3-tert-butylureido)-3,3-dimethylbutanoyl)-4-(2-(pyridin-2-yl)thieno[2,3-d]pyrimidin-4-yloxy)pyrrolidine-2-carboxylic acid (60) was isolated by aqueous/organic work up (concentrating the reaction mixture, acidifying with 1N hydrochloric acid, extracting into ethyl acetate, washing with brine, drying over magnesium sulfate and evaporating to dryness under reduced pressure).

Step 5

(2S,4R)-1-((S)-2-(3-tert-butylureido)-3,3-dimethylbutanoyl)-4-(2-(pyridin-2-yl)thieno[2,3-d]pyrimidin-4-yloxy)pyrrolidine-2-carboxylic acid (60) (1 mmol) was coupled with (3S)-3-amino-N-cyclopropyl-2-hydroxyhexanamide (1 mmol, as prepared in Reference A) in the presence of O (7 azabenzotriazol 1 yl) 1,1,3,3 tetramethyl-uronium hexafluorophosphate (HATU) (1.2 mmol) and diisopropylethylamine (4 mmol) in dichloromethane and N,N-dimethylformamide to give (2S,4R)-1-((S)-2-(3-tert-butylureido)-3,3-dimethylbutanoyl)-N-((3S)-1-(cyclopropylamino)-2-hydroxy-1-oxohexan-3-yl)-4-(2-(pyridin-2-yl)thieno[2,3-d]pyrimidin-4-yloxy)pyrrolidine-2-carboxamide (61) as a crude solid after aqueous/organic extractive work up.

Step 6

(2S,4R)-1-((S)-2-(3-tert-butylureido)-3,3-dimethylbutanoyl)-N-((3S)-1-(cyclopropylamino)-2-hydroxy-1-oxohexan-3-yl)-4-(2-(pyridin-2-yl)thieno[2,3-d]pyrimidin-4-yloxy)pyrrolidine-2-carboxamide (61) (1 mmol) was oxidized with Dess-Martin periodinane (1.2 mmol) in dry dichloromethane, to provide (2S,4R)-1-((S)-2-(3-tert-butylureido)-3,3-dimethylbutanoyl)-N-((S)-1-(cyclopropylamino)-1,2-dioxohexan-3-yl)-4-(2-(pyridin-2-yl)thieno[2,3-d]pyrimidin-4-yloxy)pyrrolidine-2-carboxamide (62) after aqueous/organic work up and purification of the crude product using silica gel chromatography.

Example 17

Similarly, following the procedures of Example 16, but starting with (2S,4R)-1-tert-butyl 2-methyl 4-(2-(pyridin-2-yl)thieno[3,2-d]pyrimidin-4-yloxy)pyrrolidine-1,2-dicarboxylate (39) (prepared as shown in Reaction Scheme 9 and described in WO 2006/043145) was converted into (2S,4R)-1-((S)-2-(3-tert-butylureido)-3,3-dimethylbutanoyl)-N-((S)-1-(cyclopropylamino)-1,2-dioxohexan-3-yl)-4-(2-(pyridin-2-yl)thieno[3,2-d]pyrimidin-4-yloxy)pyrrolidine-2-carboxamide (63).

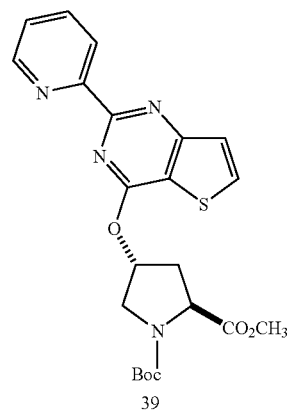

39

4.0 M HCl in dioxane

-continued
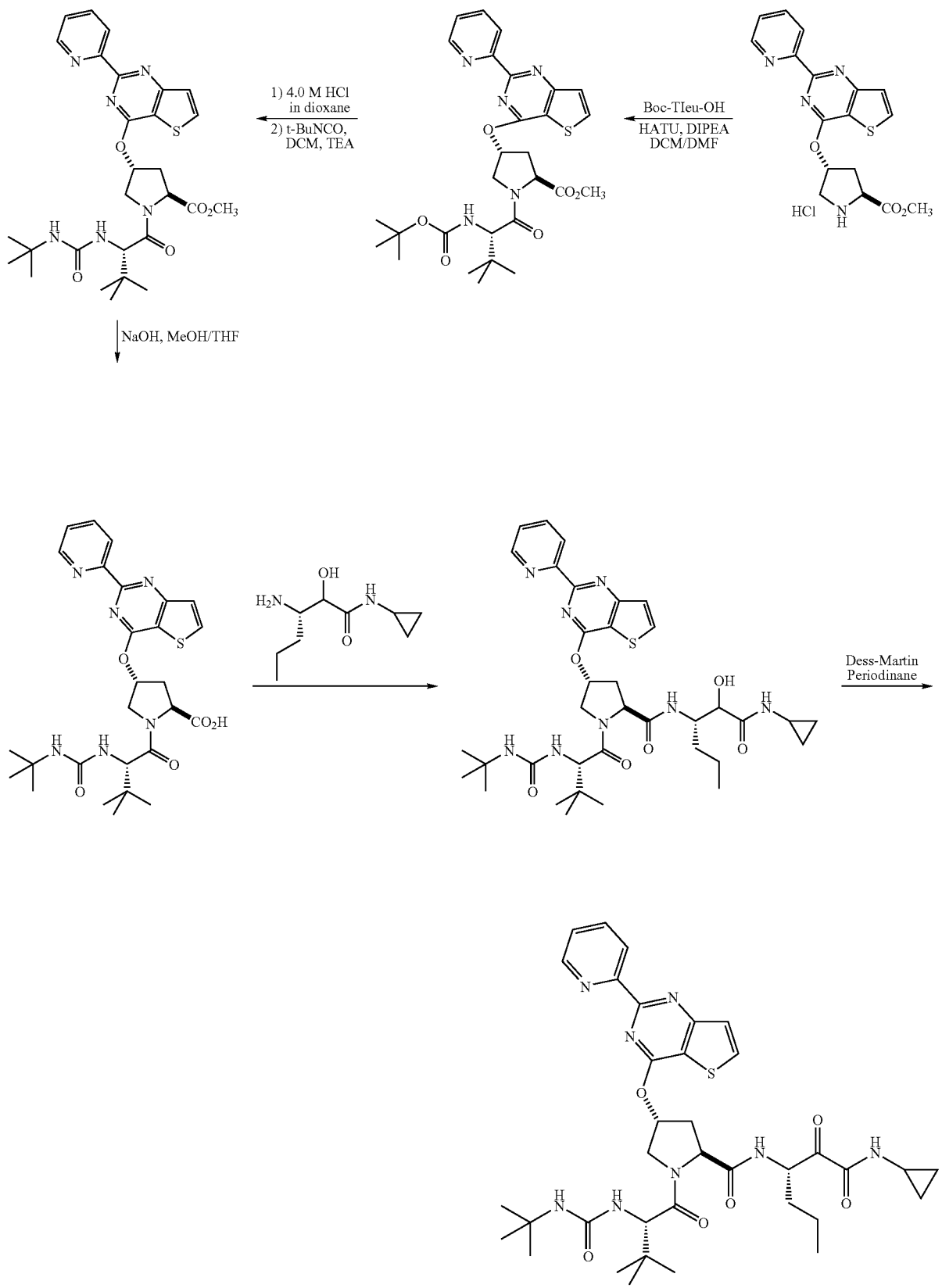

Example 18

Similarly, following the procedures of Example 16, but starting with (2S,4R)-1-tert-butyl 2-methyl 4-(2-(1,3-dimethyl-1H-pyrazol-5-yl)thieno[3,2-d]pyrimidin-4-yloxy)pyrrolidine-1,2-dicarboxylate (45) (as prepared in Reaction Scheme 10 and described in WO 2006/043145) was converted into (2S,4R)-1-((S)-2-(3-tert-butylureido)-3,3-dimethylbutanoyl)-N-((S)-1-(cyclopropylamino)-1,2-dioxohexan-3-yl)-4-(2-(1,3-dimethyl-1H-pyrazol-5-yl)thieno[3,2-d]pyrimidin-4-yloxy)pyrrolidine-2-carboxamide (64).

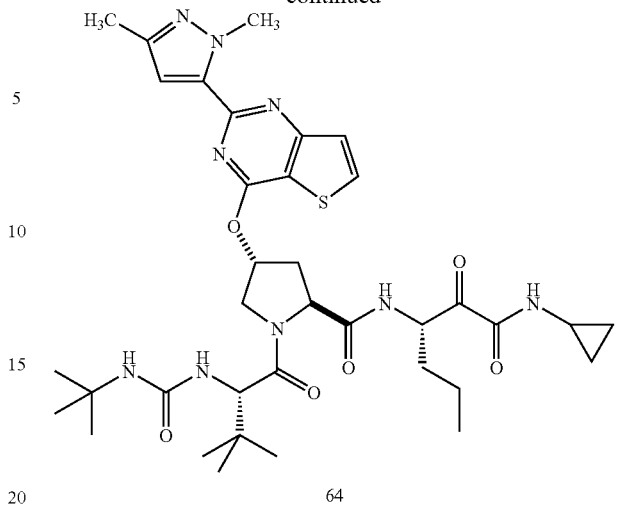

64

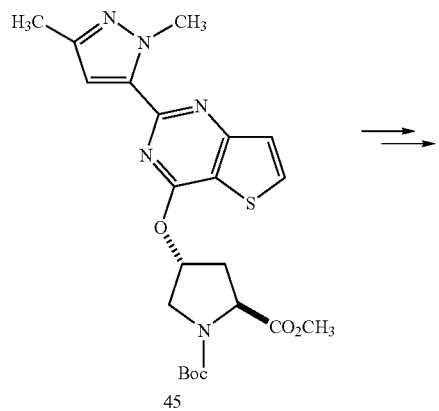

45

Example 19

Similarly, following the procedures of Example 16, but starting with (2S,4R)-1-tert-butyl 2-methyl 4-(5-(pyridin-2-yl)thieno[3,2-b]pyridin-7-yloxy)pyrrolidine-1,2-dicarboxylate (33) (as prepared in Reaction Scheme 7 and described in WO 2006/043145) was converted into (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(5-(pyridin-2-yl)thieno[3,2-b]pyridin-7-yloxy)pyrrolidine-2-carboxamide (65) by using (3S)-3-amino-4-cyclobutyl-N-cyclopropyl-2-hydroxybutanamide (as prepared in Reference B) in Step 5.

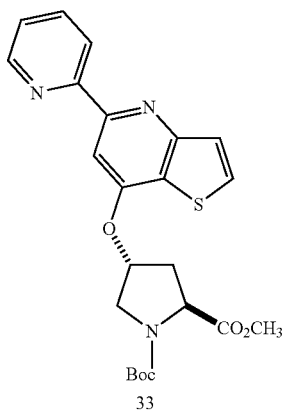

33

↘ 4.0 M HCl in dioxane

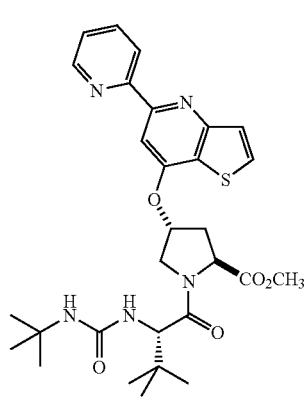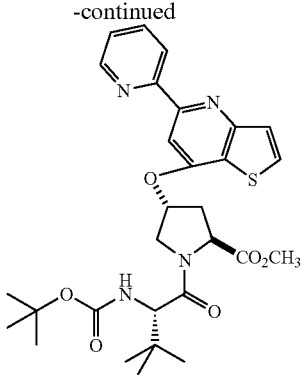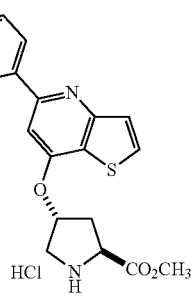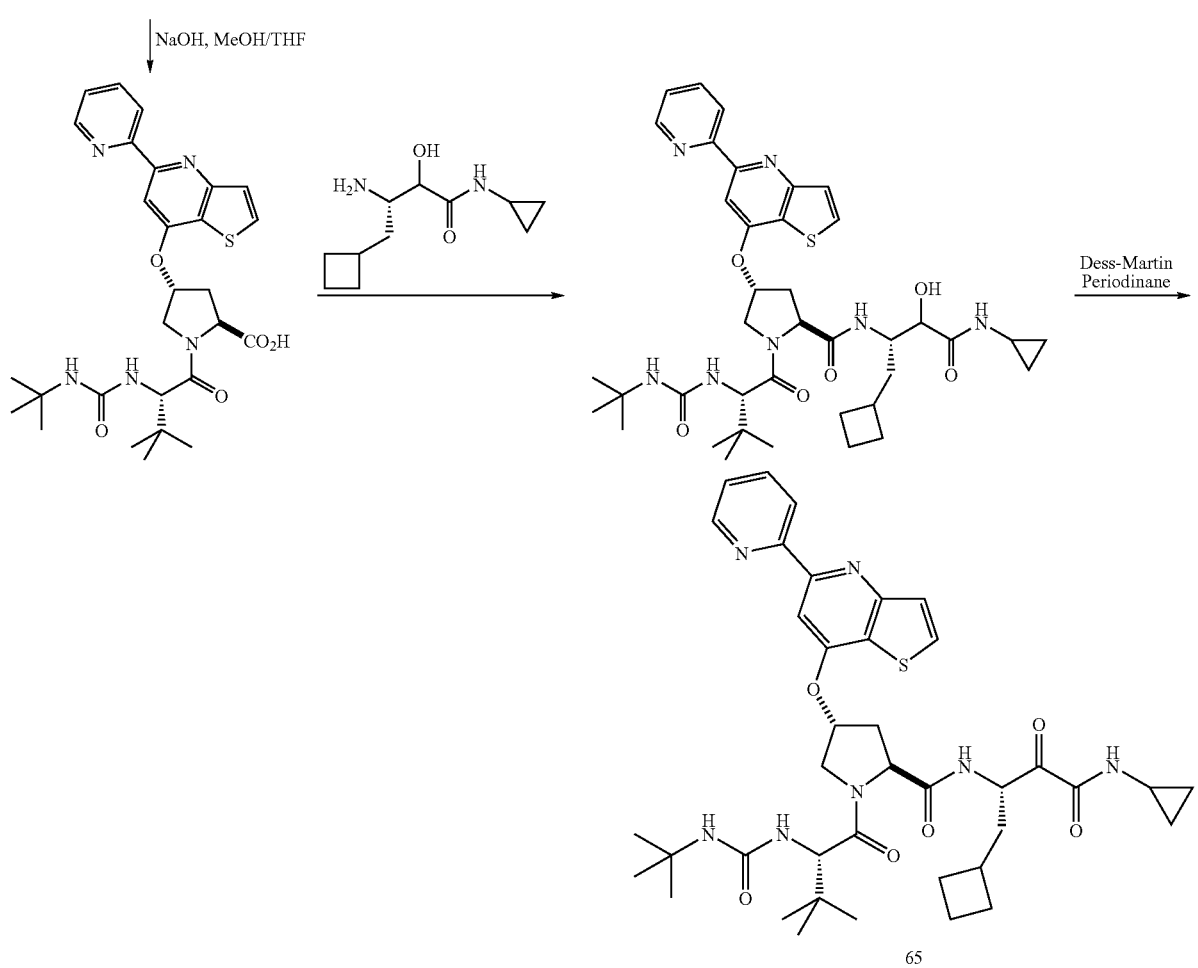

BIOLOGICAL EXAMPLES

Biological Example 1

Biochemical Assay Protocol Used to Determine Inhibition of Cathepsin B

The test compound of Formula (I) was dissolved in dimethylsulfoxide (DMSO) and diluted in assay buffer. An 8 point dose response curve was completed in order to evaluate the $IC_{50}$ value of inhibition of Cathepsin B enzymatic activity ($IC_{50}$ is defined as the concentration which inhibited 50% of maximal enzyme activity). The assay protocol was adapted from Barrett, 1980. Human Liver Cathepsin B was incubated in assay buffer (50 mM sodium acetate, pH 5.5, 1 mM dithiothreitol (DTT), 2 mM ethylenediaminetetraacetic acid (EDTA) with 20 uM peptide substrate (Boc-Leu-Arg-Arg-AMC) with the compounds diluted from DMSO stocks or DMSO vehicle alone. Final DMSO concentration was retained at 1% in the assay. The test compound was preincubated with the enzyme for 15 minutes at 25° C. Reaction was started with the addition of substrate, and allowed to proceed for 30 minutes at 25° C. Substrate cleavage was monitored with spectrofluorimetric quantitation of methylcoumarylamide (AMC).

References

Barrett A J (1980). Fluorimetric assays for Cathepsin B and Cathepsin H with methylcoumarylamide substrates. Biochem J. 187:909-912.

Canbay A et al. (2003). Cathepsin B inactivation attenuates hepatic injury and fibrosis during cholestasis. J. Clin. Invest. 112: 152-159.

Guicciardi M E et al. (2001). Cathepsin B Knockout mice are resistant to tumor necrosis factor-alpha-mediated hepatocyte apoptosis and liver injury. Amer J Pathology 159:2045-2054.

Baskin-Bey E S et al. (2005). Cathepsin B inactivation attenuates hepatocyte apoptosis and liver damage in steatotic livers after cold ischemia-warm reperfusion injury. Am J Physiol Gastrointest Liver Physiol. 288:G396-G402.

Results

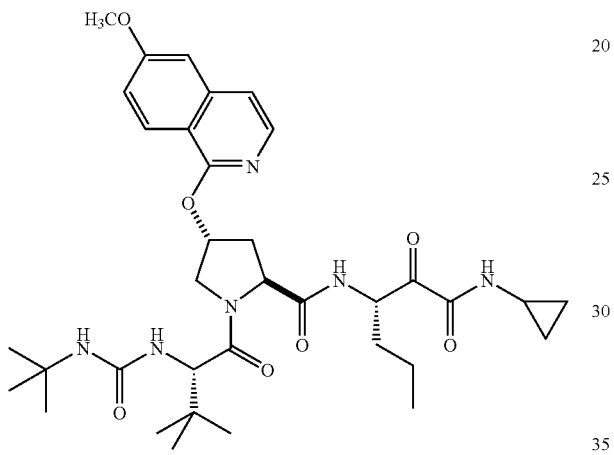

(2S,4R)-1-((S)-2-(3-tert-Butylureido)-3,3-dimethylbutanoyl)-N-((S)-1-cyclopropylamino)-1,2-dioxohexan-3-yl)-4-(6-methoxyisoquinolin-1-yloxy)-pyrrolidine-2-carboxamide Cathepsin B IC$_{50}$: 27 nM:

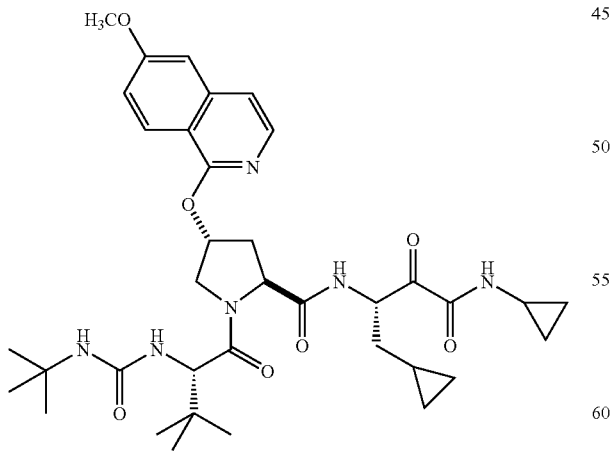

(2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-methoxyisoquinolin-1-yloxy)-pyrrolidine-2-carboxamide Cathepsin B IC$_{50}$: 56 nM:

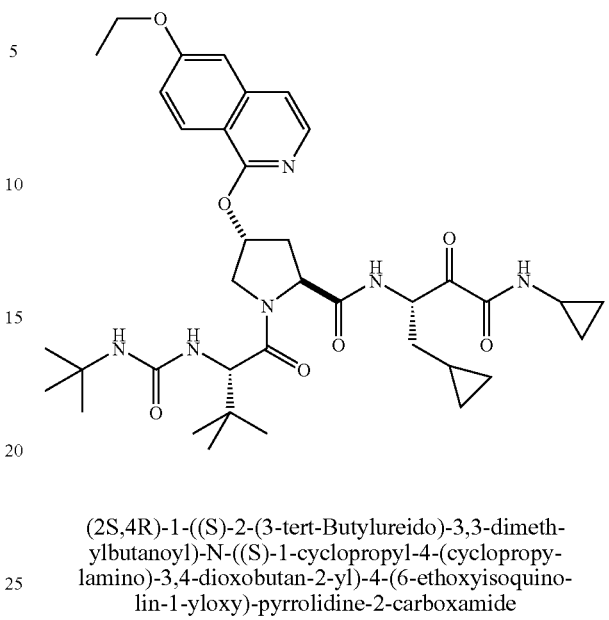

(2S,4R)-1-((S)-2-(3-tert-Butylureido)-3,3-dimethylbutanoyl)-N-((S)-1-cyclopropyl-4-(cyclopropylamino)-3,4-dioxobutan-2-yl)-4-(6-ethoxyisoquinolin-1-yloxy)-pyrrolidine-2-carboxamide Cathepsin B IC$_{50}$: 49 nM:

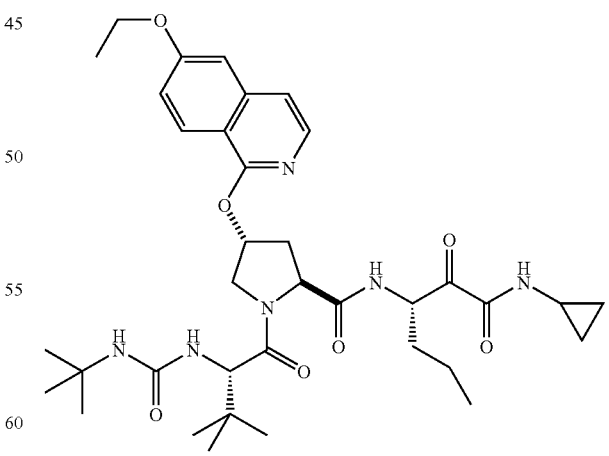

(2S,4R)-1-((S)-2-(3-tert-Butylureido)-3,3-dimethylbutanoyl)-N-((S)-1-(cyclopropylamino)-1,2-dioxohexan-3-yl)-4-(6-ethoxyisoquinolin-1-yloxy)-pyrrolidine-2-carboxamide

87

Cathepsin B IC$_{50}$: 45 nM:

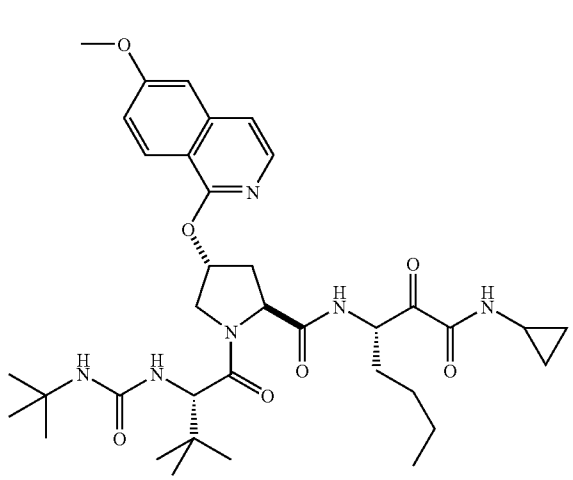

(2S,4R)-1-((S)-2-(3-tert-Butylureido)-3,3-dimethylbutanoyl)-N-((S)-1-cyclopropylamino)-1,2-dioxoheptan-3-yl)-4-(6-methoxyisoquinolin-1-yloxy)-pyrrolidine-2-carboxamide Cathepsin B IC$_{50}$: 28 nM:

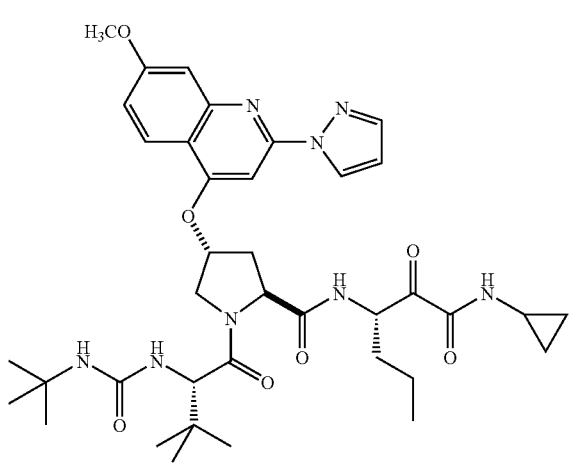

(2S,4R)-1-((S)-2-(3-tert-Butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide

88

Cathepsin B IC$_{50}$: <500 nM:

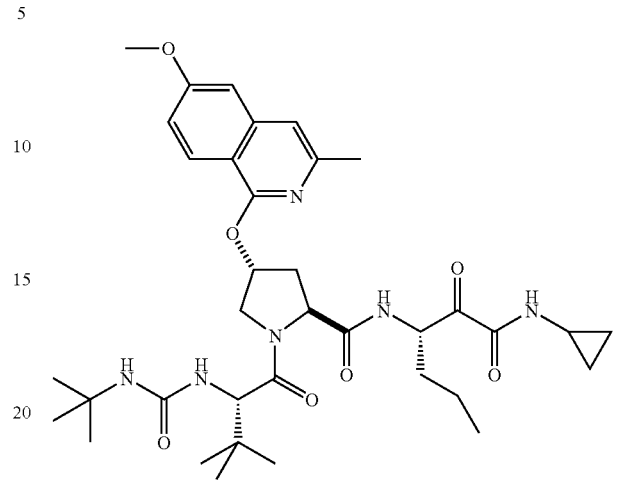

(2S,4R)-1-((S)-2-(3-tert-Butylureido)-3,3-dimethylbutanoyl)-N-((S)-1-cyclopropylamino)-1,2-dioxohexan-3-yl)-4-(6-methoxy-3-methylisoquinolin-1-yloxy)-pyrrolidine-2-carboxamide Cathepsin B IC$_{50}$: 32 nM:

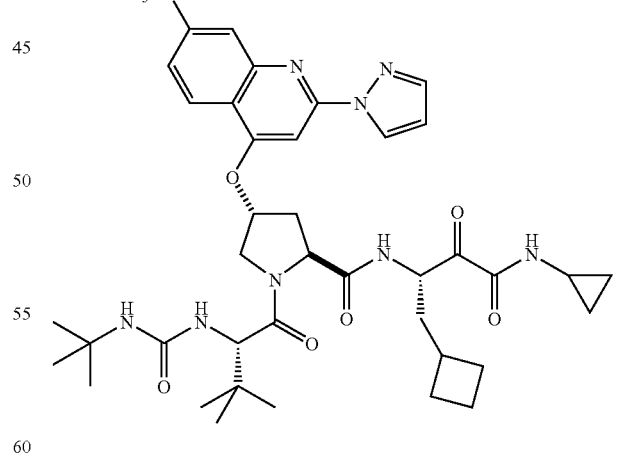

(2S,4R)-1-((S)-2-(3-tert-Butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide

89

Cathepsin B IC$_{50}$: <500 nM:

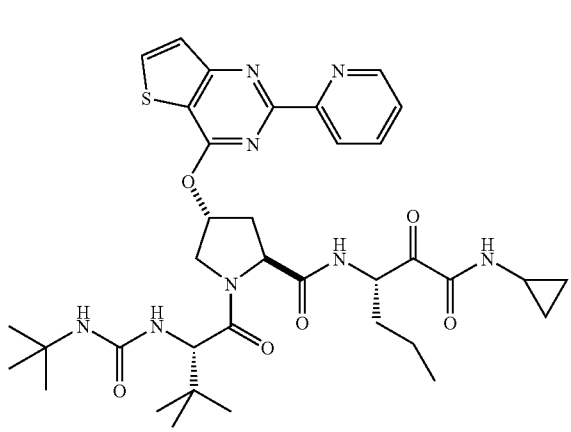

(2S,4R)-1-((S)-2-(3-tert-Butylureido)-3,3-dimethylbutanoyl)-N-((S)-1-cyclopropylamino)-1,2-dioxohexan-3-yl)-4-(2-(pyridin-2-yl)thieno[3,2-d]pyrimidin-4-yloxy)pyrrolidine-2-carboxamide

90

Cathepsin B IC$_{50}$: 86 nM:

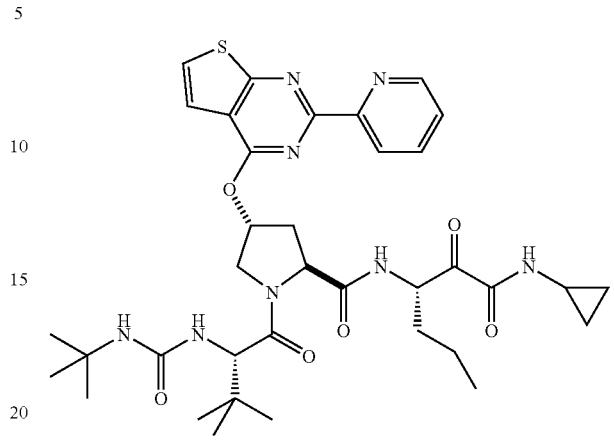

(2S,4R)-1-((S)-2-(3-tert-Butylureido)-3,3-dimethylbutanoyl)-N-((S)-1-cyclopropylamino)-1,2-dioxohexan-3-yl)-4-(2-(pyridin-2-yl)thieno[2,3-d]pyrimidin-4-yloxy)pyrrolidine-2-carboxamide Cathepsin B IC$_{50}$: 33 nM:

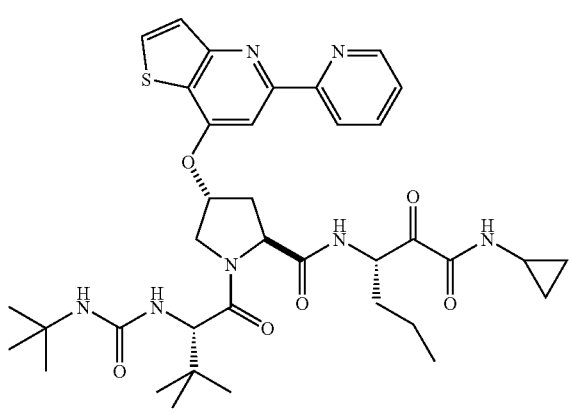

(2S,4R)-1-((S)-2-(3-tert-Butylureido)-3,3-dimethylbutanoyl)-N-((S)-1-cyclopropylamino)-1,2-dioxohexan-3-yl)-4-(5-(pyridin-2-yl)thieno[3,2-b]pyridin-7-yloxy)pyrrolidine-2-carboxamide Cathepsin B IC$_{50}$: 45 nM:

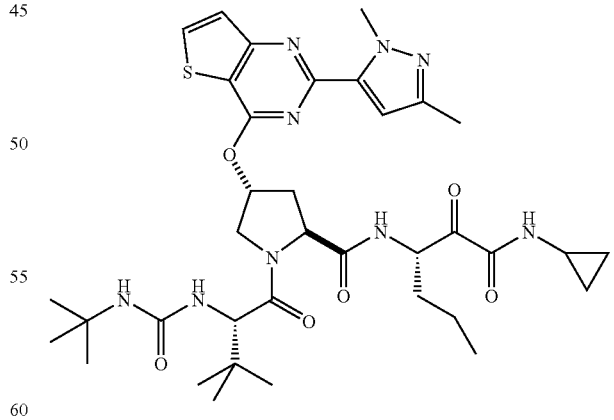

(2S,4R)-1-((S)-2-(3-tert-Butylureido)-3,3-dimethylbutanoyl)-N-((S)-1-cyclopropylamino)-1,2-dioxohexan-3-yl)-4-(2-(1,3-dimethyl-1H-pyrazol-5-yl)thieno[3,2-d]pyrimidin-4-yloxy)pyrrolidine-2-carboxamide Cathepsin B IC$_{50}$: 72 nM:

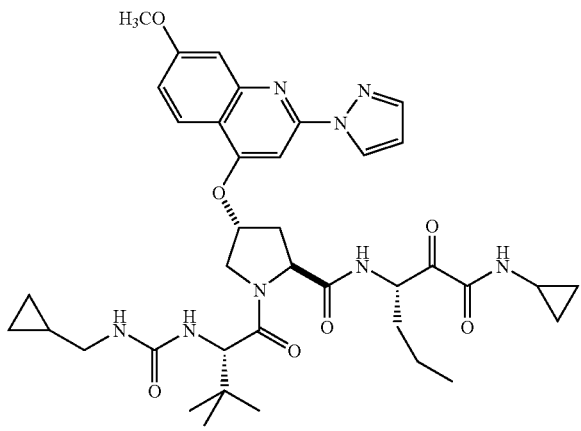

(2S,4R)-N-((S)-1-(cyclopropylamino)-1,2-dioxo-hexan-3-yl)-1-((S)-2-(3-cyclopropylmethyl)ureido)-3,3-dimethylbutanoyl)-4-(7-methoxy-2-(1H-pyrazol-1-yl)quinolin-4-yloxy)pyrrolidine-2-carboxamide Cathepsin B IC$_{50}$: 83 nM:

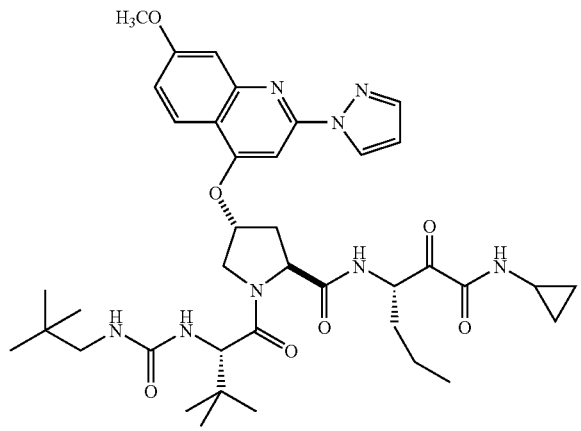

(2S,4R)-N-((S)-1-(cyclopropylamino)-1,2-dioxo-hexan-3-yl)-1-((S)-3,3-dimethyl-2-(3-neopentylure-ido)butanoyl)-4-(7-methoxy-2-(1H-pyrazol-1-yl)quinolin-4-yloxy)pyrrolidine-2-carboxamide Cathepsin B IC$_{50}$: 61 nM:

Biological Example 2

Biochemical Assay Protocol Used to Determine Inhibition of Cathepsin B in Human Cells Test compounds were demonstrated to be potent Cathepsin B inhibitors in human cells and the concentration required for 50% inhibition of Cathepsin B activity in cells (the cellular IC$_{50}$) was determined. Activity of Cathepsin B in cells was measured with the use of an activity-based radioactive probe in a whole-cell enzyme occupancy assay. This method was used to determine the specific potencies of compounds on Cathepsin B in the intracellular environment. The probe used was a peptide diazomethylketone which binds to Cathepsins, including Cathepsin B, potently and irreversibly. This cell-permeable probe binds to active Cathepsin B and binding can be quantified to determine the level of Cathepsin B activity in cells. Cathepsin B enzyme in cells which has bound to an inhibitor is not active and as such not available for binding by the activity-based probe.

Using this method the cell-based IC$_{50}$ for (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide was determined to be 19 nM and the IC$_{50}$ for (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy)pyrrolidine-2-carboxamide was determined to be 24 nM. Assay data are shown in the figure below. The data demonstrated that (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide and (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy)pyrrolidine-2-carboxamide are potent inhibitors of Cathepsin B within the intracellular environment. The data also enable the prediction of concentrations that will be required to inhibit Cathepsin B for therapeutic effect in vivo.

Assay Method:

The method used was based on a modification of a published method (Falgueyret J-P, et al. 2004. Anal. Biochem. 335:218-227). Human umbilical vein endothelial cells (HUVECs) were grown in 24 well plates in standard growth conditions. On the day of the experiment cells were washed twice with HUVEC growth medium without any serum added but supplemented with 2% Nutridoma-HU, which is referred to as serum-free media. Cells were treated with appropriate compound dilutions for 4 hours. One well was left untreated as a no-drug control. This compound treatment was in the serum-free media.

At the end of the 4 hour pre-incubation with the test compounds, activity-based probe was added. The probe used was Z-Tyr-Ala-Diazomethylketone conjugated with $^{125}$I with a specific activity of 2000 Ci/mmol, and referred to as $^{125}$I-DMK. $^{125}$I-DMK was added to each sample well, 4 μL per well. Cells were placed back in a tissue culture incubator for an additional 1 hour. Cells were washed in PBS and then solubilized in an ice cold lysis buffer such as RIPA. Lysates were transferred to tubes and an equal volume of 1× SDS-PAGE gel reducing sample loading buffer was added.

To analyze probe-labeled proteins, samples were boiled for 5 minutes and analyzed by SDS-PAGE. A $^{14}$C-methylated protein molecular weight marker was included to visualize molecular weights. Gels were washed and fixed in destain (50 mL methanol, 50 mL acetic acid, 400 mL water) for 45 minutes on a gently rotating shaker, placed on Whatman paper, and dried on a vacuum gel drier at 70° F. for 2 hours. Dried gels were exposed to film at −80° C. and processed by autoradiography. The band intensities on the autoradiographs were determined. Autoradiographs were scanned using a Microtek ScanMakeri900 scanner and bands quantified with a program such as the BioRad Imaging program QuantityOne or ImageJ. Compound potencies were calculated as a % of the no inhibitor control and IC$_{50}$ values were extrapolated from the dose-response curves using a suitable program like GraphPad Prism.

FIG. 1: Potency of (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide (Compound 1) and (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy)pyrrolidine-2-carboxamide (Compound 2) in Cellular Activity-based Probe Assay Biological Example 3

Biochemical Assay Protocol Used to Determine Inhibition of Liver Fibrosis

Method

Liver fibrosis was induced in mice by intraperitoneal administration of carbon tetrachloride every 5 days over a 28-day period (days 0-28). On day 11, plasma alanine aminotransferase (ALT) levels and aspertate aminotransferase (AST) were measured from representative mice to confirm liver damage. (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy)pyrrolidine-2-carboxamide was administered therapeutically, once daily, starting on day 12, for about 4 weeks. On day 33, terminal plasma AST and ALT, liver hydroxyproline, PK/PD, and histology were assessed.

Figure 2:
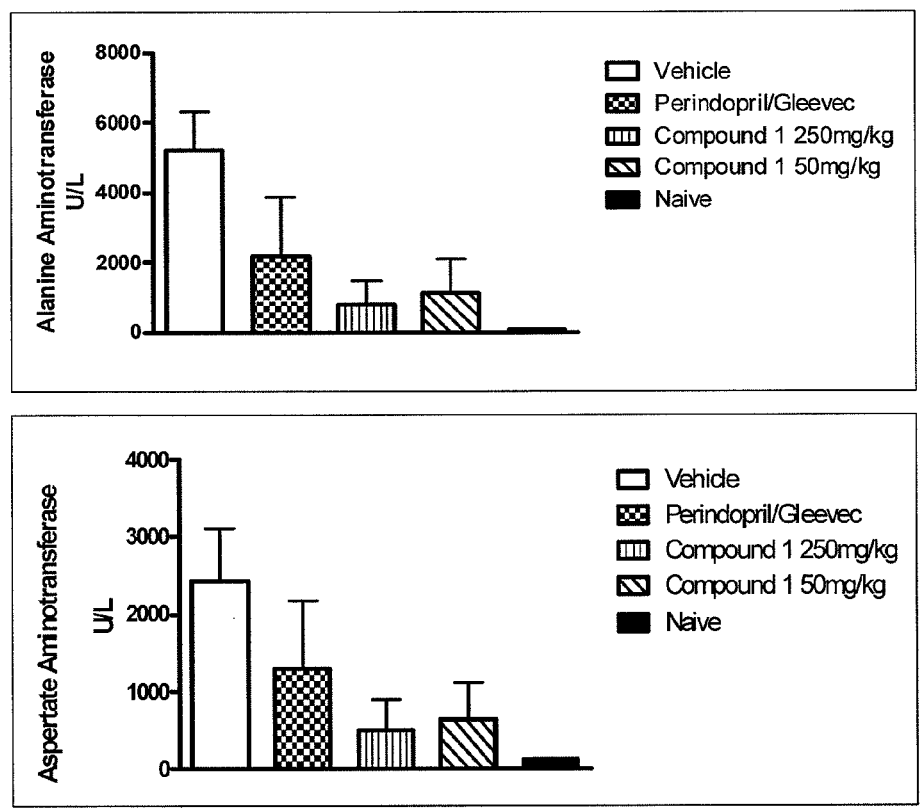
FIGS. 2A and 2B demonstrates that the compound identified as Compound 1 reduces plasma ALT and AST in a Model of Liver Fibrosis.
Figure 3:
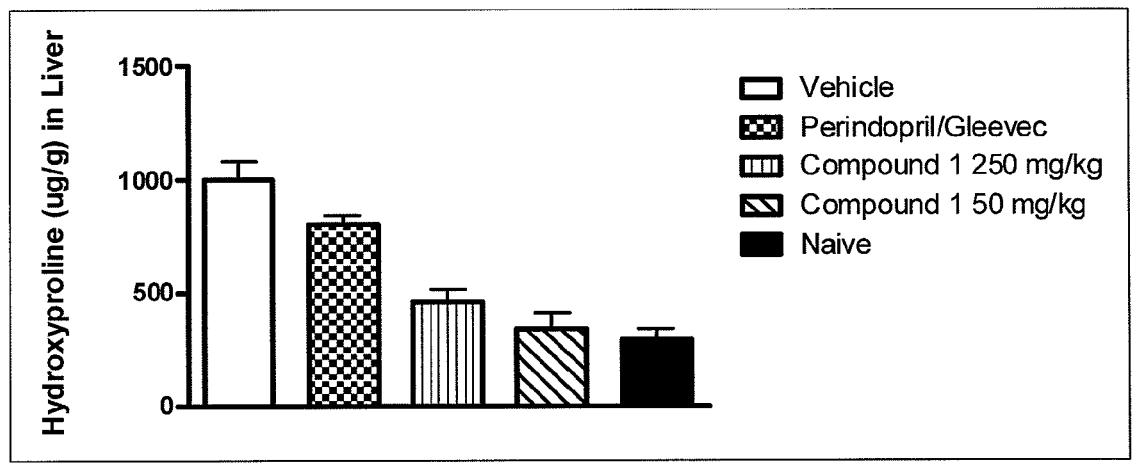
FIG. 3 demonstrates that the compound identified as Compound 1 reduces Liver Hydroxyproline Levels in a Model of Liver Fibrosis.

Results: (2S,4R)-1-((S)-(3-tert-butylureido)-3,3-dimethylbutanoyl]-N-((S)-1-cyclopropylamino)-1,2-dioxohexan-3-yl)-4-(7-methoxy-2-(1H-pyrazol-1-yl)-quinolin-4-yloxy) pyrrolidine-2-carboxamide decreased plasma AST and ALT (FIGS. 2A and 2B) and hydroxyproline (FIG. 3) at both doses assessed (250 mg/kg and 50 mg/kg).

Pharmaceutical Formulation Examples

Representative pharmaceutical formulations containing a Compound of Formula (I)

Oral Formulation

| Compound of Formula (I) | 10-100 mg |
| Citric Acid Monohydrate | 105 mg |
| Sodium Hydroxide | 18 mg |
| Flavoring | |
| Water | q.s. to 100 mL |

Intravenous Formulation

| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A method of treating diseases mediated by Cathepsin B in a mammal,
wherein the diseases mediated by Cathepsin B are selected from the group consisting of Alzheimer's Disease, arthritis, muscular dystrophy, inflammation, glomerulonephritis, periodontal disease, metachromatic leukodystrophy, tumor invasion, metastasis, chronic and acute pancreatitis, inflammatory airway disease, osteoporosis, osteoarthritis, rheumatoid arthritis, psoriasis, fibrotic disease, steatosis, non-alcoholic steatohepatitis, alcohol-associated steatohepatitis, non-alcoholic fatty liver disease, pulmonary fibrosis, idiopathic pulmonary fibrosis, renal fibrosis, cardiac fibrosis, retinal angiogenesis, fibrosis/gliosis in the eye, scleroderma, and systemic sclerosis
comprising administering to a subject in need thereof a therapeutically effective amount of a compound of Formula (I):

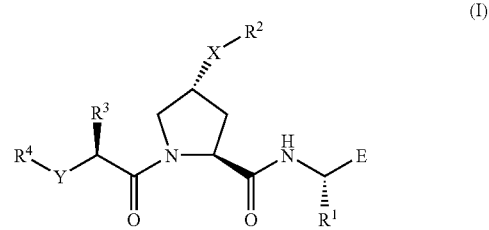

wherein

E is a member selected from the group consisting of —COCONR$^5$R$^6$, —COCF$_2$CONR$^5$R$^6$, —COCF$_2$C(O)OR$^5$, —COCOR$^7$, —COCF$_2$R$^8$, —COR$^9$, —COCOOR$^{10}$, —CONR$^{11}$R$^{12}$, and —B(OR$^{13}$)$_2$, wherein R$^5$, R$^6$, R$^7$, R$^9$, R$^{10}$, R$^{11}$, R$^{12}$ and each R$^{13}$ is independently selected from hydrogen, alkyl, alkenyl, alkynyl, cycloalkyl, cycloalkylalkyl, aryl, aralkyl, heteroaryl, heteroaralkyl, heterocyclyl, and heterocyclylalkyl and R$^8$ is selected from halo, alkyl, alkenyl, alkynyl, cycloalkyl, cycloalkylalkyl, aryl, aralkyl, heteroaryl, heteroaralkyl, heterocyclyl, and heterocyclylalkyl, wherein the aliphatic, alicyclic and aromatic groups in E are optionally substituted with one, two, or three R$^a$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, alkenyloxycarbonyl, alkynyloxycarbonyl, alkenylaminocarbonyl, acylamino, aminocarbonyl, halo, and cyano, and further wherein the aromatic or alicyclic ring in R$^a$ is optionally substituted with one, two, or three substituents independently selected from alkyl, alkoxy, halo, haloalkyl, haloalkoxy, cyano, carboxy, and carboxyalkyl; and optionally, $R^5$ and $R^6$, and $R^{11}$ and $R^{12}$ can be combined with the nitrogen to which they are attached to form a five- to seven-membered ring;

$R^1$ is a member selected from the group consisting of alkyl, haloalkyl, alkenyl, alkynyl, cycloalkyl, cycloalkylalkyl, aryl, aralkyl, heteroaryl, heteroaralkyl, heterocyclyl and heterocyclylalkyl, wherein the aliphatic, alicyclic and aromatic groups in $R^1$ are optionally substituted with one or two $R^b$ independently selected from hydroxy, alkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano, and further wherein any aromatic or alicyclic ring in $R^b$ is optionally substituted with one, two, or three substituents independently selected from alkyl, alkoxy, halo, haloalkyl, haloalkoxy, cyano, carboxy, and carboxyalkyl;

X is a member selected from the group consisting of —O—, —NR$^{14}$—, —S—, —SO—, and —SO$_2$—;

$R^3$ is a member selected from the group consisting of alkyl, haloalkyl, alkenyl, alkynyl, cycloalkyl, cycloalkylalkyl, aryl, aralkyl, heteroaryl, heteroaralkyl, heterocyclyl and heterocyclylalkyl, wherein any aliphatic, alicyclic and aromatic groups in $R^3$ are optionally substituted with one or two $R^c$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano, and further wherein any aromatic or alicyclic ring in $R^c$ is optionally substituted with one, two, or three substituents independently selected from alkyl, alkoxy, halo, haloalkyl, haloalkoxy, carboxy, and carboxyalkyl;

Y is a member selected from the group consisting of —C(O)NH—, —OC(O)NH—, —NR$^{14}$—C(O)NH—, and —NR$^{14}$C(O)O—, wherein each R$^{14}$ is selected from hydrogen and alkyl, wherein the alkyl is optionally substituted with halo, hydroxy, alkoxy, amino, monosubstituted amino, disubstituted amino, aryl, heteroaryl or heterocyclyl, and wherein each aryl, heteroaryl and heterocyclyl is optionally substituted with one, two or three substituents selected from halo and alkyl;

$R^2$ is selected from the group consisting of heteroaryl and —CO-(fused heterocyclyl), wherein the heteroaryl and fused heterocyclyl rings are optionally substituted with one, two, three, or four $R^d$ independently selected from hydrogen, alkyl, alkenyl, alkynyl, alkylthio, hydroxy, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, amino, monosubstituted amino, and disubstituted amino, or when two $R^d$ are on adjacent carbon atoms they together with the carbon atoms to which they are attached form a four, five or six membered heterocyclyl ring containing one or two heteroatoms selected from nitrogen, oxygen, sufur, and —SO$_2$— wherein the heterocyclyl ring is optionally substituted with one or two alkyl; and further wherein any aromatic or alicyclic ring in $R^d$ is optionally substituted with one, two, or three $R^e$ independently selected from alkyl, alkylcarbonylamino, alkoxycarbonylamino, cycloalkyl, cycloalkylalkyl, cycloalkoxycarbonylamino, cycloalkylalkyloxycarbonylamino, nitro, alkoxy, cycloalkyloxy, aryloxy, heteroaryloxy, halo, haloalkyl, haloalkoxy, hydroxyl, carboxy, alkoxycarbonyl, amino, monosubstituted amino, disubstituted amino, acylamino, and ureido, wherein cycloalkyl and cycloalkylalkyl in $R^e$ are optionally substituted with one, two or three alkyl; and $R^4$ is a member selected from the group consisting of alkyl, cycloalkyl, cycloalkylalkyl, aryl, aralkyl, heteroaryl, heteroaralkyl, heterocyclyl, and heterocyclylalkyl; wherein any aromatic or alicyclic ring in $R^4$ is optionally substituted with one, two, or three $R^f$ independently selected from alkyl, alkoxy, halo, haloalkyl, haloalkoxy, cyano, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroaryl sulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, and disubstituted amino, wherein any aromatic or alicyclic ring in $R^f$ is optionally substituted with one, two, or three substituents independently selected from alkyl, alkoxy, halo, haloalkyl, haloalkoxy, hydroxy, carboxy, alkoxycarbonyl, monosubstituted amino, disubstituted amino, and acylamino; or a pharmaceutically acceptable salt thereof.

2. The method of claim 1, wherein X is oxygen and $R^2$ is heteroaryl.

3. The method of claim 2, wherein $R^2$ is a 9 or 10 membered bicyclic heteroaryl group containing 1, 2, or 3 hetero atoms selected from the group consisting of nitrogen, oxygen, and sulfur.

4. The method of claim 3, wherein the 9 or 10 membered bicyclic heteroaryl group is optionally substituted with 1, 2 or 3 groups selected from the group consisting of alkyl, alkoxy, halo, and monocyclic heteroaryl.

5. The method of claim 4, wherein E is —C(O)C(O)NR$^5$R$^6$.

6. The method of claim 5, wherein $R^5$ is hydrogen and $R^6$ is alkyl or cycloalkyl.

7. The method of claim 6, wherein $R^6$ is cyclopropyl or cyclobutyl.

8. The method of claim 7, wherein $R^1$ is alkyl, cycloalkyl, and cycloalkylalkyl.

9. The method of claim 8, wherein $R^1$ is methyl, ethyl, n-propyl, isopropyl, n-butyl, isobutyl, tert-butyl, cyclopropyl, cyclopropylmethyl, cyclobutyl, and cyclobutylmethyl.

10. The method of claim 9, wherein $R^3$ is alkyl, cycloalkyl, and cycloalkylalkyl and $R^4$ is alkyl, cycloalkyl, and cycloalkylalkyl.

11. The method of claim 10, wherein $R^3$ is methyl, ethyl, n-propyl, isopropyl, n-butyl, isobutyl, and tert-butyl and $R^4$ is methyl, ethyl, n-propyl, isopropyl, n-butyl, isobutyl, tert-butyl, cyclopropyl, cyclopropylmethyl, cyclobutyl, and cyclobutylmethyl.

12. The method of claim 11, wherein Y is —NR$^{14}$C(O)NH— and $R^4$ is alkyl or cycloalkyl.

13. The method of claim 12, wherein $R^3$ and $R^4$ are both tert-butyl and R$^{14}$ is hydrogen.

14. The method of claim 13, wherein $R^2$ is quinolinyl or isoquinolinyl optionally substituted with alkoxy and heteroaryl.

15. The method of claim 14, wherein $R^2$ is quinolinyl or isoquinolinyl substituted with methoxy and pyrazolyl.

16. The method of claim 1, wherein the compound of Formula (I) is selected the group consisting of:
- (2S,4R)-1-((S)-2-(3-tert-butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide;
- (2S,4R)-1-((S)-2-(3-tert-butylureido)-3,3-dimethylbutanoyl)-N-((S)-1-cyclopropylamino)-1,2-dioxohexan-3-yl)-4-(6-methoxyisoquinolin-1-yloxy)-pyrrolidine-2-carboxamide;
- (2S,4R)-1-((S)-2-(3-tert-Butylureido)-3,3-dimethylbutanoye-N-((S)-1-cyclopropyl-4-(cyclopropylamino)-3,4-dioxobutan-2-yl)-4-(6-methoxyisoquinolin-1-yloxy)-pyrrolidine-2-carboxamide;
- (2S,4R)-1-((S)-2-(3-tert-butylureido)-3,3-dimethylbutanoyl)-N-((S)-1-cyclopropyl-4-(cyclopropylamino)-3,4-dioxobutan-2-yl)-4-(6-ethoxyisoquinolin-1-yloxy)-pyrrolidine-2-carboxamide;
- (2S,4R)-1-((S)-2-(3-tert-butylureido)-3,3-dimethylbutanoyl)-N-((S)-1-(cyclopropylamino)-1,2-dioxohexan-3-yl)-4-(6-ethoxyisoquinolin-1-yloxy)-pyrrolidine-2-carboxamide;
- (2S,4R)-1-((S)-2-(3-tert-butylureido)-3,3-dimethylbutanoyl)-N-((S)-1-cyclopropylamino)-1,2-dioxoheptan-3-yl)-4-(6-methoxyisoquinolin-1-yloxy)-pyrrolidine-2-carboxamide;
- (2S,4R)-1-((S)-2-(3-tert-butylureido)-3,3-dimethylbutanoye-N-((S)-1-cyclopropylamino)-1,2-dioxohexan-3-yl)-4-(6-methoxy-3-methylisoquinolin-1-yloxy)-pyrrolidine-2-carboxamide;
- (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide;
- (2S,4R)-1-((S)-2-(3-tert-butylureido)-3,3-dimethylbutanoyl)-N-((S)-1-cyclopropylamino)-1,2-dioxohexan-3-yl)-4-(2-(pyridin-2-yl)thieno[3,2-d]pyrimidin-4-yloxy)pyrrolidine-2-carboxamide;
- (2S,4R)-1-((S)-2-(3-tert-butylureido)-3,3-dimethylbutanoyl)-N-((S)-1-cyclopropylamino)-1,2-dioxohexan-3-yl)-4-(5-(pyridin-2-yl)thieno[3,2-b]pyridin-7-yloxy)pyrrolidine-2-carboxamide;
- (2S,4R)-1-((S)-2-(3-tert-butylureido)-3,3-dimethylbutanoyl)-N-((S)-1-cyclopropylamino)-1,2-dioxohexan-3-yl)-4-(2-(pyridin-2-yl)thieno[2,3-d]pyrimidin-4-yloxy)pyrrolidine-2-carboxamide;
- (2S,4R)-1-((S)-2-(3-tert-butylureido)-3,3-dimethylbutanoyl)-N-((S)-1-cyclopropylamino)-1,2-dioxohexan-3-yl)-4-(2-(1,3-dimethyl-1H-pyrazol-5-yl)thieno[3,2-d]pyrimidin-4-yloxy)pyrrolidine-2-carboxamide;
- (2S,4R)-N-((S)-1-(cyclopropylamino)-1,2-dioxohexan-3-yl)-1-((S)-2-(3-cyclopropylmethyl)ureido)-3,3-dimethylbutanoyl)-4-(7-methoxy-2-(1H-pyrazol-1-yl)quinolin-4-yloxy)pyrrolidine-2-carboxamide; and
- (2S,4R)-N-((S)-1-(cyclopropylamino)-1,2-dioxohexan-3-yl)-1-((S)-3,3-dimethyl-2-(3-neopentylureido)butanoyl)-4-(7-methoxy-2-(1H-pyrazol-1-yl)quinolin-4-yloxy)pyrrolidine-2-carboxamide.

17. The method of claim 16, wherein the compound of Formula (I) is (2S,4R)-1-((S)-2-(3-tert-butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide.

18. The method of claim 16, wherein the compound of Formula (I) is (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy)pyrrolidine-2-carboxamide.

19. The method of claim 1, wherein the disease mediated by Cathepsin B is a fibrotic disease.

20. The method of claim 1, wherein the fibrotic disease is liver fibrosis.

21. A method of treating a subject diagnosed with both HCV and fibrosis in a mammal, comprising administering to said mammal an effective amount of a compound of Formula (I) suitable to treat both HCV and fibrosis:

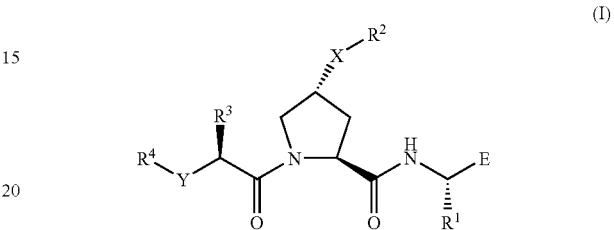

wherein
E is a member selected from the group consisting of —COCONR$^5$R$^6$, —COCF$_2$CONR$^5$R$^6$, —COCF$_2$C(O)OR$^5$, —COCOR$^7$, —COCF$_2$R$^8$, —COR$^9$, —COCOOR$^{10}$, —CONR$^{11}$R$^{12}$, and —B(OR$^{13}$)$_2$, wherein R$^5$, R$^6$, R$^7$, R$^9$, R$^{10}$, R$^{11}$, R$^{12}$ and each R$^{13}$ is independently selected from hydrogen, alkyl, alkenyl, alkynyl, cycloalkyl, cycloalkylalkyl, aryl, aralkyl, heteroaryl, heteroaralkyl, heterocyclyl, and heterocyclylalkyl and R$^8$ is selected from halo, alkyl, alkenyl, alkynyl, cycloalkyl, cycloalkylalkyl, aryl, aralkyl, heteroaryl, heteroaralkyl, heterocyclyl, and heterocyclylalkyl, wherein the aliphatic, alicyclic and aromatic groups in E are optionally substituted with one, two, or three R$^a$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, alkenyloxycarbonyl, alkynyloxycarbonyl, alkenylaminocarbonyl, acylamino, aminocarbonyl, halo, and cyano, and further wherein the aromatic or alicyclic ring in R$^a$ is optionally substituted with one, two, or three substituents independently selected from alkyl, alkoxy, halo, haloalkyl, haloalkoxy, cyano, carboxy, and carboxyalkyl; and optionally, R$^5$ and R$^6$, and R$^{11}$ and R$^{12}$ can be combined with the nitrogen to which they are attached to form a five- to seven-membered ring;

R$^1$ is a member selected from the group consisting of alkyl, haloalkyl, alkenyl, alkynyl, cycloalkyl, cycloalkylalkyl, aryl, aralkyl, heteroaryl, heteroaralkyl, heterocyclyl and heterocyclylalkyl, wherein the aliphatic, alicyclic and aromatic groups in R$^1$ are optionally substituted with one or two R$^b$ independently selected from hydroxy, alkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano, and further wherein any aromatic or alicyclic ring in R$^b$ is optionally substituted with one, two, or three substituents independently selected from alkyl, alkoxy, halo, haloalkyl, haloalkoxy, cyano, carboxy, and carboxyalkyl;

X is a member selected from the group consisting of —O—, —NR$^{14}$—, —S—, —SO—, and —SO$_2$—;

R$^3$ is a member selected from the group consisting of alkyl, haloalkyl, alkenyl, alkynyl, cycloalkyl, cycloalkylalkyl, aryl, aralkyl, heteroaryl, heteroaralkyl, heterocyclyl and heterocyclylalkyl, wherein any aliphatic, alicyclic and aromatic groups in R$^3$ are optionally substituted with one or two R$^c$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, and cyano, and further wherein any aromatic or alicyclic ring in R$^c$ is optionally substituted with one, two, or three substituents independently selected from alkyl, alkoxy, halo, haloalkyl, haloalkoxy, carboxy, and carboxyalkyl;

Y is a member selected from the group consisting of —C(O)NH—, —OC(O)NH—, —NR$^{14}$—C(O)NH—, and —NR$^{14}$C(O)O—, wherein each R$^{14}$ is selected from hydrogen and alkyl, wherein the alkyl is optionally substituted with halo, hydroxy, alkoxy, amino, monosubstituted amino, disubstituted amino, aryl, heteroaryl or heterocyclyl, and wherein each aryl, heteroaryl and heterocyclyl is optionally substituted with one, two or three substituents selected from halo and alkyl;

R$^2$ is selected from the group consisting of heteroaryl and —CO-(fused heterocyclyl), wherein the heteroaryl and fused heterocyclyl rings are optionally substituted with one, two, three, or four R$^d$ independently selected from hydrogen, alkyl, alkenyl, alkynyl, alkylthio, hydroxy, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroaryl sulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, amino, monosubstituted amino, and disubstituted amino, or when two R$^d$ are on adjacent carbon atoms they together with the carbon atoms to which they are attached form a four, five or six membered heterocyclyl ring containing one or two heteroatoms selected from nitrogen, oxygen, sufur, and —SO$_2$— wherein the heterocyclyl ring is optionally substituted with one or two alkyl; and further wherein any aromatic or alicyclic ring in R$^d$ is optionally substituted with one, two, or three R$^e$ independently selected from alkyl, alkylcarbonylamino, alkoxycarbonylamino, cycloalkyl, cycloalkylalkyl, cycloalkoxycarbonylamino, cycloalkylalkyloxycarbonylamino, nitro, alkoxy, cycloalkyloxy, aryloxy, heteroaryloxy, halo, haloalkyl, haloalkoxy, hydroxyl, carboxy, alkoxycarbonyl, amino, monosubstituted amino, disubstituted amino, acylamino, and ureido, wherein cycloalkyl and cycloalkylalkyl in R$^e$ are optionally substituted with one, two or three alkyl; and R$^4$ is a member selected from the group consisting of alkyl, cycloalkyl, cycloalkylalkyl, aryl, aralkyl, heteroaryl, heteroaralkyl, heterocyclyl, and heterocyclylalkyl; wherein any aromatic or alicyclic ring in R$^4$ is optionally substituted with one, two, or three R$^f$ independently selected from alkyl, alkoxy, halo, haloalkyl, haloalkoxy, cyano, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, and disubstituted amino, wherein any aromatic or alicyclic ring in R$^f$ is optionally substituted with one, two, or three substituents independently selected from alkyl, alkoxy, halo, haloalkyl, haloalkoxy, hydroxy, carboxy, alkoxycarbonyl, monosubstituted amino, disubstituted amino, and acylamino; or a pharmaceutically acceptable salt thereof.

22. The method of claim 21, wherein the fibrosis is liver fibrosis.

23. The method of claim 22, wherein the subject is affirmatively diagnosed with both HCV and liver fibrosis.

24. The method of claim 22, wherein the subject is at risk of acquiring both HCV and liver fibrosis.

25. The method of claim 21, wherein the compound of Formula (I) is (2S,4R)-1-(S)-2-(3-tert-butylureido)-3,3-dimethylbutanoyl)-N-((S)-1-cyclopropylamino)-1,2-dioxohexan-3-yl)-4-(7-methoxy-2-(1H-pyrazol-1-yl)quinolin-4-yloxy)pyrrolidine-2-carboxamide or (2S,4R)-1-((S)-2-(3-tert-butylureido)-3,3-dimethylbutanoyl)-N-((S)-1-cyclobutyl-4-(cyclopropylamino)-3,4-dioxobutan-2-yl)-4-(7-methoxy-2-(1H-pyrazol-1-yl)quinolin-4-yloxy) pyrrolidine-2-carboxamide.

* * * * *